(12) United States Patent
Ban et al.

(10) Patent No.: US 9,828,362 B2
(45) Date of Patent: Nov. 28, 2017

(54) 1,4-DISUBSTITUTED IMIDAZOLE DERIVATIVE

(71) Applicant: Sumitomo Dainippon Pharma Co., Ltd., Osaka (JP)

(72) Inventors: Hitoshi Ban, Osaka (JP); Manabu Kusagi, Osaka (JP); Shingo Tojo, Osaka (JP); Futoshi Hasegawa, Osawa (JP); Miki Hashizume, Osaka (JP)

(73) Assignee: Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 15/443,892

(22) Filed: Feb. 27, 2017

(65) Prior Publication Data
US 2017/0166552 A1    Jun. 15, 2017

Related U.S. Application Data

(63) Continuation of application No. PCT/JP2016/068423, filed on Jun. 21, 2016.

(30) Foreign Application Priority Data

Jun. 22, 2015  (JP) ................................ 2015-125174
Dec. 16, 2015  (JP) ................................ 2015-244856

(51) Int. Cl.
    *C07D 401/12*    (2006.01)
(52) U.S. Cl.
    CPC .................................. *C07D 401/12* (2013.01)
(58) Field of Classification Search
    None
    See application file for complete search history.

(56) References Cited

U.S. PATENT DOCUMENTS

| | | | |
|---|---|---|---|
| 5,817,677 A | 10/1998 | Linz et al. | |
| 6,310,070 B1 * | 10/2001 | Yokoyama | C07D 473/30 514/263.3 |

FOREIGN PATENT DOCUMENTS

| | | |
|---|---|---|
| JP | S5359664 | 5/1978 |
| WO | WO 2005/092864 | 10/2005 |
| WO | WO 2006/001750 | 1/2006 |
| WO | WO 2006/087355 | 8/2006 |
| WO | WO 2006/114313 | 11/2006 |
| WO | WO 2007/073299 | 6/2007 |
| WO | WO 2008/073461 | 6/2008 |
| WO | WO 2009/060054 | 5/2009 |
| WO | WO 2012/126932 | 9/2012 |
| WO | WO 2015/151490 | 10/2015 |

OTHER PUBLICATIONS

Al-Hajj et al., "Self-renewal and solid tumor stem cells," Oncogene, 2004, 23(43):7274-7282.
Boman et al., "Cancer Stem Cells: A Step Toward the Cure," Journal of Clinical Oncology, Jun. 2008, 26(17):2795-2799.
Haberhauer G. et al., European Journal of Chemistry, 2007, 11, 1779-1792.
Hiroki Yamaguchi (presenter), Nobuyuki Sawada, Miki Hashizume, Toshiyuki Kamei, Futoshi Hasegawa, and Tsutomu Mimoto, "Research and Synthesis of stearoyl-CoA desaturase 1 inhibitors" The 27th medicinal chemistry symposium, Nov. 26-28, 2008, Mielparque Osaka.
Hiroki Yamaguchi, "Inhibitors of Stearoyl-CoA Desaturase 1 as Anti-obesity Drug", Monthly Fine Chemicals, Aug. 2009 (issued date: Jul. 15, 2009), vol. 38, No. 8, p. 12-24, published by CMC Publishing Co., Ltd. and English abstract thereof, (partial English translation only).
Hiroki Yamaguchi, Nobuyuki Sawada, Miki Hashizume, Toshiyuki Kamei, Futoshi Hasegawa, and Tsutomu Mimoto, "Research and Synthesis of stearoyl-CoA desaturase 1 inhibitors", The 27th medicinal chemistry symposium abstracts (edited by executive committee of the 27th medicinal chemistry symposium), p. 166-167, Nov. 10, 2008, published by The Pharmaceutical Society of Japan, Division of Medicinal Chemistry (with English abstract), (Eng. abstract only).
International Search Report in International Application No. PCT/JP2016/068423, dated Aug. 23, 2016, 4 pages.
Lobo et al., "The Biology of Cancer Stem Cells," Annu. Rev. Cell Dev. Biol., 2007, 23:675-699.
Hiroki Yamaguchi, Nobuyuki Sawada, Miki Hashizume, Toshiyuki Kamei, Futoshi Hasegawa, and Tsutomu Mimoto, "Research and Synthesis of stearoyl-CoA desaturase 1 inhibitors", The 27th medicinal chemistry symposium abstracts (edited by executive committee of the 27th medicinal chemistry symposium), p. 166-167, Nov. 10, 2008, published by The Pharmaceutical Society of Japan, Division of Medicinal Chemistry (with English abstract), (Eng. abstract only).
International Search Report in International Application No. PCT/JP2016/068423, dated Aug. 23, 2016, 4 pages.
Lobo et al., "The Biology of Cancer Stem Cells," Annu. Rev. Cell Dev. Biol., 2007, 23:675-699.

(Continued)

Primary Examiner — Matthew Coughlin
Assistant Examiner — Po-Chih Chen
(74) Attorney, Agent, or Firm — Fish & Richardson P.C.

(57) ABSTRACT

The present invention provides a 1,4-disubstituted imidazole derivative of formula (1') wherein ring $Q^1$ is optionally-substituted $C_{6-10}$ aryl group, etc.; $R^1$ and $R^2$ are independently hydrogen atom, etc.; $W^1$ is optionally-substituted $C_{1-4}$ alkylene group; $W^2$ is —$NR^{3a}C(O)$— wherein $R^{3a}$ is hydrogen atom or $C_{1-6}$ alkyl group, etc.; ring $Q^2$ is 5- to 10-membered heteroaryl group, etc.; $W^3$ is optionally-substituted $C_{1-4}$ alkylene group, etc.; n is 1, 2, 3, 4, or 5; $R^4$ is independently halogen atom, optionally-substituted $C_{1-6}$ alkyl group, etc.; $R^5$ is hydroxy group, etc.; and a pharmacologically acceptable salt thereof, which have a potent inhibitory effect on the sphere-forming capacity of cancer cells and are useful as an orally-available anti-tumor agent.

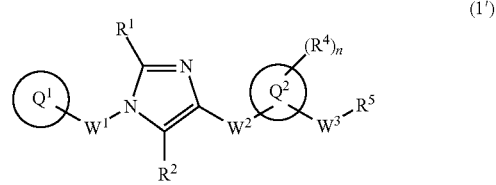

(1')

14 Claims, No Drawings

(56) References Cited

OTHER PUBLICATIONS

Ponti et al., "Isolation and in vitro Propagation of Tumorigenic Breast Cancer Cells with Stem/Progenitor Cell Properties," Cancer Res., Jul. 2005, 65(13):5506-5511.
Zhang et al., "Synergistic Effect of the γ-Secretase Inhibitor PF-03084014 and Docetaxel in Breast Cancer Models," Stem Cells Translational Medicine, 2013, 2:233-242.
Atkinson et al., "N-Benzylimidazole carboxamides as potent, orally active stearoylCoA desaturase-1 inhibitors," Bioorganic & Medicinal Chemistry Letters, 2011, 21: 1621-1625.
CAS RN 1251594-36-1, STN Entry Date Nov. 3, 2010, 1 page.
CAS RN 1251699-10-1, STN Entry Date Nov. 3, 2010, 1 page.
CAS RN 1351771-27-1, STN Entry Date Dec. 23, 2011, 1 page.
CAS RN 1351788-43-6, STN Entry Date Dec. 23, 2011, 1 page.
Delest et al., "Synthesis of 1-benzyl-8,9-dihydroirnidazo [4,5-c] pyrrolo [3,2-g]-quinolin-4(5H)-one via palladium-catalyzed intramolecular arylation," Tetahedron, 2004, 60: 6079-6083.
Deng et al., "Discovery of liver-targeted inhibitors of stearoyl-CoA desaturase (SCD1)," Bioorganic & Medicinal Chemistry Letters, 2013, 23: 791-796.
Helal et al., "Potent and cellularly active 4-aminoimidazole inhibitors of cyclin-dependent kinase 5/p25 for the treatment of Alzheimer's disease," Bioorganic & Medicinal Checmistry Letters, 2009, 5703-5707.
Su and Buchwald, "A Bulky Biaryl Phosphine Ligand Allows for Palladiun-Catalyzed Amidation of Five-Membered Heterocycles as Electrophiles," Agnew Chem Int Ed, 2012, 51: 4710-4713.

\* cited by examiner

1,4-DISUBSTITUTED IMIDAZOLE DERIVATIVE

CROSS-REFERENCE TO RELATED APPLICATIONS

This application is a continuation of international Application. No. PCT/JP2016/068423, filed on Jun. 21, 2016, which claims the benefit of Japanese Application No. 2015-25174, filed on Jun. 22, 2015, the entire contents of each are hereby incorporated by reference.

TECHNICAL FIELD

The present invention relates to a pharmaceutically-useful 1,4-disubstituted imidazole derivative including a pharmaceutically acceptable salt thereof, and an anti-tumor agent comprising it as an active ingredient.

BACKGROUND ART

Conventional cancer treatments are sometimes not expected to bring in meaningful survival effects even if they can induce the regression of tumors, because of the persistent proliferation of malignant tumors, the metastasis or recurrence of cancer, and the resistance to anti-tumor agents. These days, it has been suggested that cancer stem cell (hereinafter referred to as "CSC") is one of the causes of the failure, which is closely involved in the factors such as the persistent proliferation of malignant tumor. CSCs have been identified in almost all types of major cancers in human such as breast cancer, colon cancer, lung cancer, and hematological malignancy (Non-Patent Document 1). Also, CSCs can be greatly different in the biological feature from normal cancer cells which differentiate from CSCs, and thus the development of an anti-tumor agent whose target is CSCs is expected to lead to a new strategy for cancer treatments (Non-Patent Document 2).

One of the features in CSCs is the self-renewal ability (Non-Patent Document 3). Reliable methods established for measuring the self-renewal ability of cells include, for example, a method for measuring the sphere-forming ability of cancer cells in non-adherent condition in the absence of serum (Non-Patent Document 4).

Non-Patent Document 5 discloses that PF-03084014 having an N-imidazolylamide scaffold can inhibit CSCs to exhibit an anti-cancer effect. However, Non-Patent Document 5 does not disclose the compound of formula (1') of the present invention.

PRIOR ART DOCUMENTS

Non-Patent Documents

Non-Patent Document 1: Boman et al., Journal of Clinical Oncology 26(17): 2795-2799. 2008
Non-Patent Document 2: Lobo et al., Annu Rev Cell Dev Biol 23: 675-99. 2007
Non-Patent Document 3: Al-Hajj et al., Oncogene 23(43): 7274-82. 2004
Non-Patent Document 4: Ponti et al., Cancer Res 65(13): 5506-11. 2005
Non-Patent Document 5: Zhang et al., Stem Cells Translational Medicine 2: 233-242. 2013

SUMMARY OF INVENTION

Problem to be Solved by the Invention

An object of the present invention is to provide a novel anti-tumor agent whose target is CSCs which are thought to be closely involved in the persistent proliferation of malignant tumor, the metastasis or recurrence of cancer, and the resistance to anti-tumor agents.

Means for Solving the Problems

The present inventors have extensively studied to reach the above object, and then have found that a compound of the following formula (1') or a pharmaceutically acceptable salt thereof (hereinafter referred to as "the present compound", as necessary) has a potent inhibitory effect on the sphere-forming ability of cancer cells and is highly useful as a novel anti-tumor agent. Based upon the new findings, the present invention has been completed.

The present invention provides inventions described below.

[1] A compound of formula (1'):

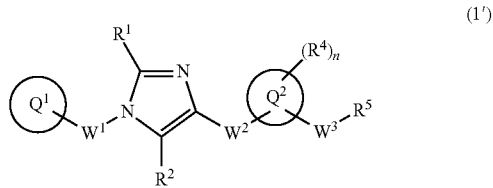

(1')

or a pharmaceutically acceptable salt thereof, wherein ring $Q^1$ is optionally-substituted $C_{6-10}$ aryl group, optionally-substituted. $C_{3-10}$ cycloalkyl group, or optionally-substituted 5- to 10-membered heteroaryl group;

$R^1$ and $R^2$ are independently hydrogen atom, halogen atom, or alkyl group which may be optionally substituted with the same or different 1 to 3 halogen atoms;

$W^1$ is optionally-substituted $C_{1-4}$ alkylene group;

$W^2$-$Q^2$ is —$NR^{3a}C(O)$-$Q^2$, —$NR^{3a}C(O)O$-$Q^2$, —$NR^{3a}C(O)OCH_2$-$Q^2$, —$NR^{3a}C(O)NR^{3b}$-$Q^2$, —$NR^{3a}C(O)NR^{3b}CH_2$-$Q^2$, —$NR^{3a}C(O)CH_2O$-$Q^2$, —$NR^{3a}C(O)CH_2$-$Q^2$, —$NR^{3a}C(O)CH_2CH_2$-$Q^2$, —$C(O)NR^{3a}$-$Q^2$, —$C(O)NR^{3a}CH_2$-$Q^2$, —$C(O)NR^{3a}CH_2CH_2$-$Q^2$, or —$NR^{3a}C(O)$-$CR^{3c}$=$CR^{3d}$-$Q^2$ wherein $R^{3a}$ and $R^{3b}$ are independently hydrogen atom or $C_{1-6}$ alkyl group; and $R^{3c}$ and $R^{3d}$ are independently hydrogen atom, fluorine atom, or $C_{1-6}$ alkyl group;

ring $Q^2$ is 5- to 10-membered heteroaryl group;

$W^3$ is optionally-substituted $C_{1-4}$ alkylene group, optionally-substituted. $C_{3-4}$ alkenylene group, or optionally-substituted $C_{3-4}$ alkynylene group;

n is 1, 2, 3, 4, or 5;

$R^4$ is, independently when two or more exist, hydrogen atom, halogen atom, optionally-substituted $C_{1-6}$ alkyl group, optionally-substituted $C_{1-6}$ alkoxy group, optionally-substituted $C_{3-10}$ cycloalkyl group, optionally-substituted. $C_{2-6}$ alkenyl group, optionally-substituted $C_{2-6}$ alkynyl group, cyano group, optionally-substituted $C_{1-6}$ alkyl-carbonyl group, optionally-substituted $C_{1-6}$ alkylsulfonyl group, optionally-substituted $C_{1-6}$ alkoxy-carbonyl group, optionally-substituted $C_{1-6}$ alkyl-carbonylamino group, optionally-substituted $C_{1-6}$ alkylsulfonylamino group, optionally-substituted $C_{1-6}$ alkoxy-carbonylamino group, optionally-substituted $C_{1-6}$ alkyl-carbonyloxy group, optionally-substituted amino group, optionally-substituted aminocarbonyl group, optionally-substituted aminosulfonyl group, optionally-substituted 5- or 6-membered cyclic amino group, optionally-substituted 5- or 6-membered cyclic aminocarbonyl group, nitro group, or carboxyl group;

when $R^4$ and $W^3$ are attached to the adjacent carbon atoms on ring $Q^2$, they may be combined with the carbon atoms to form 5- to 8-membered cycloalkane ring; and $R^5$ is (1) hydroxy group, (2) $C_{1-6}$ alkoxy group which may be optionally substituted with the same or different 1 to 3 groups independently selected from the group consisting of halogen atom, hydroxy, $C_{1-6}$ alkoxy, and $C_{6-10}$ aryl which may be optionally substituted with the same or different 1 to 4 groups independently selected from the group consisting of halogen atom, $C_{1-6}$ alkyl, and $C_{1-6}$ alkoxy, (3) amino group which may be optionally substituted with the same or different 1 to 2 $C_{1-6}$ alkyl groups, or (4) $C_{1-6}$ alkyl-carbonylamino group wherein the alkyl moiety thereof may be optionally substituted with the same or different 1 to 3 halogen atoms.

[2] A compound of formula (1):

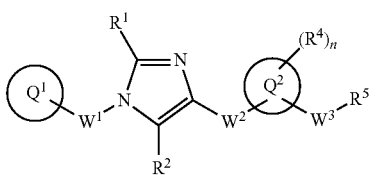

(1)

or a pharmaceutically acceptable salt thereof, wherein ring $Q^1$ is optionally-substituted $C_{6-10}$ aryl group, optionally-substituted $C_{3-10}$ cycloalkyl group, or optionally-substituted 5- to 10-membered heteroaryl group;

$R^1$ and $R^2$ are independently hydrogen atom, halogen atom, or $C_{1-6}$ alkyl group which may be optionally substituted with the same or different 1 to 3 halogen atoms;

$W^1$ is optionally-substituted $C_{1-4}$ alkylene group;

$W^2$-$Q^2$ is —$NR^{3a}C(O)$-$Q^2$, —$NR^{3a}C(O)O$-$Q^2$, —$NR^{3a}C(O)OCH_2$-$Q^2$, —$NR^{3a}C(O)NR^{3b}$-$Q^2$, —$NR^{3a}C(O)NR^{3b}CH_2$-$Q^2$, —$NR^{3a}C(O)CH_2O$-$Q^2$, —$NR^{3a}C(O)CH_2$-$Q^2$, —$NR^{3a}C(O)CH_2CH_2$-$Q^2$, —$C(O)NR^{3a}$-$Q^2$, —$C(O)NR^{3a}CH_2$-$Q^2$, or —$C(O)NR^{3a}CH_2CH_2$-$Q^2$, wherein $R^{3a}$ and $R^{3b}$ are independently hydrogen atom or $C_{1-6}$ alkyl group;

ring $Q^2$ is 5- to 10-membered heteroaryl group;

$W^3$ is optionally-substituted $C_{1-4}$ alkylene group, optionally-substituted $C_{3-4}$ alkenylene group, or optionally-substituted $C_{3-4}$ alkynylene group;

n is 1, 2, 3, 4, or 5;

$R^4$ is, independently when two or more exist, hydrogen atom, halogen atom, optionally-substituted. $C_{1-6}$ alkyl group, optionally-substituted $C_{1-6}$ alkoxy group, optionally-substituted $C_{3-10}$ cycloalkyl group, optionally-substituted $C_{2-6}$ alkenyl group, optionally-substituted $C_{2-6}$ alkynyl group, cyano group, or optionally-substituted amino group;

when $R^4$ and $W^3$ are attached to the adjacent carbon atoms on ring $Q^2$, they may be combined with the carbon atoms to form 5- to 8-membered cycloalkane ring; and $R^5$ is (1) hydroxy group, (2) $C_{1-6}$ alkoxy group which may be optionally substituted with the same or different 1 to 3 groups independently selected from the group consisting of halogen atom, hydroxy, $C_{1-6}$ alkoxy, and $C_{6-10}$ aryl which may be optionally substituted with the same or different 1 to 4 groups independently selected from the group consisting of halogen atom, $C_{1-6}$ alkyl, and $C_{1-6}$ alkoxy, (3) amino group which may be optionally substituted with the same or different 1 to 2 $C_{1-6}$ alkyl groups, or (4) $C_{1-6}$ alkyl-carbonylamino group wherein the alkyl moiety thereof may be optionally substituted with the same or different 1 to 3 halogen atoms.

[3] The compound according to [1] or [2] or a pharmaceutically acceptable salt thereof wherein ring $Q^1$ is (1) $C_{6-10}$ aryl group which may be optionally substituted with the same or different 1 to 5 groups independently selected from the group consisting of (a) halogen atom, (b) $C_{1-6}$ alkyl which may be optionally substituted with the same or different 1 to 3 groups independently selected from the group consisting of halogen atom, hydroxy, and $C_{1-6}$ alkoxy, (c) $C_{1-6}$ alkoxy which may be optionally substituted with the same or different 1 to 3 groups independently selected from the group consisting of halogen atom, hydroxy, and $C_{1-6}$ alkoxy, (d) cyano, (e) $C_{6-10}$ aryl which may be optionally substituted with the same or different 1 to 4 groups independently selected from the group consisting of halogen atom, $C_{1-6}$ alkyl, and $C_{1-6}$ alkoxy, (f) 5- or 6-membered heteroaryl which may be optionally substituted with the same or different 1 to 4 groups independently selected from the group consisting of halogen atom, $C_{1-6}$, alkyl, and $C_{1-6}$ alkoxy, (g) $C_{6-10}$ aryloxy which may be optionally substituted with the same or different 1 to 4 groups independently selected from the group consisting of halogen atom, $C_{1-6}$ alkyl, and $C_{1-6}$ alkoxy, (h) hydroxy, (i) amino which may be optionally substituted with the same or different 1 to 2 $C_{1-6}$ alkyl groups, (j) aminocarbonyl wherein the amino moiety thereof may be optionally substituted with the same or different 1 to 2 $C_{1-6}$ alkyl groups, (k) $C_{1-6}$ alkoxycarbonyl wherein the alkoxy moiety thereof may be optionally substituted with the same or different 1 to 3 groups independently selected from the group consisting of halogen atom, hydroxy, and $C_{1-6}$ alkoxy, (l) $C_{1-6}$ alkyl-carbonyl wherein the alkyl moiety thereof may be optionally substituted with the same or different 1 to 3 groups independently selected from the group consisting of halogen atom, hydroxy, and $C_{1-6}$ alkoxy, (m) $C_{1-6}$ alkylsulfonyl wherein the alkyl moiety thereof may be optionally substituted with the same or different 1 to 3 groups independently selected from the group consisting of halogen atom, hydroxy, and $C_{1-6}$ alkoxy, (n) $C_{1-6}$ alkyl-carbonylamino wherein the alkyl moiety thereof may be optionally substituted with the same or different 1 to 3 groups independently selected from the group consisting of halogen atom, hydroxy, and $C_{1-6}$ alkoxy, (o) $C_{1-6}$ alkylsulfonylamino wherein the alkyl moiety thereof may be optionally substituted with the same or different 1 to 3 groups independently selected from the group consisting of halogen atom, hydroxy, and $C_{1-6}$ alkoxy, (p) $C_{1-6}$ alkoxy-carbonylamino wherein the alkoxy moiety thereof may be optionally substituted with the same or different 1 to 3 groups independently selected from the group consisting of halogen atom, hydroxy, and $C_{1-6}$ alkoxy, (q) $C_{1-6}$ alkyl-carbonyloxy wherein the alkyl moiety thereof may be optionally substituted with the same or different 1 to 3 groups independently selected from the group consisting of halogen atom, hydroxy, and $C_{1-6}$ alkoxy, (r) aminosulfonyl wherein the amino moiety thereof may be optionally substituted with the same or different 1 to 2 $C_{1-6}$ alkyl groups, and (s) $C_{3-10}$ cycloalkyl which may be optionally substituted with the same or different 1 to 4 groups independently selected from the group consisting of halogen atom, hydroxy, and $C_{1-6}$ alkoxy, (2) $C_{3-10}$ cycloalkyl group which may be optionally substituted with the same or different 1 to 5 groups independently selected from the group consisting of (a) to (s) defined is the above (1), or (3) 5- to 10-membered heteroaryl group which may be optionally substituted with the same or different 1 to 5 groups independently selected from the group consisting of (a) to (s) defined in the above (1);

$W^1$ is $C_{1-4}$ alkylene group which may be optionally substituted with the same or different 1 to 4 groups independently selected from the group consisting of halogen atom, hydroxy, and $C_{1-6}$ alkoxy;

$W^3$ is (1) $C_{1-4}$ alkylene group which may be optionally substituted with the same or different 1 to 4 groups independently selected from the group consisting of halogen atom, hydroxy, and $C_{1-6}$ alkoxy, (2) $C_{3-4}$ alkenylene group which may be optionally substituted with the same or different 1 to 2 halogen atoms, or (3) $C_{3-4}$ alkynylene group which may be optionally substituted with the same or different 1 to 2 halogen atoms; and $R^4$ is, independently when two or more exist, (1) hydrogen atom, (2) halogen atom, (3) $C_{1-6}$ alkyl group which may be optionally substituted with the same or different 1 to 3 groups independently selected from the group consisting of halogen atom, hydroxy, and $C_{1-6}$ alkoxy, (4) $C_{1-6}$ alkoxy group which may be optionally substituted with the same or different 1 to 3 groups independently selected from the group consisting of halogen atom, hydroxy, and $C_{1-6}$ alkoxy, (5) $C_{3-10}$ cycloalkyl group which may be optionally substituted with the same or different 1 to 4 groups independently selected from the group consisting of halogen atom, hydroxy, and $C_{1-6}$ alkoxy, (6) $C_{2-6}$ alkenyl group which may be optionally substituted with the same or different 1 to 2 halogen atoms, (7) $C_{2-6}$ alkynyl group which may be optionally substituted with the same or different 1 to 2 halogen atoms, (8) cyano group, or (9) amino group which may be optionally substituted with the same or different 1 to 2 $C_{1-6}$ alkyl groups;

when $R^4$ and $W^3$ are attached to the adjacent carbon atoms on ring $Q^2$, they may combined with the carbon atoms to form 5- to 8-membered cycloalkane ring.

[4] The compound according to any one of [1] to [3] or a pharmaceutically acceptable salt thereof wherein ring $Q^1$ is (1) phenyl group which may be optionally substituted with the same or different 1 to 5 groups independently selected from the group consisting of (a) halogen atom, (b) $C_{1-6}$ alkyl which may be optionally substituted with the same or different 1 to 3 groups independently selected from the group consisting of halogen atom, hydroxy, and $C_{1-6}$ alkoxy, (c) $C_{1-6}$ alkoxy which may be optionally substituted with the same or different 1 to 3 groups independently selected from the group consisting of halogen atom, hydroxy, and $C_{1-6}$ alkoxy, (d) cyano, (e) phenyl which may be optionally substituted with the same or different 1 to 4 groups independently selected from the group consisting of halogen atom, $C_{1-6}$ alkyl, and $C_{1-6}$ alkoxy, (f) 5- or 6-membered heteroaryl which may be optionally substituted with the same or different 1 to 4 groups independently selected from the group consisting of halogen atom, $C_{1-6}$ alkyl, and $C_{1-6}$ alkoxy, and (g) phenoxy which may be optionally substituted with the same or different 1 to 4 groups independently selected from the group consisting of halogen atom, $C_{1-6}$ alkyl, and $C_{1-6}$ alkoxy, (2) $C_{3-7}$ cycloalkyl group which may be optionally substituted with the same or different 1 to 4 groups independently selected from the group consisting of (a) to (g) defined in the above (1), or (3) pyridyl group which may be optionally substituted with the same or different 1 to 4 groups independently selected from the group consisting of (a) to (g) defined in the above (1).

[5] The compound according to any one of [1] to [4] or a pharmaceutically acceptable salt thereof wherein ring $Q^1$ is phenyl group which may be optionally substituted with the same or different 1 to 5 groups independently selected from the group consisting of (a) halogen atom, (b) alkyl which may be optionally substituted with the same or different 1 to 3 halogen atoms, and (c) $C_{1-6}$ alkoxy which may be optionally substituted with the same or different 1 to 3 halogen atoms.

[6] The compound according to any one of [1] to [5] or a pharmaceutically acceptable salt thereof wherein $W^1$ is methylene group which may be optionally substituted with the same or different 1 to 2 halogen atoms, or ethylene group which may be optionally substituted with the same or different 1 to 4 halogen atoms.

[7] The compound according to any one of [1] to [6] or a pharmaceutically acceptable salt thereof wherein $W^2$-$Q^2$ is —$NR^{3a}C(O)$-$Q^2$, —$NR^{3a}C(O)CH_2O$-$Q^2$, or —$C(O)NR^{3a}$-$Q^2$ wherein $R^{3a}$ is hydrogen atom or $C_{1-6}$ alkyl group.

[8] The compound according to any one of [1] to [7] or a pharmaceutically acceptable salt thereof wherein $W^2$-$Q^2$ is —NHC(O)-$Q^2$ or —C(O)NH-$Q^2$.

[9] The compound according to any one of [1] to [8] or a pharmaceutically acceptable salt thereof wherein ring $Q^2$ is pyridyl group, pyrimidyl group, pyridazyl group, pyrazyl group, oxazolyl group, thiazolyl group, isoxazolyl group, isothiazolyl group, quinolinyl group, isoquinolinyl group, quinazolinyl group, or quinoxalinyl group.

[10] The compound according to any one of [1] to [9] or a pharmaceutically acceptable salt thereof wherein ring $Q^2$ is pyridyl group, pyridazyl group, pyrazyl group, oxazolyl group, thiazolyl group, isoxazolyl group, or quinolinyl group.

[11] The compound according to any one of [1] to [10] or a pharmaceutically acceptable salt thereof wherein $W^3$ is methylene group which may be optionally substituted with the same or different 1 to 2 halogen atoms, or ethylene group which may be optionally substituted with the same different 1 to 4 groups independently selected from the group consisting of halogen atom, hydroxy, and $C_{1-6}$ alkoxy; and $R^5$ is hydroxy group, or $C_{1-6}$ alkoxy group which may be optionally substituted with the same or different 1 to 3 groups independently selected from the group consisting of halogen atom, hydroxy, and $C_{1-6}$ alkoxy.

[12] The compound according to claim 1 which is represented by formula (1a'):

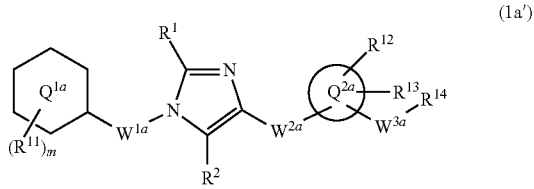

(1a')

or a pharmaceutically acceptable salt thereof, wherein ring $Q^{1a}$ is phenyl group, pyridyl group, or cyclohexyl group;

m is 1, 2, 3, 4, or 5;

$R^{11}$ is, independently when two or more exist,
(1) hydrogen atom,
(2) halogen atom,
(3) $C_{1-6}$ alkyl group which may be optionally substituted with the same or different 1 to 3 halogen atoms, or
(4) $C_{1-6}$ alkoxy group which may be optionally substituted with the same or different 1 to 3 halogen atoms;

$R^1$ and $R^2$ are independently hydrogen atom, halogen atom, or $C_{1-6}$ alkyl group which may be optionally substituted with the same or different 1 to 3 halogen atoms;

$W^{1a}$ is methylene group which may be optionally substituted with the same or different 1 to 2 halogen atoms, or ethylene group which may be optionally substituted with the same or different 1 to 4 halogen atoms;

$W^{2a}$-$Q^{2a}$ is —$NR^{3a}C(O)$-$Q^{2a}$, —$NR^{3a}C(O)CH_2O$-$Q^{2a}$, —$C(O)NR^{3a}$-$Q^{2a}$, or —$NR^{3a}C(O)$-$CH$=$CH$-$Q^{2a}$ wherein $R^{3a}$ is hydrogen atom or $C_{1-6}$ alkyl group;

ring $Q^{2a}$ is 5- or 6-membered heteroaryl group;

$W^{3a}$ is methylene group which may be optionally substituted with the same or different 1 to 2 halogen atoms, or ethylene group which may be optionally substituted with the same or different 1 to 4 groups independently selected from the group consisting of halogen atom, hydroxy, and $C_{1-6}$ alkoxy;

$R^{12}$ and $R^{13}$ are independently
(1) hydrogen atom,
(2) halogen atom,
(3) $C_{1-6}$ alkyl group which may be optionally substituted with the same or different 1 to 3 groups independently selected from the group consisting of halogen atom, hydroxy, and $C_{1-6}$ alkoxy,
(4) $C_{1-6}$ alkoxy group which may be optionally substituted with the same or different 1 to 3 groups independently selected from the group consisting of halogen atom, hydroxy, and $C_{1-6}$ alkoxy,
(5) $C_{3-10}$ cycloalkyl group which may be optionally substituted with the same or different 1 to 4 groups independently selected from the group consisting of halogen atom, hydroxy, and $C_{1-6}$ alkoxy,
(6) $C_{2-6}$ alkenyl group which may be optionally substituted with the same or different 1 to 2 halogen atoms,
(7) $C_{2-6}$ alkynyl group which may be optionally substituted with the same or different 1 to 2 halogen atoms,
(8) cyano group, or
(9) amino group which may be optionally substituted with the same or different 1 to 2 $C_{1-6}$ alkyl groups;

when $R^{13}$ and $W^{3a}$ are attached to the adjacent carbon atoms on ring $Q^2$, they may combined with the carbon atoms to form 5- or 6-membered cycloalkane ring; and $R^{14}$ is hydroxy group, or $C_{1-6}$ alkoxy group which may be optionally substituted with the same or different 1 to 3 groups independently selected from the group consisting of halogen atom, hydroxy, and $C_{1-6}$ alkoxy.

[13] The compound according to claim 1 which is represented by formula (1a):

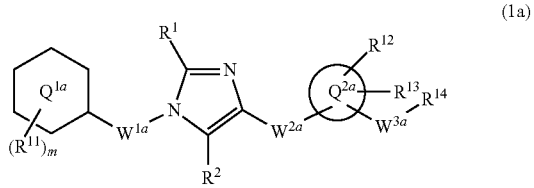

(1a)

or a pharmaceutically acceptable salt thereof, wherein ring $Q^{1a}$ is phenyl group, pyridyl group, or cyclohexyl group;

m is 1, 2, 3, 4, or 5;

$R^{11}$ is, independently when two or more exist,
(1) hydrogen atom,
(2) halogen atom,
(3) $C_{1-6}$ alkyl group which may be optionally substituted with the same or different 1 to 3 halogen atoms, or
(4) $C_{1-6}$ alkoxy group which may be optionally substituted with the same or different 1 to 3 halogen atoms;

$R^1$ and $R^2$ are independently hydrogen atom, halogen atom, or $C_{1-6}$ alkyl group which may be optionally substituted with the same or different 1 to 3 halogen atoms;

$W^{1a}$ is methylene group which may be optionally substituted with the same or different 1 to 2 halogen atoms, or ethylene group which may be optionally substituted with the same or different 1 to 4 halogen atoms;

$W^{2a}$-$Q^{2a}$ is —$NR^{3a}C(O)$-$Q^{2a}$, —$NR^{3a}C(O)CH_2O$-$Q^{2a}$, or —$C(O)NR^{3a}$-$Q^{2a}$ wherein $R^{3a}$ is hydrogen atom or $C_{1-6}$ alkyl group;

ring $Q^{2a}$ is 5- or 6-membered heteroaryl group;

$W^{3a}$ is methylene group which may be optionally substituted with the same or different 1 to 2 halogen atoms, or ethylene group which may be optionally substituted with the same or different 1 to 4 groups independently selected from the group consisting of halogen atom, hydroxy, and $C_{1-6}$ alkoxy;

$R^{12}$ and $R^{13}$ are independently
(1) hydrogen atom,
(2) halogen atom,
(3) $C_{1-6}$ alkyl group which may be optionally substituted with the same or different 1 to 3 groups independently selected from the group consisting of halogen atom, hydroxy, and $C_{1-6}$ alkoxy,
(4) $C_{1-6}$ alkoxy group which may be optionally substituted with the same or different 1 to 3 groups independently selected from the group consisting of halogen atom, hydroxy, and $C_{1-6}$ alkoxy,
(5) $C_{3-10}$ cycloalkyl group which may be optionally substituted with the same or different 1 to 4 groups independently selected from the group consisting of halogen atom, hydroxy, and $C_{1-6}$ alkoxy,
(6) $C_{2-6}$ alkenyl group which may be optionally substituted with the same or different 1 to 2 halogen atoms,
(7) $C_{2-6}$ alkynyl group which may be optionally substituted with the same or different 1 to 2 halogen atoms,
(8) cyano group, or (9) amino group which may be optionally substituted with the same or different 1 to 2 $C_{1-6}$ alkyl groups;

when $R^{13}$ and $W^{3a}$ are attached to the adjacent carbon atoms on ring $Q^{2a}$, they may be combined with the carbon atoms to form 5- or 6-membered cycloalkane ring; and $R^{14}$ is hydroxy group, or $C_{1-6}$ alkoxy group which may be optionally substituted with the same or different 1 to 3 groups independently selected from the group consisting of halogen atom, hydroxy, and $C_{1-6}$ alkoxy.

[14] The compound according to [12] or [13] or a pharmaceutically acceptable salt thereof wherein ring $Q^{1a}$ is phenyl group.

[15] The compound according to any one of [12] to [14] or a pharmaceutically acceptable salt thereof wherein $W^{2a}$-$Q^{2a}$ is —NHC(O)-$Q^{2a}$.

[16] The compound according to any one of [12] to [14] or a pharmaceutically acceptable salt thereof wherein $W^{2a}$-$Q^{2a}$ is —C(O)NH-$Q^{2a}$.

[17] The compound according to any one of [12] to [16] or a pharmaceutically acceptable salt thereof wherein ring $Q^{2a}$ is pyridyl group, pyrimidyl group, pyridazyl group, pyrazyl group, oxazolyl group, thiazolyl group, isoxazolyl group, or isothiazolyl group.

[18] The compound according to any one of [12] to [16] or a pharmaceutically acceptable salt thereof wherein ring $Q^{2a}$ is pyridyl group, pyridazyl group, pyrazyl group, oxazolyl group, thiazolyl group, or isoxazolyl group.

[19] The compound according to any one of [12] to [16] or a pharmaceutically acceptable salt thereof wherein ring $Q^{2a}$ is pyridyl group.

[20] The compound according to any one of [12] to [19] or a pharmaceutically acceptable salt thereof wherein $R^{12}$ and $R^{13}$ are independently
(1) hydrogen atom,
(2) halogen atom,
(3) $C_{1-6}$ alkyl group which may be optionally substituted with the same or different 1 to 3 groups independently selected from the group consisting of halogen atom, hydroxy, and $C_{1-6}$ alkoxy,
(4) $C_{1-6}$ alkoxy group which may be optionally substituted with the same or different 1 to 3 groups independently selected from the group consisting of halogen atom, hydroxy, and $C_{1-6}$ alkoxy,
(5) $C_{2-6}$ alkenyl group which may be optionally substituted with the same or different 1 to 2 halogen atoms, or
(6) amino group which may be optionally substituted with the same or different 1 to 2 $C_{1-6}$ alkyl groups.

[21] The compound according to any one of [12] to [20] or a pharmaceutically acceptable salt thereof wherein $R^{12}$ and $R^{13}$ are independently
(1) hydrogen atom,
(2) halogen atom,
(3) $C_{1-6}$ alkyl group which may be optionally substituted with the same or different 1 to 3 groups independently selected from the group consisting of halogen atom, hydroxy, and $C_{1-6}$ alkoxy, or
(4) amino group.

[22] The compound according to any one of [12] to [21] or a pharmaceutically acceptable salt thereof wherein $R^{13}$ is halogen atom, $C_{1-6}$ alkyl group which may be optionally substituted with the same or different 1 to 3 halogen atoms, or amino group; and $R^{12}$ is hydrogen atom.

[23] The compound according to any one of [12] to [22] or a pharmaceutically acceptable salt thereof wherein $W^{3a}$ is methylene group which may be optionally substituted with the same or different 1 to 2 halogen atoms; and $R^{14}$ is hydroxy group.

[24] The compound according to any one of [1] to [23] or a pharmaceutically acceptable salt thereof wherein $R^1$ and $R^2$ are hydrogen atom.

[25] The compound according to [1] which is represented by formula (1b):

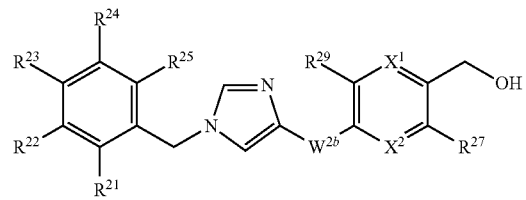

or a pharmaceutically acceptable salt thereof, wherein $X^1$ is N or $CR^{26}$;
$X^2$ is N or $CR^{28}$;
provide that at least one of $X^1$ and $X^2$ is N;
$R^{21}$, $R^{22}$, $R^{23}$, $R^{24}$, and $R^{25}$ are independently
(1) hydrogen atom,
(2) halogen atom,
(3) $C_{1-6}$ alkyl group which may be optionally substituted with the same or different 1 to 3 halogen atoms, or
(4) $C_{1-6}$ alkoxy group which may be optionally substituted with the same or different 1 to 3 halogen atoms;
$W^{2b}$ is —NHC(O)— or —C(O)NH—;
$R^{26}$, $R^{27}$, $R^{28}$, and $R^{29}$ are independently
(1) hydrogen atom,
(2) halogen atom,
(3) $C_{1-6}$ alkyl group which may be optionally substituted with the same or different 1 to 3 groups independently selected from the group consisting of halogen atom, hydroxy, and $C_{1-6}$ alkoxy,
(4) $C_{1-6}$ alkoxy group which may be optionally substituted with the same or different 1 to 3 groups independently selected from the group consisting of halogen atom, hydroxy, and $C_{1-6}$ alkoxy,
(5) $C_{2-6}$ alkenyl group which may be optionally substituted with the same or different 1 to 2 halogen atoms, or
(6) amino group which may be optionally substituted with the same or different 1 to 2 $C_{1-6}$ alkyl groups.

[26] The compound according to [25] or a pharmaceutically acceptable salt thereof wherein $R^{22}$ is halogen atom or $C_{1-6}$ alkyl group which may be optionally substituted with the same or different 1 to 3 halogen atoms.

[27] The compound according to [25] or a pharmaceutically acceptable salt thereof wherein $R^{22}$ is halogen atom or trifluoromethyl group.

[28] The compound according to any one of [25] to [27] or a pharmaceutically acceptable salt thereof wherein $R^{21}$, $R^{23}$, $R^{24}$, and $R^{25}$ are independently
(1) hydrogen atom,
(2) halogen atom, or
(3) $C_{1-6}$ alkyl group which may be optionally substituted with the same or different 1 to 3 halogen atoms.

[29] The compound according to any one of [25] to [28] or a pharmaceutically acceptable salt thereof wherein $W^{2b}$ is —NHC(O)—.

[30] The compound according to any one of [25] to [29] or a pharmaceutically acceptable salt thereof wherein $X^1$ is N.

[31] The compound according to any one of [25] to [30] or a pharmaceutically acceptable salt thereof wherein $X^1$ is N; and $X^2$ is CH.

[32] The compound according to any one of [25] to [31] or a pharmaceutically acceptable salt thereof wherein $R^{27}$ is halogen atom, $C_{1-6}$ alkyl group which may be optionally substituted with the same or different 1 to 3 halogen atoms, or amino group; and $R^{29}$ is hydrogen atom.

[33] The compound according to any one of [25] to [32] or a pharmaceutically acceptable salt thereof wherein $R^{27}$ is methyl group substituted with 1 to 3 fluorine atoms; and $R^{29}$ is hydrogen atom.

[34] The compound according to any one of [25] to [33] or a pharmaceutically acceptable salt thereof wherein $R^{27}$ is methyl group substituted with 2 fluorine atoms; and $R^{29}$ is hydrogen atom.

[35] The compound according to [1] which is represented by formula (1c):

or a pharmaceutically acceptable salt thereof, wherein $R^{32}$ is halogen atom or $C_{1-6}$ alkyl group which may be optionally substituted with the same or different 1 to 3 halogen atoms; and $R^{33}$ and $R^{34}$ are independently hydrogen atom, or halogen atom.

[36] The compound according to [35] or a pharmaceutically acceptable salt thereof wherein $R^{32}$ is fluorine atom, chlorine atom, or trifluoromethyl group.

[37] The compound according to [1] selected from the following compounds or a pharmaceutically acceptable salt thereof:

6-(hydroxymethyl)-N-[1-(3,4,5-trifluorobenzyl)-1H-imidazol-4-yl]nicotinamide (Example 10), 6-(hydroxymethyl)-N-{1-[3-(trifluoromethyl)benzyl]-1H-imidazol-4-yl}nicotinamide (Example 12), 5-(difluoromethyl)-6-(hydroxymethyl)-N-{1-[3-(trifluoromethyl)benzyl]-1H-imidazol-4-yl}nicotinamide (Example 17), 5-(difluoromethyl)-6-(hydroxymethyl)-N-[1-(3,4,5-trifluorobenzyl)-1H-imidazol-4-yl]nicotinamide (Example 18), 6-(hydroxymethyl)-5-(trifluoromethyl)-N-{1-[3-(trifluoromethyl)benzyl]-1H-imidazol-4-yl}nicotinamide (Example 19), 6-(hydroxymethyl)-5-methyl-N-[1-(3,4,5-trifluorobenzyl)-1H-imidazol-4-yl]nicotinamide (Example 39), 6-(hydroxymethyl)-5-methyl-N-{1-[3-(trifluoromethyl)benzyl]-1H-imidazol-4-yl}nicotinamide (Example 42), 5-amino-6-(hydroxymethyl)-N-{1-[3-(trifluoromethyl)benzyl]-1H-imidazol-4-yl}nicotinamide (Example 45), 5-amino-6-(hydroxymethyl)-N-[1-(3,4,5-trifluorobenzyl)-1H-imidazol-4-yl]nicotinamide (Example 46), N-[1-(3,4-difluorobenzyl)-1H-imidazol-4-yl]-5-(difluoromethyl)-6-(hydroxymethyl)nicotinamide (Example 54), N-[1-(3-chlorobenzyl)-1H-imidazol-4-yl]-5-(difluoromethyl)-6-(hydroxymethyl)nicotinamide (Example 55), 5-(difluoromethyl)-N-{1-[4-fluoro-3-(trifluoromethyl)benzyl]-1H-imidazol-4-yl}-6-(hydroxymethyl)nicotinamide (Example 57), 5-(difluoromethyl)-N-{1-[3-fluoro-5-(trifluoromethyl)benzyl]-1H-imidazol-4-yl}-6-(hydroxymethyl)nicotinamide (Example 60), N-[1-(3-chloro-4-fluorobenzyl)-1H-imidazol-4-yl]-5-(difluoromethyl)-6-(hydroxymethyl)nicotinamide (Example 61), N-[1-(3-bromo-4-fluorobenzyl)-1H-imidazol-4-yl]-5-(difluoromethyl)-6-(hydroxymethyl)nicotinamide (Example 62), 5-(difluoromethyl)-6-(hydroxymethyl)-N-{1-[3-methoxy-5-(trifluoromethyl)benzyl]-1H-imidazol-4-yl}nicotinamide (Example 65), 5-(difluoromethyl)-6-(hydroxymethyl)-N-{1-[4-methyl-3-(trifluoromethyl)benzyl]-1H-imidazol-4-yl}nicotinamide (Example 70), N-[1-(3,4-dichlorobenzyl)-1H-imidazol-4-yl]-5-(difluoromethyl)-6-(hydroxymethyl)nicotinamide (Example 71), N-[1-(3,5-dichlorobenzyl)-1H-imidazol-4-yl]-5-(difluoromethyl)-6-(hydroxymethyl)nicotinamide (Example 75), N-[1-(3-bromo-5-fluorobenzyl)-1H-imidazol-4-yl]-5-(difluoromethyl)-6-(hydroxymethyl)nicotinamide (Example 76), N-[1-(3-chloro-5-fluorobenzyl)-1H-imidazol-4-yl]-5-(difluoromethyl)-6-(hydroxymethyl)nicotinamide (Example 78), N-[1-(3,5-difluorobenzyl)-1H-imidazol-4-yl]-5-(difluoromethyl)-6-(hydroxymethyl)nicotinamide (Example 79), and 6-(hydroxymethyl)-N-[1-(3,4,5-trifluorobenzyl)-1H-imidazol-4-yl]pyridazine-3-carboxamide (Example 35).

[38] The compound according to [1] selected from the following comppounds or a pharmaceutically acceptable salt thereof:

5-(difluoromethyl)-6-(hydroxymethyl)-N-{1-[3-(trifluoromethyl)benzyl]-1H-imidazol-4-yl}nicotinamide (Example 17), 5-(difluoromethyl)-6-(hydroxymethyl)-N-[1-(3,4,5-trifluorobenzyl)-1H-imidazol-4-yl]nicotinamide (Example 13), N-[1-(3,4-difluorobenzyl)-1H-imidazol-4-yl]-5-(difluoromethyl)-6-(hydroxymethyl)nicotinamide (Example 54), N-[1-(3-chlorobenzyl)-1H-imidazol-4-yl]-5-(difluoromethyl)-6-(hydroxymethyl)nicotinamide (Example 55), 5-(difluoromethyl)-N-{1-[4-fluoro-3-(trifluoromethyl)benzyl]-1H-imidazol-4-yl}-6-(hydroxymethyl)nicotinamide (Example 57), N-[1-(3-bromobenzyl)-1H-imidazol-4-yl]-5-(difluoromethyl)-6-(hydroxymethyl)nicotinamide (Example 58), 5-(difluoromethyl)-N-{1-[3-fluoro-5-(trifluoromethyl)benzyl]-1H-imidazol-4-yl}-6-(hydroxymethyl)nicotinamide (Example 60), N-[1-(3-chloro-4-fluorobenzyl)-1H-imidazol-4-yl]-5-(difluoromethyl)-6-(hydroxymethyl)nicotinamide (Example 61), N-[1-(3-bromo-4-fluorobenzyl)-1H-imidazol-4-yl]-5-(difluoromethyl)-6-(hydroxymethyl)nicotinamide (Example 62), 5-(difluoromethyl)-6-(hydroxymethyl)-N-[1-(3-methylbenzyl)-1H-imidazol-4-yl]nicotinamide (Example 63), 5-(difluoromethyl)-6-(hydroxymethyl)-N-{1-[3-methoxy-5-(trifluoromethyl)benzyl]-1H-imidazol-4-yl}nicotinamide (Example 65), N-[1-(4-chloro-3-fluorobenzyl)-1H-imidazol-4-yl]-5-(difluoromethyl)-6-(hydroxymethyl)nicotinamide (Example 66), N-[1-(4-bromo-3-fluorobenzyl)-1H-imidazol-4-yl]-5-(difluoromethyl)-6-(hydroxymethyl)nicotinamide (Example 67), 5-(difluoromethyl)-6-(hydroxymethyl)-N-{1-[4-methyl-3-(trifluoromethyl)benzyl]-1H-imidazol-4-yl}nicotinamide (Example 70), N-[1-(3,4-dichlorobenzyl)-1H-imidazol-4-yl]-5-(difluoromethyl)-6-(hydroxymethyl)nicotinamide (Example 71), 5-(difluoromethyl)-N-{1-[3-fluoro-4-(trifluoromethyl)benzyl]-1H-imidazol-4-yl}-6-(hydroxymethyl)nicotinamide (Example 74), N-[1-(3,5-dichlorobenzyl)-1H-imidazol-4-yl]-5-(difluoromethyl)-6-(hydroxymethyl)nicotinamide (Example 75), N-[1-(3-bromo-5-fluorobenzyl)-1H-imidazol-4-yl]-5-(difluoromethyl)-6-(hydroxymethyl)nicotinamide (Example 76), N-[1-(3-chloro-5-fluorobenzyl)-1H-imidazol-4-yl]-5-(difluoromethyl)-6-(hydroxymethyl)nicotinamide (Example 78), N-[1-(3,5-difluorobenzyl)-1H-imidazol-4-yl]-5-(difluoromethyl)-6-(hydroxymethyl)nicotinamide (Example 79), and N-[1-(3-bromo-4-chlorobenzyl)-1H-imidazol-4-yl]-5-(difluoromethyl)-6-(hydroxymethyl)nicotinamide (Example 80).

[39] The compound accroding to [1] selected from the following compounds or a pharmaceuticaiiy acceptable salt thereof:

6-(hydroxymethyl)-N-{1-[3-(trifluoromethyl)benzyl]-1H-imidazol-4-yl}nicotinamide (Example 12), 5-(difluoromethyl)-6-(hydroxymethyl)-N-{1-[3-(trifluoromethyl)benzyl]-1H-imidazol-4-yl}nicotinamide (Example 17), 5-(difluoromethyl)-6-(hydroxymethyl)-N-[1-(3,4,5-trifluorobenzyl)-1H-imidazol-4-yl]nicotinamide (Example 18), 6-(hydroxymethyl)-5-methyl-N-[1-(3,4,5-trifluorobenzyl)-1H-imidazol-4-yl]nicotinamide (Example 39), 5-amino-6-(hydroxymethyl)-N-{1-[3-(trifluoromethyl)benzyl]-1H-imidazol-4-yl}nicotinamide (Example 45), 5-amino-6-(hydroxymethyl)-N-[1-(3,4,5-trifluorobenzyl)-1H-imidazol-4-yl]nicotinamide (Example 46), 5-(difluoromethyl)-N-{1-[4-fluoro-3-(trifluoromethyl)benzyl]-1H-imidazol-4-yl}-6-(hydroxymethyl)nicotinamide (Example 57), 5-(difluoromethyl)-N-{1-[3-fluoro-5-(trifluoromethyl)benzyl]-1H-imidazol-4-yl}-6-(hydroxymethyl)nicotinamide (Example 60), N-[1-(3-chloro-4-fluorobenzyl)-1H-imidazol-4-yl]-5-(difluoromethyl)-6-(hydroxymethyl)nicotinamide (Example 61), N-[1-(3-bromo-4-fluorobenzyl)-1H-imidazol-4-yl]-5-(difluoromethyl)-6-(hydroxymethyl)nicotinamide (Example 62), 5-(difluoromethyl)-6-(hydroxymethyl)-N-{1-[4-methyl-3-(trifluoromethyl)benzyl]-1H-imidazol-4-yl}nicotinamide (Example 70), N-[1-(3,4-dichlorobenzyl)-1H-imidazol-4-yl]-5-(difluoromethyl)-6-(hydroxymethyl)nicotinamide (Example 71), N-[1-(3,5-dichlorobenzyl)-1H-imidazol-4-yl]-5-(difluoromethyl)-6-(hydroxymethyl)nicotinamide (Example 75), N-[1-(3-bromo-5-fluorobenzyl)-1H-imidazol-4-yl]-5-(difluoromethyl)-6-(hydroxymethyl)nicotinamide (Example 76), N-[1-(3-chloro-5-fluorobenzyl)-1H-imidazol-4-yl]-5-(difluoromethyl)-6-(hydroxymethyl)nicotinamide (Example 78), and N-[1-(3,5-difluorobenzyl)-1H-imidazol-4-yl]-5-(difluoromethyl)-6-(hydroxymethyl) nicotinamide (Example 79).

[40] A medicament comprising the compound according to any one of [1] to [39] or a pharmaceutically acceptable salt thereof as an active ingredient.

An anti-tumor agent comprising the compound according to any one of [1] to [39] or a pharmaceutically acceptable salt thereof as an active ingredient.

[42] The anti-tumor agent according to [41] wherein the tumor is acute leukemia, chronic lymphatic leukemia, chronic myelocytic leukemia, polycythemia vera, malignant lymphoma, myeloma, brain tumor, head and neck cancer, esophageal cancer, thyroid cancer, small-cell lung cancer, non-small cell lung cancer, breast cancer, stomach cancer, gallbladder or bile duct cancer, liver cancer, pancreatic cancer, colon cancer, rectal cancer, ovarian cancer, chordoepithelioma, endometrial cancer, cervical cancer, urothelial cancer, renal cell cancer, prostate cancer, testicular tumor, Wilms' tumor, malignant melanoma, neuroblastoma, osteosarcoma, Ewing's sarcoma, or soft tissue sarcoma.

[43] A medicament comprising the compound according to any one of [1] to [39] or a pharmaceutically acceptable salt thereof in combination with another anti-cancer agent selected from the group consisting of an anti-cancerous alkylating agent, an anti-cancerous antimetabolite, an anti-cancerous antibiotic, a plant-based anti-cancer agent, an anti-cancerous platinum coordination compound, an anti-cancerous camptothecin derivative, an anti-cancerous tyrosine kinase inhibitor, a serine-threonine kinase inhibitor, a phospholipid kinase inhibitor, a monoclonal antibody, an interferon, a biological response modifier, a hormone preparatjon, an immune checkpoint inhibitor, an epigenetics-related molecule inhibitor, a post-translational protein modification inhibitor, and other anti-cancer agent or a pharmaceutically acceptable salt thereof.

[44] A method for treating cancer which comprises administering a therapeutically effective amount of the compound according to any one of [1] to [39] or a pharmaceutically acceptable salt thereof to a patient in need thereof.

[45] Use of the compound according to any one of [1] to [39] or a pharmaceutically acceptable salt thereof for the manufacture of an agent for treating cancer.

[46] A pharmaceutical composition for use in the treatment of cancer, comprising the compound according to any one of [1] to [39] or a pharmaceutically acceptable salt thereof.

[47] The compound according to any one of [1] to [39] or a pharmaceutically acceptable salt thereof for use in the treatment of cancer.

Effects of the Invention

The present compound has a potent inhibitory effect on the sphere-forming ability of cancer cells. In addition, the preferred present compound has high bioavailability after oral administration. Thus, the present compound is useful as an orally-available anti-tumor agent.

DESCRIPTION OF EMBODIMENTS

Hereinafter, the present invention is explained in detail. The number of carbon atoms in the definition of the "substituent" used herein may be expressed as, for example, "$C_{1-6}$". Specifically, the term "$C_{1-6}$ alkyl" is used for the same meaning as alkyl group having 1 to 6 carbon atoms.

Specific examples of "halogen atom" used herein include fluorine atom, chlorine atom, bromine atom, and iodine atom.

The term "$C_{1-6}$ alkyl group" used herein means a straight or branched, saturated hydrocarbon group having 1 to 6 carbon atoms. Preferred examples thereof include "$C_{1-4}$ alkyl group". Specific examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

The term "$C_{2-6}$ alkenyl group" used herein means a straight or branched, unsaturated hydrocarbon group having 2 to 6 carbon atoms and 1 to 3 carbon-carbon double bonds. Preferred examples thereof include "$C_{2-4}$ alkenyl group". Specific examples of the "$C_{2-6}$ alkenyl group" include ethenyl, propenyl, butenyl, pentenyl, and hexenyl.

The term "$C_{2-6}$ alkynyl group" used herein means a straight or branched, unsaturated hydrocarbon group having 2 to 6 carbon atoms and 1 to 3 carbon-carbon triple bonds. Preferred examples thereof include "$C_{2-4}$ alkynyl group". Specific examples of the "$C_{2-6}$ alkynyl group" include ethynyl, propynyl, butynyl, penthynyl, and hexynyl.

The term "$C_{1-4}$ alkylene group" used herein means a straight or branched, divalent saturated hydrocarbon group having 1 to 4 carbon atoms, or a divalent saturated hydrocarbon group containing a cyclic structure having 3 to 4 carbon atoms.

Specific examples of the straight or branched "$C_{1-4}$ alkylene group" include methylene, ethylene, trimethylene, tetramethylene, 1-methylmethylene, 1-ethylmethylene, 1-propylmethylene, 1-methylethylene, 2-methylethylene, and 1-ethylethylene. Preferred examples thereof include methylene and ethylene.

Specific examples of the "$C_{1-4}$ alkylene group" containing a cyclic structure include the following groups:

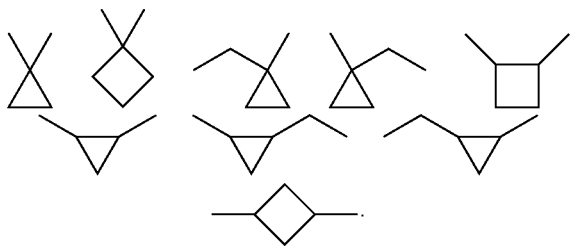

The term "$C_{3-4}$ alkenylene group" used herein means a straight or branched, divalent hydrocarbon group having 3 to 4 carbon atoms and a carbon-carbon double bond. Specific examples of the "$C_{3-4}$ alkenylene group" include propenylene and butenylene.

The term "$C_{3-4}$ alkynylene group" used herein means a straight or branched, divalent hydrocarbon group having 3 to 4 carbon atoms and a carbon-carbon triple bond. Specific examples of the "$C_{3-4}$ alkynylene group" include propynylene and butynylene.

The "$C_{1-6}$ alkyl" moiety of the term "$C_{1-6}$ alkoxy group" used herein is as defined in the above "$C_{1-6}$ alkyl". Preferred examples thereof include "$C_{1-4}$ alkoxy group". Specific examples of the "$C_{1-6}$ alkoxy group" include methoxy, ethoxy, propoxy, isopropoxy, butoxy, isobutoxy, sec-butoxy, and tert-butoxy.

The term "$C_{3-10}$ cycloalkyl group" used herein means a 3- to 10-membered monocyclic or polycyclic, saturated or partially-unsaturated hydrocarbon group. The group is preferably "$C_{3-7}$ cycloalkyl group", and more preferably cyclohexyl group. Specific examples of the "$C_{3-10}$ cycloalkyl group" cyclopropyl, cyclobutyl, cyclopentyl, cyclohexyl, cycloheptyl, cyclopentenyl, cyclohexenyl, decalinyl, adamantyl, and norbornyl.

The term "$C_{6-10}$ aryl group" used herein means an aromatic hydrocarbon group having 6 to 10 carbon atoms. The group is preferably "$C_6$ aryl group" (phenyl). Specific examples of the "$C_{6-10}$ aryl group" include phenyl, 1-naphthyl, or 2-naphthyl.

Examples of the term "5- to 10-membered heteroaryl group" used herein include a 5- to 10-membered mono- or bi-cyclic aromatic group which contains the same or different one or more (e.g. 1 to 4) heteroatoms selected from the group consisting of nitrogen atom, sulfur atom, and oxygen atom. The bicyclic heteroaryl group also encompasses a fused ring group of a monocyclic heteroaryl group mentioned above with an aromatic group (such as benzene and pyridine) or a non-aromatic ring (such as cyclohexyl and piperidine). Specific examples of the "heteroaryl group" include the groups of the following formulae:

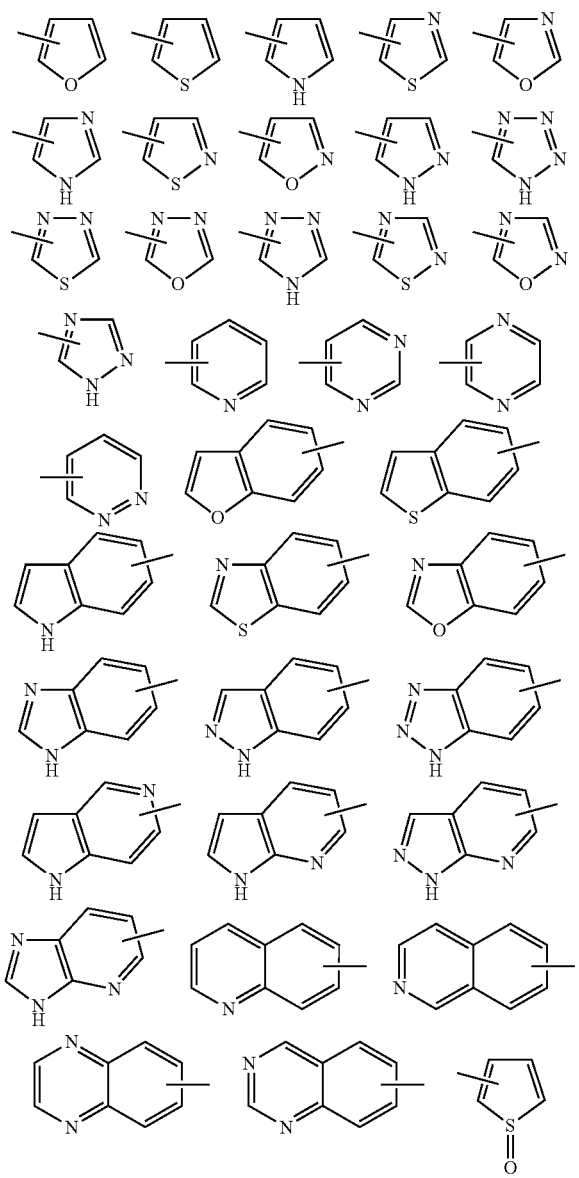

-continued

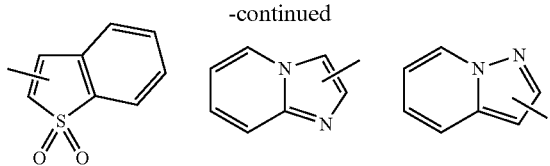

The bond across a ring in the above formulae means that a "group" is linked at any replaceable position in the ring. For example, when a group is the heteroaryl group of the following formula:

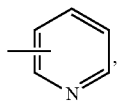

the group means 2-pyridyl group, 3-pyridyl group, or 4-pyridyl group.

Furthermore, when a "heteroaryl group" is a bicyclic group, for example, the croup of the following formula:

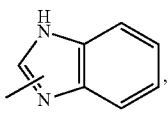

the group may be 1-benzimidazolyl, 2-benzimidazolyl, or 4-, 5-, 6- or 7-benzimidazolyl.

The term "aminocarbonyl group" used herein means a formyl group wherein hydrogen atom therein is replaced with amino group.

The "$C_{1-6}$ alkyl" moiety of the term "$C_{1-6}$ alkyl-carbonylamino group" used herein is as defined in the above "$C_{1-6}$ alkyl". The group is preferably "$C_{1-4}$ alkyl-carbonylamino group", and more preferably methylcarbonylamino group (acetamido group).

The "$C_{6-10}$ aryl" moiety of the term "$C_{6-10}$ aryloxy group" is as defined in the above "$C_{6-10}$ aryl". Preferred examples thereof include "$C_6$ aryloxy group" (phenoxy group).

The "$C_{1-6}$ alkoxy" moiety of the term "$C_{1-6}$ alkoxy-carbonyl group" used herein is as defined in the above "$C_{1-6}$ alkoxy". Preferred examples thereof include "$C_{1-4}$ alkoxy-carbonyl group". Specific examples of the "$C_{1-6}$ alkoxy-carbonyl group" include methoxycarbonyl, ethoxycarbonyl, and propoxycarbonyl.

The "$C_{1-6}$ alkyl" moiety of the term "$C_{1-6}$ alkyl-carbonyl group" used herein is as defined in the above "$C_{1-6}$ alkyl". Preferred examples thereof include "$C_{1-4}$ alkyl-carbonyl group". Specific examples of the "$C_{1-6}$ alkyl-carbonyl group" include acetyl, ethylcarbonyl, and propylcarbonyl.

The "$C_{1-6}$ alkyl" moiety of the term "$C_{1-6}$ alkylsulfonyl group" used herein is as defined in the above "$C_{1-6}$ alkyl". Preferred examples thereof include "$C_{1-4}$ alkylsulfonyl group". Specific examples of the "$C_{1-6}$ alkylsulfonyl group" include methylsulfonyl, ethylsulfonyl, and propylsulfonyl.

The "$C_{1-6}$ alkyl" moiety of the term "$C_{1-6}$ alkylsulfonylamino group" used herein is as defined in the above "$C_{1-6}$ alkyl". Preferred examples thereof include "$C_{1-4}$ alkylsulfonylamino group". Specific examples of the "$C_{1-6}$ alkylsulfonyiamino group" include methylsulfonylamino, ethylsulfonylamino, and propylsulfonylamino.

The "$C_{1-6}$ alkoxy" moiety of the term "$C_{1-6}$alkoxy-carbonylamino group" used herein is as defined in the above "$C_{1-6}$ alkoxy". Preferred examples thereof include "$C_{1-4}$ alkoxy-carbonylamino group". Specific examples of the "$C_{1-6}$ alkoxy-carbonylamino group" include methoxycarbonylamino, ethoxycarbonylamino, and propoxycarbonylamino.

The term "$C_{1-6}$ alkyl-carbonyloxy group" used herein means an oxy group substituted with the above "$C_{1-6}$ alkyl-carbonyl group". Preferred examples thereofinclude "$C_{1-4}$ alkyl-carbonyloxy group". Specific examples of the "$C_{1-6}$ alkyl-carbonyloxy group" include acetoxy, propionyloxy, and butyryloxy.

The term "aminosulfonyl group" used herein means a sulfo group wherein hydroxy group therein is substituted with amino group.

Examples of the substituent in the terms "optionally-substituted $C_{1-6}$ alkyl group", "optionally-substituted $C_{2-6}$ alkenyl group", "optionally-substituted $C_{2-6}$ alkynyl group", "optionally-substituted $C_{1-4}$ alkyiene group", "optionally-substituted $C_{3-4}$ alkenyiene group", "optionally-substituted $C_{3-4}$ alkynylene group", "optionally-substituted $C_{1-6}$ alkoxy group", "optionally-substituted $C_{1-6}$ alkyl-carbonyl group", "optionally-substituted $C_{1-6}$ alkylsulfonyl group", "optionally-substituted $C_{1-6}$ alkoxy-carbonyl group", "optionally-substituted $C_{1-6}$ alkyl-carbonylamino group", "optionally-substituted $C_{1-6}$ alkylsulfonylamino group", "optionally-substituted $C_{1-6}$ alkoxy-carbonylamino group", "optionally-substituted $C_{1-6}$ alkyl-carbonyloxy group" include hydroxy group, halogen atom, $C_{3-7}$ cycloalkyl group, and $C_{1-6}$ alkoxy group, and preferably fluorine atom.

Examples of the substituent in the terms "optionally-substituted $C_{6-10}$ aryl group", "optionally-substituted $C_{3-10}$ cycloalkyl group", "optionally-substituted 5- to 10-membered heteroaryl group", "optionally-substituted 5- or 6-membered cyclic amino group", and "optionally-substituted 5- or 6-membered cyclic aminocarbonyl group" include (a) halogen atom,
(b) alkyl which may be optionally substituted with the same or different 1 to 3 groups independently selected from the group consisting of halogen atom, hydroxy, and $C_{1-6}$ alkoxy,
(c) $C_{1-6}$ alkoxy which may be optionally substituted with the same or different 1 to 3 groups independently selected from the group consisting of halogen atom, hydroxy, and $C_{1-6}$ alkoxy,
(d) cyano,
(e) $C_{6-10}$ aryl which may be optionally substituted with the same or different 1 to 4 groups independently selected from the group consisting of halogen atom, $C_{1-6}$ alkyl, and $C_{1-6}$ alkoxy, and
(f) 5- or 6-membered heteroaryl which may be optionally substituted with the same or different 1 to 4 groups independently selected from the group consisting of halogen atom, $C_{1-6}$ alkyl, and $C_{1-6}$ alkoxy,
(g) $C_{6-10}$ aryloxy which may be optionally substituted with the same or different 1 to 4 groups independently selected from the group consisting of halogen atom, $C_{1-6}$ alkyl, and $C_{1-6}$ alkoxy,
(h) hydroxy,
(i) amino which may be optionally substituted with the same or different 1 to 2 $C_{1-6}$ alkyl groups,
(j) aminocarbonyl wherein the amino moiety thereof may be optionally substituted with the same or different 1 to 2 $C_{1-6}$ alkyl groups, (k) $C_{1-6}$ alkoxy-carbonyl wherein the alkoxy moiety thereof may be optionally substituted with the same or different 1 to 3 groups independently selected from the group consisting of halogen atom, hydroxy, and $C_{1-6}$ alkoxy, (l) $C_{1-6}$ alkyl-carbonyl wherein the alkyl moiety thereof may be optionally substituted with the same or different 1 to 3 groups independently selected from the group consisting of halogen atom, hydroxy, and $C_{1-6}$ alkoxy, (m) $C_{1-6}$ alkylsulfonyl wherein the alkyl moiety thereof may be optionally substituted with the same or different 1 to 3 groups independently selected from the group consisting of halogen atom, hydroxy, and $C_{1-6}$ alkoxy, (n) $C_{1-6}$ alkyl-carbonylamino wherein the alkyl moiety thereof may be optionally substituted with the same or different 1 to 3 groups independently selected from the group consisting of halogen atom, hydroxy, and $C_{1-6}$ alkoxy, (o) $C_{1-6}$ alkylsulfonylamino wherein the alkyl moiety thereof may be optionally substituted with the same or different 1 to 3 groups independently selected from the group consisting of halogen atom, hydroxy, and $C_{1-6}$ alkoxy, (p) $C_{1-6}$ alkoxy-carbonylamino wherein the alkoxy moiety thereof may be optionally substituted with the same or different 1 to 3 groups independently selected from the group consisting of halogen atom, hydroxy, and $C_{1-6}$ alkoxy, (q) $C_{1-6}$ alkyl-carbonyloxy wherein the alkyl moiety thereof may be optionally substituted with the same or different 1 to 3 groups independently selected from the group consisting of halogen atom, hydroxy, and $C_{1-6}$ alkoxy, (r) aminosulfonyl wherein the amino moiety thereof may be optionally substituted with the same or different 1 to 2 $C_{1-6}$ alkyl groups, and (s) $C_{3-10}$ cycloalkyl which may be optionally substituted with the same or different 1 to 4 groups independently selected from the group consisting of halogen atom, hydroxy, and $C_{1-6}$ alkoxy.

Examples of the substituent in the terms "optionally-substituted amino group", "optionally-substituted aminocarbonyl group", and "optionally-substituted aminosulfonyl group" include $C_{1-6}$ alkyl which may be optionally substituted with the same or different 1 to 4 groups independently selected from the group consisting of halogen atom, hydroxy, and $C_{1-6}$ alkoxy, and preferably $C_{1-3}$ alkyl.

In the present compound of formula (1'), $W^1$, $W^2$, $W^3$, $R^1$, $R^2$, $R^4$, $R^5$, n, ring $Q^1$, and ring $Q^2$ are preferably those shown below, but the technical scope of the present invention should not be limited to the following compounds.

$W^1$ preferably includes $C_{1-4}$ alkylene group which may be optionally substituted with the same or different 1 to 4 groups independently selected from the group consisting of halogen atom, hydroxy, and $C_{1-6}$ alkoxy. $W^1$ is more preferably methylene group which may be optionally substituted with the same or different 1 to 2 halogen atoms, or ethylene group which may be optionally substituted with the same or different 1 to 4 halogen atoms; and furthermore preferably methylene group.

$W^2$-$Q^2$ preferably includes —$NR^{3a}C(O)$-$Q^2$, —$NR^{3a}C(O)CH_2O$-$Q^2$, or —$C(O)NR^{3a}$-$Q^2$ wherein $R^{3a}$ is hydrogen atom or $C_{1-6}$ alkyl group. $W^2$-$Q^2$ is more preferably —NHC(O)-$Q^2$ or —C(O)NH-$Q^2$; and furthermore preferably —NHC(O)-$Q^2$.

In another embodiment, $W^2$-$Q^2$ preferably includes —$NR^{3a}C(O)$-$Q^2$, —$NR^{3a}C(O)CH_2O$-$Q^2$, —$C(O)NR^{3a}$-$Q^2$, or —$NR^{3a}C(O)$-CH=CH-$Q^2$ wherein $R^{3a}$ is hydrogen atom or $C_{1-6}$ alkyl group. $W^2$-$Q^2$ is more preferably —NHC(O)-$Q^2$, —C(O)NH-$Q^2$, or —NHC(O)-CH=CH-$Q^2$; and furthermore preferably —NHC(O)-$Q^2$.

Preferably, $R^1$ and $R^2$ independently include hydrogen atom, halogen atom, and $C_{1-4}$ alkyl group which may be optionally substituted with the same or different 1 to 3 halogen atoms. $R^1$ and $R^2$ are more preferably hydrogen atom, chlorine atom, or methyl group; and furthermore preferably hydrogen atom.

Ring $Q^1$ preferably includes (1) $C_{6-10}$ aryl group which may be optionally substituted with the same or different 1 to 4 groups independently selected from the group consisting of
  (a) halogen atom,
  (b) $C_{1-6}$ alkyl which may be optionally substituted with the same or different 1 to 3 groups independently selected from the group consisting of halogen atom, hydroxy, and $C_{1-6}$ alkoxy,
  (c) $C_{1-6}$ alkoxy which may be optionally substituted with the same or different 1 to 3 groups independently selected from the group consisting of halogen atom, hydroxy, and $C_{1-6}$ alkoxy,
  (d) cyano,
  (e) phenyl which may be optionally substituted with the same or different 1 to 4 groups independently selected from the group consisting of halogen atom, $C_{1-6}$ alkyl, and $C_{1-6}$ alkoxy,
  (f) 5- or 6-membered heteroaryl which may be optionally substituted with the same or different 1 to 4 groups independently selected from the group consisting of halogen atom, $C_{1-6}$ alkyl, and $C_{1-6}$ alkoxy,
  (g) phenoxy which may be optionally substituted with the same or different 1 to 4 groups independently selected from the group consisting of halogen atom, $C_{1-6}$ alkyl, and $C_{1-6}$ alkoxy,
  (h) hydroxy,
  (i) amino which may be optionally substituted with the same or different 1 to 2 $C_{1-6}$ alkyl groups, and
  (j) aminocarbonyl wherein the amino moiety thereof may be optionally substituted with the same or different 1 to 2 $C_{1-6}$ alkyl groups, (2) $C_{3-10}$ cycloalkyl group which may be optionally substituted with the same or different 1 to 5 groups independently selected from the group consisting of (a) to (j) defined in the above (1), or (3) 5- to 10-membered heteroaryl group which may be optionally substituted with the same or different 1 to 5 groups independently selected from the group consisting of (a) to (j) defined in the above (1).

Ring $Q^1$ preferably includes (1) phenyl group which may be optionally substituted with the same or different 1 to 5 groups independently selected from the group consisting of
  (a) halogen atom,
  (b) $C_{1-6}$ alkyl which may be optionally substituted with the same or different 1 to 3 groups independently selected from the group consisting of halogen atom, hydroxy, and $C_{1-6}$ alkoxy,
  (c) $C_{1-6}$ alkoxy which may be optionally substituted with the same or different 1 to 3 groups independently selected from the group consisting of halogen atom, hydroxy, and $C_{1-6}$ alkoxy,
  (d) cyano, (e) phenyl which may be optionally substituted with the same or different 1 to 4 groups independently selected from the group consisting of halogen atom, $C_{1-6}$ alkyl, and $C_{1-6}$ alkoxy, and (f) 5- or 6-membered heteroaryl which may be optionally substituted with the same or different 1 to 4 groups independently selected from the group consisting of halogen atom, $C_{1-6}$ alkyl, and $C_{1-6}$ alkoxy, or (2) pyridyl group which may be optionally substituted with the same or different 1 to 4 groups independently selected from the group consisting of (a) to (f) defined in the above (1).

Ring $Q^1$ furthermore preferably includes phenyl group which may be optionally substituted with the same or different 1 to 5 groups independently selected from (a) halogen atom, (b) $C_{1-6}$ alkyl which may be optionally substituted with the same or different 1 to 3 halogen atoms, and (c) $C_{1-6}$ alkoxy which may be optionally substituted with the same or different 1 to 3 halogen atoms.

Ring $Q^1$ is furthermore preferably phenyl group substituted with the same or different 1 to 3 halogen atoms.

Ring $Q^2$ is preferably pyridyl group, pyrimidyl group, pyridazyl group, pyrazyl group, oxazolyl group, thiazolyl group, isoxazolyl group, isothiazolyl group, quinolinyl group, isoquinolinyl group, quinazolinyl group, or quinoxalinyl group. The ring is more preferably pyridyl group, pyridazyl group, pyrazyl group, oxazolyl group, thiazolyl group, isoxazolyl group, or quinolinyl group; furthermore preferably pyridyl group or pyrazyl group; and most preferably pyridyl group.

$R^4$ preferably includes (1) hydrogen atom, (2) halogen atom, (3) $C_{1-6}$ alkyl group which may be optionally substituted with the same or different 1 to 3 groups independently selected from the group consisting of halogen atom, hydroxy, and $C_{1-6}$ alkoxy, (4) $C_{1-6}$ alkoxy group which may be optionally substituted with the same or different 1 to 3 groups independently selected from the group consisting of halogen atom, hydroxy, and $C_{1-6}$ alkoxy, (5) $C_{3-10}$ cycloalkyl group which may be optionally substituted with the same or different 1 to 4 groups independently selected from the group consisting of halogen atom, hydroxy, and $C_{1-6}$ alkoxy, (6) $C_{2-6}$ alkenyl group which may be optionally substituted with the same or different 1 to 2 halogen atoms, (7) $C_{2-6}$ alkynyl group which may be optionally substituted with the same or different 1 to 2 halogen atoms, (8) cyano group, or (9) amino group which may be optionally substituted with the same or different 1 to 2 $C_{1-6}$ alkyl groups.

$R^4$ preferably includes (1) hydrogen atom, (2) halogen atom, (3) $C_{1-6}$ alkyl group which may be optionally substituted with the same or different 1 to 3 groups independently selected from the group consisting of halogen atom, hydroxy, and $C_{1-6}$ alkoxy, (4) $C_{1-6}$ alkoxy group which may be optionally substituted with the same or different 1 to 3 groups independently selected. from the group consisting of halogen atom, hydroxy, and $C_{1-6}$ alkoxy, (5) $C_{2-6}$ alkenyl group which may be optionally substituted with the same or different 1 to 2 halogen atoms, or (6) amino group which may be optionally substituted with the same or different 1 to 2 $C_{1-6}$ alkyl groups.

$R^4$ furthermore preferably includes (1) hydrogen atom, (2) halogen atom, (3) $C_{1-6}$ alkyl group which may be optionally substituted with the same or different 1 to 3 groups independently selected from the group consisting of halogen atom, hydroxy, and $C_{1-6}$ alkoxy, (4) amino group.

$R^4$ is furthermore preferably methyl group substituted with 1 to 3 fluorine atoms; and most preferably methyl group substituted with 2 fluorine atoms.

$W^3$ is preferably (1) $C_{1-4}$ alkylene group which may be optionally substituted with the same or different 1 to 4 groups independently selected from the group consisting of halogen atom, hydroxy, and $C_{1-6}$ alkoxy, (2) $C_{3-4}$ alkenylene group which may be optionally substituted with the same or different 1 to 2 halogen atoms, or (3) $C_{3-4}$ alkynylene group which may be optionally substituted with the same or different 1 to 2 halogen atoms.

$W^3$ is more preferably methylene group which may be optionally substituted with the same or different 1 to 2 halogen atoms, or ethylene group which may be optionally substituted with the same or different 1 to 4 groups independently selected from the group consisting of halogen atom, hydroxy, and $C_{1-6}$ alkoxy; and furthermore preferably methylene group which may be optionally substituted with the same or different 1 to 2 halogen atoms.

Also, the preferred embodiment includes the present compound wherein one or more of $^1H$ in $W^3$ are replaced with $^2H(D)$ (i.e. deuterated form).

$R^5$ preferably includes hydroxy group, or $C_{1-6}$ alkoxy group which may be optionally substituted with the same or different 1 to 3 groups independently selected from the group consisting of halogen atom, hydroxy, and $C_{1-6}$ alkoxy. $R^5$ is more preferably hydroxy group.

n in the above [1] and m in the above [12] are independently selected from 1, 2, 3, 4, or 5. Preferably, n and m are independently 1, 2, or 3. When the number of the replaceable positions on the ring having the substituent $R^4$ or $R^{11}$ is less than 5, n and m are independently selected from the maximum replaceable number of $R^4$ or $R^{11}$. For example, when ring $Q^1$ is pyridyl group, m is selected from 1, 2, 3, or 4.

The present compound may be in the forms of a hydrate and/or a solvate. Thus, the present compound also encompasses hydrate and/or solvate such as ethanol solvate. Furthermore, the present compound encompasses all types of crystal forms of the present compound.

Specific examples of the pharmaceutically acceptable salt of the compound of formula (1') include an inorganic acid salt such as hydxochloride, hydrobromide, sulfate, phosphate, and nitrate; and an organic acid salt such as acetate, propionate, oxalate, succinate, lactate, malate, tartrate, citrate, maieate, fumarate, methanesulfonate, p-toluenesulfonate, benzenesulfonate, and ascorbate.

The compound of formula (1') may be in the form of a tautomer. Thus, the present compound also encompasses the tautomer of the compound of formula (1').

The compound of formula (1') may contain one or more asymmetric carbon atoms. Thus, the present compound encompasses not only racemic forms of the compound of formula (1') but also optically-active forms thereof. When the compound of formula (1') contains two or more asymmetric carbon atoms, the compound can result in various stereoisomerisms. Thus, the present compound also encompasses the stereoisomer of the compound and a mixture or isolate thereof.

Also, the compound of formula (1') encompasses the compound wherein one or more of $^1H$ are replaced with $^2H(D)$ (i.e. deuterated form).

PREPARATIONS

The present compounds can be prepared according to processes shown below and according to the processes in combination with known compounds and known synthesis processes.

As appropriate, each compound used as a starting compound may be used in the salt form. The shown processes are lust examples to prepare the compounds, and may be optionally modified by those skilled in the organic synthesis field.

In each process shown below, any functional groups which need to be protected may be optionally protected and then deprotected after the reaction or reactions are completed to give the desired compound even though the use of protective groups is not specifically described.

The protective group used herein includes any conventional groups described in various literatures, for example, T. W. Greene and P. G. M. Wuts, "Protective Groups Organic Synthesis", 3rd Ed., John Wiley and Sons, inc., New York (1999). In more detail, specific examples of the protective groups for amino group include benzyloxycarbonyl, tert-butoxycarbonyl, acetyl, and benzyl, and specific examples of the protective groups for hydroxy group include trialkylsilyl, acetyl, and benzyl.

The protective groups can be introduced and cleaved according to commonly-used methods in synthetic organic chemistry (e.g. the method described in T. W. Greene and P. G. M. Wuts, "Protective Groups Organic Synthesis", 3rd Ed., John Wiley and Sons, inc., New York (1999)) and similar methods thereto.

Preparation 1

One of the compounds of formula (1'), the compound of formula (1-7) is prepared by linking each fragment in positions a and b, respectively:

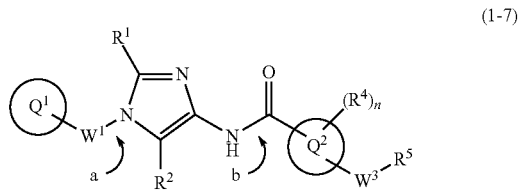

wherein $W^1$, $W^3$, $R^1$, $R^2$, $R^4$, $R^5$, n, ring $Q^1$, and ring $Q^2$ are as defined in the above [1].

The processes for forming each bond in positions a and b can be illustrated as follows, but the order of procedure for forming each bond may be optionally changed:

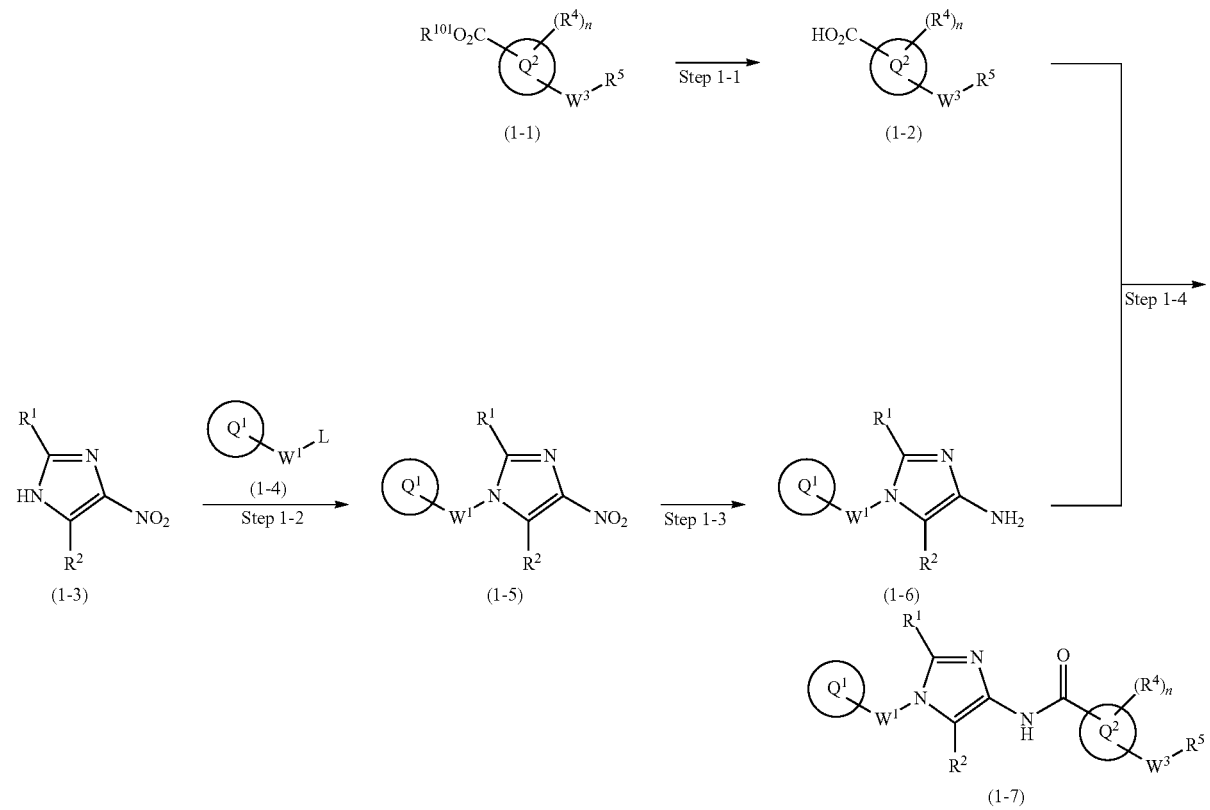

wherein $W^1$, $W^3$, $R^1$, $R^2$, $R^4$, $R^5$, n, ring $Q^1$, and ring $Q^2$ are as defined in the above [1]; $R^{101}$ is $C_{1-6}$ alkyl group; L is a leaving group (such as iodine atom, bromine atom, chlorine atom, and substituted sulfonyl group (e.g. methanesulfonyl group and p-toluenesulfonyl group)).

Compound (1-1) may be a commercially available product or be prepared according to known synthesis processes (e.g. New Version of Heterocyclic Compound (advanced level) edited by Kodansha Scientific Ltd.).

Step 1-1: Preparation Process of Compound (1-2)

Compound (1-2) is prepared by hydrolyzing compound (1-1) according to a similar process to a known process (e.g. Protective Groups in Organic Synthesis 3rd Edition (John Wiley & Sons, Inc.), Comprehensive Organic Transformation, by R. C. Larock, VCH publisher Inc., 1989).

Step 1-2: Preparation Process of Compound (1-5)

Compound (1-5) is prepared by the alkylation reaction of compounds (1-3) and (1-4) in an inert solvent in the presence of a base.

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific examples of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, N,N-dimethylformamide, N-methyl-2-pyrrolidinone, and dimethylsulfoxide; a basic solvent such as pyridine; and a mixture thereof.

The reaction temperature is typically 0° C. to 150° C., preferably 20° C. to 100° C., but is not limited thereto. The reaction time is typically 30 minutes to 48 hours, preferably 30 minutes to 10 hours.

Step 1-3: Preparation Process of Compound (1-6)

Compound (1-6) is prepared by reducing the nitro group in compound (1-5). For example, reductions under an acidic condition with a metal such as zinc, iron, and tin or a metal salt such as tin (II) chloride; reductions with a sulfide such as sodium hypodisulfite ($Na_2S_2O_4$); and catalytic hydrogenations with a metal catalyst such as palladium/carbon, Raney nickel, platinum oxide/carbon, and rhodium/carbon under hydrogen atmosphere may be used.

In the reduction with a metal or a metal salt, the amount, of the metal or metal salt to be used is typically about 1 mole to 100 moles, preferably about 10 moles to 30 moles per mole of compound (1-5). Also, the amount of the acid to be used is typically about 1 mole to 100 moles, preferably about 10 moles to 30 moles per mole of compound (1-5). The reduction is typica carried out in a solvent which has no negative effect on the reaction (e.g. ethanol). The reaction temperature is typically 0° C. to 100° C., but is not limited thereto. The reaction time is typically 30 minutes to 8 hours.

In the catalytic hydrogenation reaction, the amount of the metal catalyst to be used for compound (1-5) is typically 0.1% by weight to 1000% by weight, preferably 1% by weight to 100% by weight. The reaction may be carried out in a solvent such as an alcohol such as methanol; an ether such as tetrahydrofuran; and an ester such as ethyl acetate. The hydrogen pressure is typically 1 atm to 100 atms, preferably 1 atm to 5 atms. The reaction temperature is typically 0° C. to 120° C., preferably 20° C. to 80° C., but is not limited thereto. The reaction time is typically 30 minutes to 72 hours, preferably 1 hour to 48 hours.

Also, the reaction may be carried out in the presence of an acid catalyst, as appropriate. For example, an organic acid such as formic acid, acetic acid, and trifluoroacetic acid, and an inorganic acid such as sulfuric acid, hydrochloric acid, and hydrobromic acid are used as the acid catalyst. The amount of the acid to be used is 0.1 mole or more per mole of compound (1-5).

Step 1-4: Preparation Process of Compound (1-7)

Compound (1-7) is prepared by reacting compound (1-2) with compound (1-6) in an inert solvent in the presence of a condensation agent.

The reaction may be carried out in the presence of a base, as appropriate. The reaction temperature is typically about −20° C. to the boiling point of the used solvent, but is not limited thereto. The reaction time is typically 10 minutes to 48 hours, which may vary according to various conditions such as a reaction temperature, a condensation agent, a starting material, and a solvent to be used.

Specific examples of the condensation agent include dicyclohexylcarbodiimide (DCC), diisopropyicarbodiimide (DIPC), 1-ethyl-3-(3-dimethylaminopropyl)-carbodiimide (WSC), benzotriazol-1-yl-tris(dimethylamino)phosphonium hexafluorophosphate (BOP), diphenylphosphoryl azide (DPPA), N,N-carbonyldiimidazole (CDI), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), and diphenyl chlorophosphate. As appropriate, the reaction may be carried out with the addition of an additive such as N-hydroxysuccinimide (HOSu), 1-hydroxybenzotriazole (HOBt), and 3-hydroxy-4-oxo-3,4-dihydro-1,2,3-benzotriazine (HOOBt).

Specific examples of the base include an organic base such as triethylamine, diisopropylethylamine, and pyridine; an inorganic base such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and a metal alkoxide such as sodium methoxide and potassium tert-butoxide.

Specific example of the inert solvent include a halogenated hydrocarbon such as chloroform and dichloromethane; an aromatic hydrocarbon such as toluene; an ether-type solvent such as diethyl ether, tetrahydrofuran (THF), and 1,4-dioxane; an aprotic polar solvent such as acetonitrile, acetone, methyl ethyl ketone, dimethylformamide, N-methyl-2-pyrrolidinone, and dimethylsulfoxide; a basic solvent such as pyridine; and a mixture thereof.

Compound (1-7) is also prepared by reacting an acid halide or an acid anhydride derived from compound (1-2) with compound (1-6) in an inert solvent in the presence of a base.

Preparation 2

In the compounds of formula (1-1), the compounds of formulae (2-5), (2-8), (2-11), and (2-13) are prepared according to, for example, the following process.

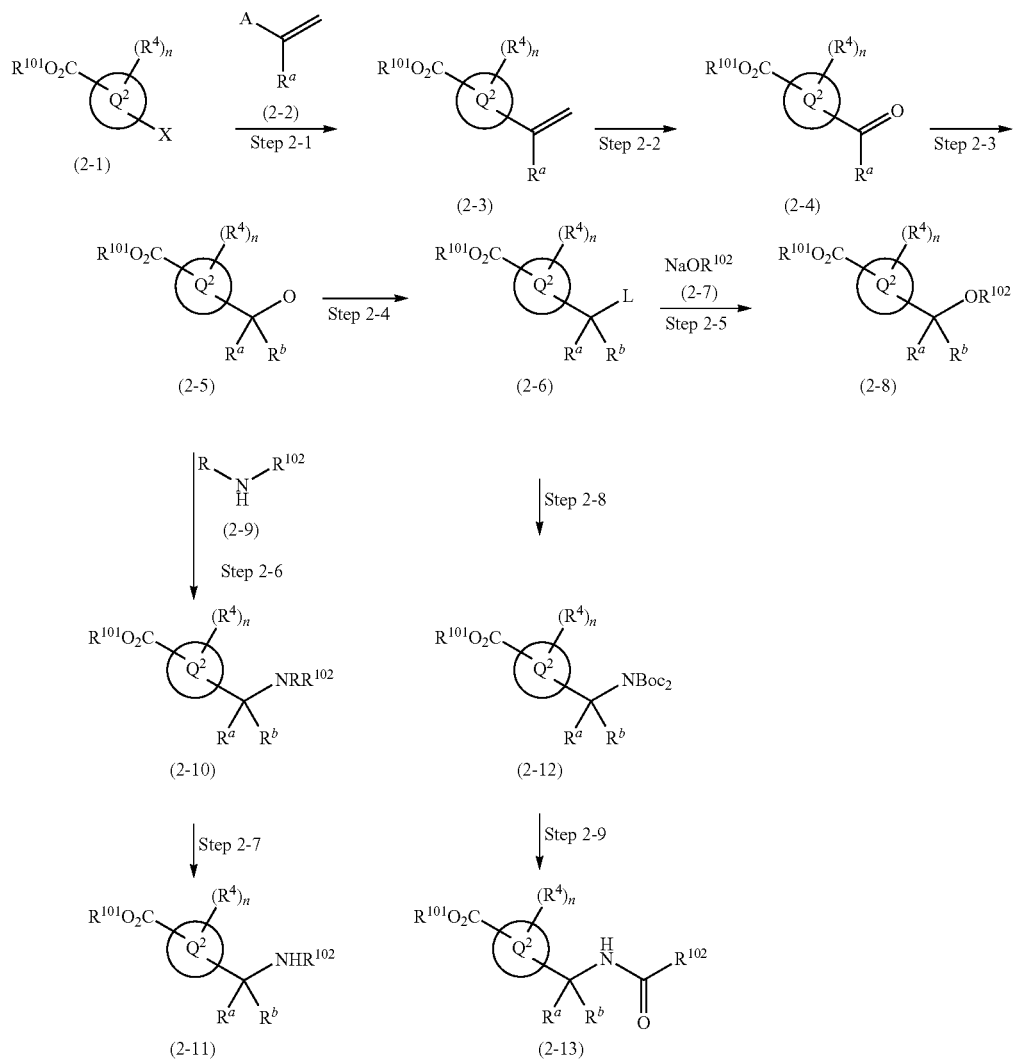

wherein $R^4$, n, and ring $Q^2$ are as defined in the above [1], A is boronic acid or boronate; $R^{101}$ is $C^{1-6}$ alkyl group; $R^{102}$ is optionally-substituted $C_{1-6}$ alkyl group; $R^a$ and $R^b$ are independently the same or different hydrogen atom or methyl group; R is benzenesulfonyi group substituted with one or two nitro groups; X is halogen atom, and L is a leaving group (such as iodine atom, bromine atom, chlorine atom, and substituted sulfonyl group (e.g. methanesulfonyl group and p-toluenesulfonyl group)).

Step 2-1: Preparation Process of Compound (2-3)

Compound (2-3) is prepared by reacting compound (2-1) with compound (2-2) in an inert solvent in the presence of a palladium catalyst and a base.

Specific examples of the palladium catalyst include tetrakis(triphenyiphosphine)palladium (0), bis(dibenzylideneacetone)palladium (0), tris(dibenzylideneacetone)dipalladium (0), bis(tri-tert-butylphosphine)palladium (0), [1,1'-bis(diphenylphosphino)ferrocene]palladium (II) dichloride.

Specific examples of the base include an inorganic base such as potassium carbonate, sodium carbonate, cesium carbonate, potassium phosphate, potassium hydroxide, and sodium hydroxide.

Specific examples of the inert solvent include toluene, 1,2-dimethoxyethane, 1,4-dioxane, DMF, water, and a mixture thereof.

The reaction temperature is typically 50° C. to 50° C., preferably 80° C. to 120° C., but is not limited thereto. Also, the reaction may be carried out under microwave irradiation. The reaction time is typically 1 hour to 24 hours, preferably 2 hours to 12 hours.

Step 2-2: Preparation Process of Compound (2-4)

Compound (2-4) is prepared by reacting compound (2-3) with osmium tetroxide or potassium osmate (IV) dihydrate in the presence of sodium periodate.

Examples of the solvent used include acetone, 1,4-dioxane, THF, tert-butanol, water, and a mixture thereof.

The reaction temperature is typically 0° C. to 100° C., preferably 25° C. to 50° C., but is not limited thereto. The reaction time is typically 1 hour to 72 hours, preferably 1 hour to 24 hours.

Also, compound ('-4) is prepared by treating compound (2-3) with oxygen currents including ozone and then reacting the treated compound with a reducing agent such as dimethyl sulfide in a solvent such as dichloromethane, ethyl acetate, and methanol. The reaction temperature is typically −78° C. to room temperature, but is not limited thereto. The reaction time is typically 1 hour to 72 hours, preferably 6 hours to 24 hours.

Step 2-3: Preparation Process of Compound (2-5)

Compound (2-5) is prepared by reacting compound (2-4) with an organometallic reagent or a hydride reducing agent.

Specific examples of the organometallic reagent include methyllithium reagent and methyl Grignard reagent.

Specific examples of the hydride reducing agent include sodium borohydride and sodium cyanoborohydride.

The solvent used in the reaction with the organometallic reagent includes THF, diethyl ether, and a mixture thereof, and the solvent used in the reaction with the hydride reducing agent includes methanol, ethanol, dichloromethane, toluene, and a mixture thereof.

The reaction temperature is typically −78° C. to 50° C., preferably 0° C. to 25° C., but is not limited thereto. The reaction time is typically 5 minutes to 12 hours, preferably 30 minutes to 6 hours.

Step 2-4: Preparation Process of Compound (2-6)

Compound (2-6) wherein L is substituted sulfonyl group is prepared by reacting compound (2-5) with an alkyl- or aryl-sulfonyl chloride in an inert solvent in the presence of a base.

Specific examples of the alkyl- or aryl-sulfonyl chloride include methanesulfonyl chloride, benzenesulfonyl chloride, p-toluenesulfonyl chloride, and 2,4,6-trimethylbenzene chloride.

Examples of the base include an organic base such as triethylamine, diisopropylethylamine, and pyridine; potassium carbonate, sodium carbonate, cesium carbonate, potassium hydrogen carbonate, and sodium hydrogen carbonate.

Examples of the inert solvent include THF, dichloromethane, toluene, and a mixture thereof.

The reaction temperature is typically 0° C. to 100° C., preferably 0° C. to 50° C., but is not limited thereto. The reaction time is typically 1 hour to 72 hours, preferably 1 hour to 24 hours.

Compound (2-6) wherein L is halogen is prepared by reacting compound (2-5) with a halogenating agent or alkyl -or aryl-sulfonyl chloride and an alkali metal halide in an inert solvent.

Examples of the halogenating agent include thionyl chloride, oxalyl dichloride, phosphorus tribromide, phosphorus pentabromide, and phosphorus oxychloride.

Specific examples of the alkyl- or aryl-sulfonyl chloride include methanesulfonyl chloride, benzenesulfonyl chloride, p-toluenesulfonyi chloride, and 2,4,6-trimethylbenzenesulfonyi chloride, and examples of the alkali metal halide include lithium chloride, sodium chloride, potassium chloride, lithium bromide, sodium bromide, potassium bromide, lithium iodide, sodium iodide, and potassium iodide.

Step 2-5: Preparation Process of Compound (2-8)

Compound (2-8) is prepared by reacting compound (2-6) with sodium alkoxide of formula (2-7). As appropriate, sodium alkoxide may be prepared from sodiummetal and various alcohols.

Examples of the solvent used include methanol, ethanol, THF, DMF, 1,4-dioxane, and a mixture thereof.

The reaction temperature is typically 0° C. to 100° C., preferably 0° C. to 50° C., but is not limited thereto. The reaction time is typically 30 minutes to 12 hours, preferably 1 hour to 6 hours.

Step 2-6: Preparation Process of Compound (2-10)

Compound (2-10) is prepared by the Mitsunobu reaction of compound (2-5) and benzenesulfonamide of formula (2-9) in an inert solvent in the presence of a Mitsunobu reagent.

Examples of the Mitsunobu reagent include diethyl azocecboxylate (DEAD), diisopropyl azodicarhoxylate (DIAD), triphenylphosphine, and tributylphosphine. Also, cyanomethylenetrimethylphosphorane (Tsunoda Reagent) may be used.

Examples of the inert solvent include toluene, benzene, THF, 1,4-dioxane, and a mixture thereof.

The reaction temperature is typically 0° C. to 100° C., preferably 0° C. to 50° C., but is not limited thereto. The reaction time is typically 1 hour to 48 hours, preferably 12 hours to 24 hours.

Step 2-7: Preparation Process of Compound (2-11)

Compound (2-11) is prepared by reacting compound (2-10) with a thiol in the presence of a base and cleaving benzenesulfonyl group.

Examples of the thiol include thiophenol and dodecanethiol.

Examples of the base include an inorganic base such as cesium carbonate and potassium carbonate.

The solvent used includes DMF, toluene, THF, 1,4-dioxane, and a mixture thereof.

The reaction temperature is typically 0° C. to 100° C., preferably 0° C. to 50° C., but is not limited thereto. The reaction time is typically 1 hour to 48 hours, preferably 3 hours to 12 hours.

Step 2-8: Preparation Process of Compound (2-12)

Compound (2-12) is prepared by reacting compound (2-6) with di-tert-butyl iminodicarboxylate in an inert solvent in the presence of a base.

Examples of the base include sodium hydride, potassium tert--butoxide, sodium bis(trimethylsilyl)amide, lithium bis(trimethylsilyl)amide, potassium bis(trimethylsilyl)amide, and lithium diisopropylamide.

Examples of the inert solvent include DMF, THF, and a mixture thereof.

The reaction temperature is typically 0° C. to 150° C., preferably 25° C. to 120° C., but is not limited thereto. The reaction time is typically 1 hour to 72 hours, preferably 6 hours to 24 hours.

Step 2-9: Preparation Process of Compound (2-13)

Compound (2-13) is prepared by cleaving Boc group in compound (2-12) under an acidic condition and then treating the resulting amine with an acylating agent in an inert solvent in the presence of a base.

Examples of the acid used in the deprotection step include trifluoroacetic acid, hydrochloric acid, and sulfuric acid.

The reaction temperature is typically 0° C. to 100° C., preferably 0° C. to 50° C., but is not limited thereto. The reaction time is typically 1 hour to 72 hours, preferably 6 hours to 24 hours.

The acylating agent includes carboxylic halide such as $R^{102}COCl$ and $R^{102}COBr$; and carboxylic anhydride such as $(R^{102}CO)_2O$. As appropriate, a promoter such as DMAP may be used.

Examples of the base include an organic base such as triethylamine, diisopropylethylamine, and pyridine; potassium carbonate, sodium carbonate, cesium carbonate, potassium hydrogen carbonate, and sodium hydrogen carbonate.

Examples of the inert solvent include dichloromethane, 1,2-dichloroethane, THF, toluene, ethyl acetate, and a mixture thereof.

The reaction temperature is typically 0° C. to 100° C., preferably 0° C. to 50° C., but is not limited thereto. The reaction time is typically 30 minutes to 12 hours, preferably 1 hour to 6 hours.

Preparation 3

One of the compounds of formula (2-1), the compound of formula (3-5) is prepared according to, for example, the following process.

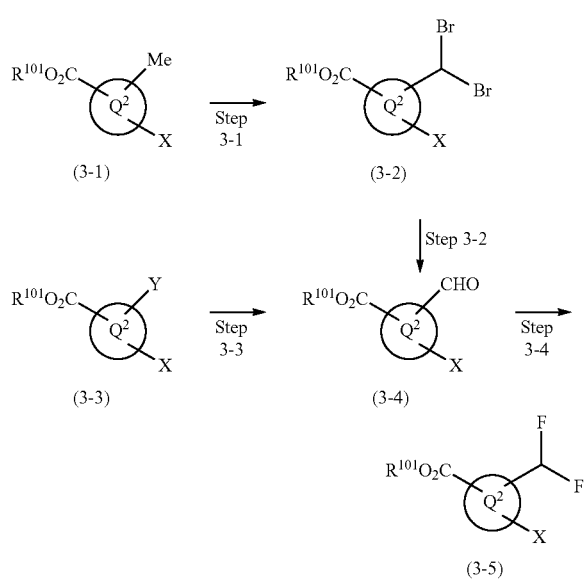

wherein ring $Q^2$ is as defined in the above [1]; $R^{101}$ is $C_{1-6}$ alkyl group; X is halogen atom; and Y is bromine atom or iodine atom.

Step 3-1: Preparation Process of Compound (3-2)

Compound (3-2) is prepared by reacting compound (3-1) with a brominating agent in an inert solvent in the presence of a radical initator.

Specific examples of the radical initiator include azobisisobutyronitrile (AIBN) and benzoyl peroxide (BPO).

Specific examples of the brominating agent include N-bromosuccinimide and bromine.

Examples of the inert solvent include carbon tetrachloride, chlorobenzene, and a mixture thereof.

The reaction temperature is typically 50° C. to 150° C., preferably 80° C. to 120° C., but is not limited thereto. The reaction time is typically 3 hours to 48 hours, preferably 4 hours to 12 hours.

Step 3-2: Preparation Process of Compound (3-4)

Compound (3-4) is prepared by reacting compound (3-2) with silver nitrate in an inert solvent.

Specific examples of the inert solvent include acetonitrile, THF, 1,4-dioxane, and a mixture thereof.

The reaction temperature is typically 50° C. to 150° C., preferably 80° C. to 120° C., but is not limited thereto. The reaction time is typically 3 hours to 48 hours, preferably 4 hours to 12 hours.

Step 3-3: Preparation Process of Compound (3-4)

Compound (3-4) is also prepared by reacting compound (3-3) with an organometallic reagent and then treating the resulting compound with a formylating agent.

Examples of the organometallic reagent include isopropylmagnesium chloride-lithium chloride complex, isopropylmagnesium chloride, and n-butyllithium.

Examples of the solvent used include THF, diethyl ether, toluene, and a mixture thereof.

Examples of the formylating agent include DMF and N-formylmorpholine.

The reaction temperature is typically −78° C. to 50° C., preferably −30° C. to 25° C., but is not limited thereto. The reaction time is typically 30 minutes to 24 hours, preferably 1 hour to 6 hours, Step 3-4: Preparation Process of Compound (3-5)

Compound (3-5) is prepared by reacting compound (3-4) with a deozofluorinating agent in an inert solvent.

Specific examples of the deoxofluorinating agent include diethylaminosulfur trifluoride (DAST), bis(2-methoxyethyl) aminosulfur trifluoride (Deoxo-Fluor®), XtalFluor-E®, XtalFluor-M®, and 4-tert-butyl-2,6-dimethylphenylsulfur trifluoride (Fluolead®). As appropriate, compounds such as DBU, triethylamine trihydrofluoride, and triethylamine dihydrofluoride may be used as a promoter.

Specific examples of the inert solvent include dichloromethane, 1,2-dichloroethane, toluene, THF, and a mixture thereof.

The reaction temperature is typically −20° C. to 50° C., preferably 0° C. to 25° C., but is not limited thereto. The reaction time is typically 10 minutes to 12 hours, preferably 30 minutes to 3 hours.

Compound (3-5) is also prepared by reacting compound (3-4) with sulfur tetrafluoride.

Preparation 4

One of the compounds of formula (1-1), the compound of formula (4-3) is prepared according to, for example, the following process.

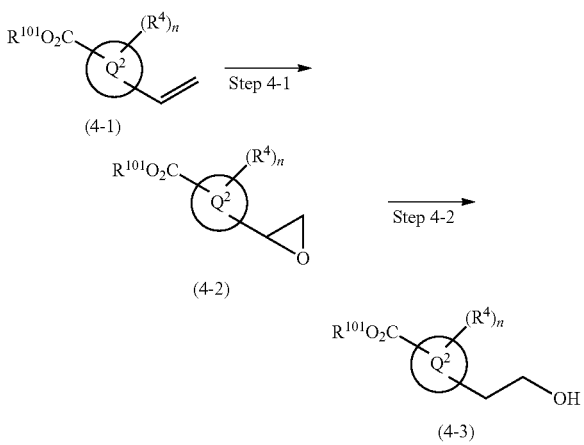

wherein $R^4$, n, and ring $Q^2$ are as defined in the above [1]; and $R^{101}$ is $C_{1-6}$ alkyl group.

Step 4-1: Preparation Process of Compound (4-2)

Compound (4-2) is prepared by hydrpbrominating compound (4-1) with a brominating agent in an inert solvent and then treating the resulting compound with a base.

Examples of the brominating agent used in the hydrobromination step include N-bromosuccinimide.

Examples of the inert solvent include tert-butanol, water, THF, 1,4-dioxane, and a mixture thereof.

The reaction temperature is typically 0° C. to 100° C., preferably 0° C. to 50° C., but is not limited thereto. The reaction time is typically 30 minutes to 12 hours, preferably 1 hour to 6 hours.

Examples of the base used in the treatment step include sodium hydride, potassium hydride, NaHMDS, potassium-tert-butoxide, sodium hydroxide, potassium hydroxide, and triethylamine.

Examples of the inert solvent include THF, 1, 4-dioxane, DMF, and a mixture thereof.

The reaction temperature is typically 0° C. to 80° C., preferably 0° C. to 50° C., but is not limited thereto. The reaction time is typically 30 minutes to 8 hours, preferably 1 hour to 4 hours.

Step 4-2: Preparation Process of Compound (4-3)

Compound (4-3) is prepared by hydrogenating compound (4-2) with a palladium catalyst in an inert solvent.

Examples of the palladium catalyst include palladium-carbon and palladium hydroxide.

Examples of the solvent used include THF, methanol, ethanol, 2-propanol, and a mixture thereof.

The reaction temperature is typically 0° C. to 100° C., preferably 25° C. to 80° C., but is not limited thereto. The reaction time is typically 1 hour to 12 hours, preferably 2 hours to 6 hours.

Preparation 5

One of the compounds of formula (1-1), the compound of formula (5-1) is prepared according to, for example, the following process.

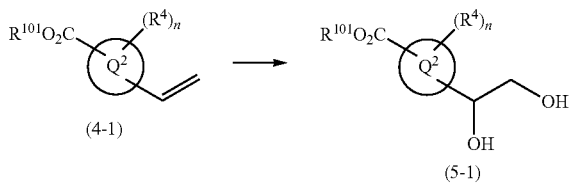

wherein $R^4$, n, and ring $Q^2$ are as defined in the above [1]; and $R^{101}$ is $C_{1-6}$ alkyl group.

Compound (5-1) is prepared by reacting compound (4-1) with osmium tetroxide in an appropriate solvent in the presence of N-methylmbrpholine-N-oxide.

Examples of the solvent used include acetone, 1,4-dioxane, THF, tert-butanol, water, and a mixture thereof.

The reaction temperature is typically 0° C. to 100° C., preferably 25° C. to 50° C., but is not limited thereto. The reaction time is typically 1 hour to 72 hours, preferably 6 hours to 24 hours.

Preparation 6

One of the compounds of formula (1-1), the compound of formula (6-2) is prepared according to, for example, the following process.

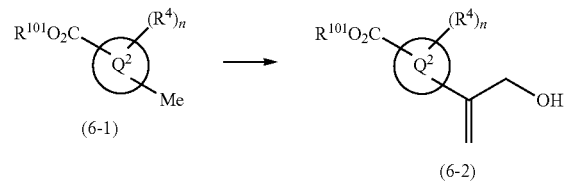

wherein $R^4$, n, and ring $Q^2$ are as defined in the above [1]; and $R^{101}$ is $C_{1-6}$ alkyl group.

Compound (6-2) is prepared by reacting compound (6-1) with paraformaldehyde under microwave irradiation with heating in the presence of a base.

Examples of the base include N,N-diisopropylethylamine, triethylamine, pyridine, and DBU.

Examples of the solvent used include water, THF, 1,4-dioxane, and a mixture thereof.

The reaction temperature is typically 100° C. to 200° C., preferably 120° C. to 180° C., but is not limited thereto. The reaction time is typically 30 minutes to 12 hours, preferably 1 hour to 6 hours, Preparation 7

One of the compounds of formula (1-1), the compound of formula (7-2) is prepared according to, for example, the following process.

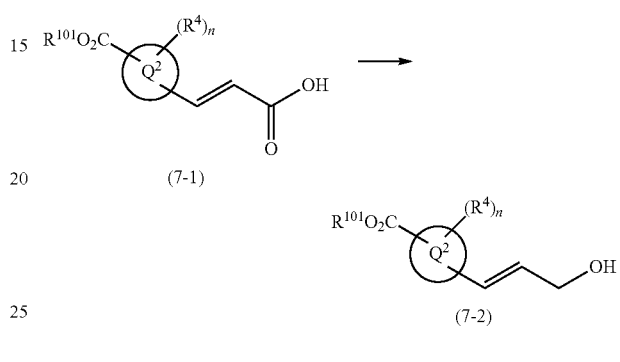

wherein $R^4$, n, and ring $Q^2$ are as defined in the above [1]; and $R^{101}$ is $C_{1-6}$ alkyl group.

Compound (7-2) is prepared by reacting compound (7-1) with a carboxylic acid chloride in the presence of a base to convert the compound to an acid anhydride, and then reducing the resulting acid anhydride with a hydride reducing agent.

Examples of the base used in the step for producing the acid anhydride include N-methylmorpholjne, N,N-diisopropylethylamine, triethylamine, pyridine, and DBU.

Specific examples of the carboxylic acid chloride include isobutyl chloroformate, ethyl chloroformate, methyl chloroformate, and acetyl chloride.

Examples of the solvent used include DME, THF, 1,4-dioxane, dichloromethane, 1,2-dichloroethane, and a mixture thereof.

The reaction temperature is typically 0° C. to 100° C., preferably 0° C. to 25° C., but is not limited thereto. The reaction time is typically 30 minutes to 12 hours, preferably 1 hour to 6 hours.

Specific examples of the hydride reducing agent used in the reduction step include sodium borohydride and sodium triacetoxyborobydride.

Examples of the solvent used include methanol, ethanol, 2-propanol, and THF.

The reaction temperature is typically 0° C. to 50° C., preferably 0° C. to 25° C., but is not limited thereto. The reaction time is typically 30 minutes to 12 hours, preferably 1 hour to 6 hours.

Preparation 8

One of the compounds of formula (1'), the compound of formula (8-3) is prepared according to, for example, the following process.

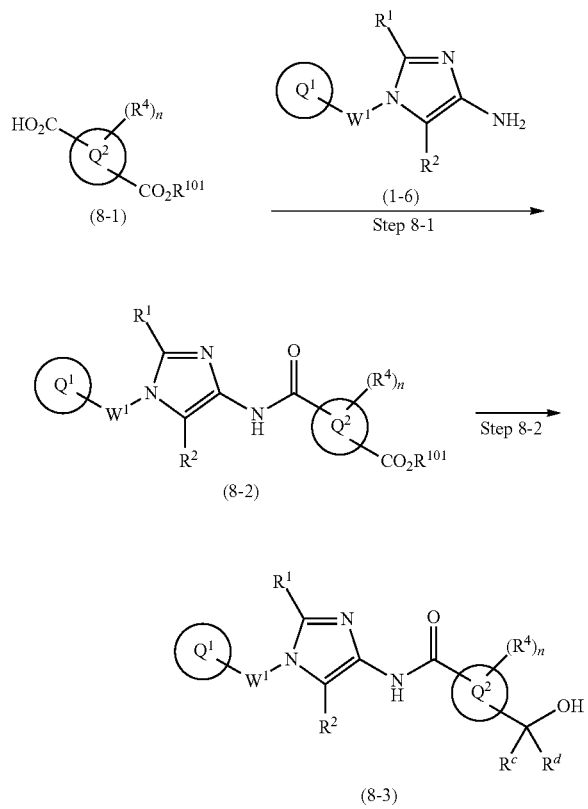

wherein $W^1$, $R^1$, $R^2$, $R^4$, n, ring $Q^1$, and ring $Q^2$ are as defined in the above [1]; $R^{101}$ is $C_{1-6}$ alkyl group; and $R^c$ and $R^d$ are independently the same or different hydrogen atom, deuterium atom, or methyl group.

Step 8-1: Preparation Process of Compound (8-2)

Compound (8-2) is prepared from compounds (8-1) and (1-6) according to the process of Step 1-4.

Step 8-2: Preparation Process of Compound (8-3)

Compound (8-3) is prepared by reacting compound (8-2) with an organometallic reagent or a hydride reducing agent in an inert solvent.

Specific examples of the organometallic reagent include methyllithium reagent and methyl Grignard reagent. Examples of the solvent used include THF, diethyl ether, and a mixture thereof.

Specific examples of the hydride reducing agent include sodium horohydride, lithium horohydride, lithium aluminum hydride, sodium cyanoborohydride, lithium triethylborohydride, diisobutylaluminium hydride, sodium bis(2-methoxyethoxy)aluminium hydride, lithium borodeuteride, and lithium aluminum deuteride. Examples of the solvent used include methanol, ethanol, dichloromethane, toluene, and a mixture thereof.

The reaction temperature is typically −78° C. to 25° C., preferably 0° C. to 25° C., but is not limited thereto. The reaction time is typically 5 minutes to 12 hours, preferably 30 minutes to 6 hours.

Preparation 9

In the compounds of formula (1'), the compounds of formulae (9-2), (9-3), and (9-4) are prepared according to, for example, the following process.

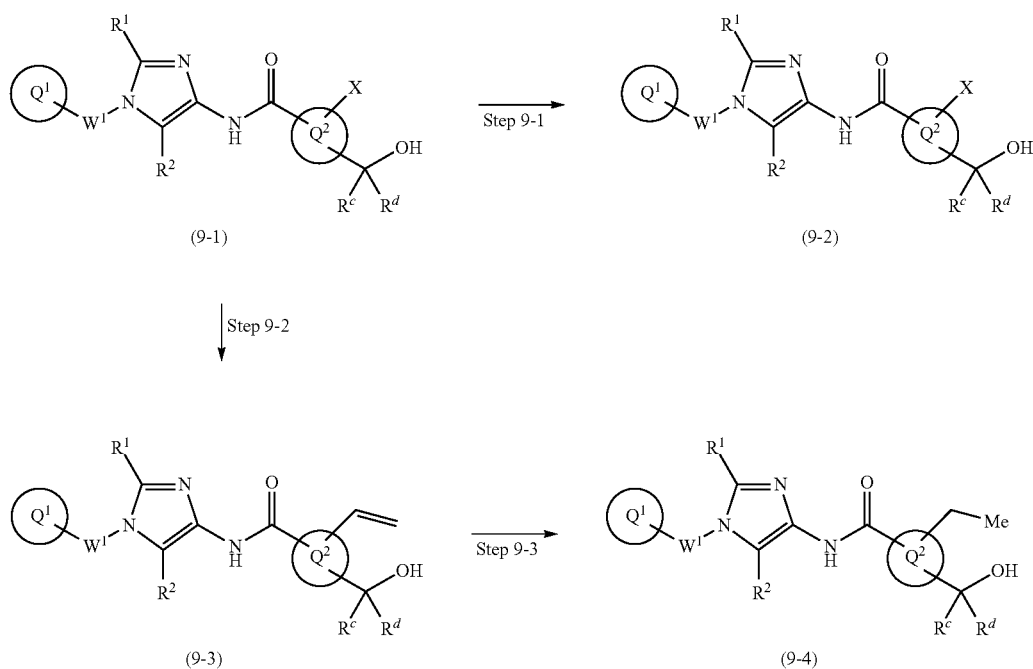

wherein $W^1$, $R^1$, $R^2$, ring $Q^1$, and ring $Q^2$ are as defined in the above [1]; X is halogen atom; and $R^c$ and $R^d$ are independently the same or different hydrogen atom, deuterium atom, or methyl group.

Step 9-i: Preparation Process of Compound (9-2)

Compound (9-2) is prepared by the palladium-catalyzed cross-coupling reaction of compound (9-1) with various coupling reagents in an inert solvent.

Specific examples of the coupling reagent include methylchlorozinc, methylbromozinc, methyliodozinc, methylboronic acid, methylboronic acid pinacol ester, and methyltrifluoroborane-potassium salt.

Examples of the inert solvent include THF, toluene, 1,2-dimethoxyethane, 1,4-dioxane, DMF, and a mixture thereof. Specific examples of the palladium reagent include tetrakis(triphenylphosphine)palladium (0), bis(dibenxylideneacetone)palladium (0), tris(dibenzyljdeneacetone)dipalladium (0), bis(tri-tert-butylphosphine)palladium (0), [1,1'-bis(diphenylphosphino)ferrocene]palladium (II) dichloride.

Specific examples of the base include an inorganic base such as potassium carbonate, sodium carbonate, cesium carbonate, potassium phosphate, potassium hydroxide, and sodium hydroxide.

The reaction temperature is typically 0° C. to 150° C., preferably 25° C. to 100° C., but is not limited thereto. The reaction time is typically 1 hour to 72 hours, preferably 1 hour to 24 hours.

Step 9-2: Preparation Process of Compound (9-3)

Compound (9-3) is prepared from compound (9-1) according to the process of Step 2-1.

Step 9-3: Preparation Process of Compound (9-4)

Compound (9-4) is prepared by hydrogenating vinyl group in compound (9-3) with a metal catalyst in an appropriate solvent.

Examples of the metal catalyst include palladium/carbon, Raney nickel, platinum oxide/carbon, and rhodium/carbon.

The amount of the metal catalyst to be used for compound (9-2) is typically 0.1% by weight to 1000% by weight, preferably 1% by weight to 100% by weight.

Examples of the solvent include an alcohol such as methanol; an ether such as tetrahydrofuran; and an ester such as ethyl acetate.

The hydrogen pressure is typically 1 atm to 100 atms, preferably 1 atm to 5 atms, The reaction temperature is typically 0° C. to 120° C., preferably 20° C. to 80° C., but is not limited thereto. The reaction time is typically 30 minutes to 72 hours, preferably 1 hour to 48 hours.

Compound (9-4) is also prepared by reacting compound (9-3) with hydrazine hydrate.

Preparation 10

One of the compounds of formula (1'), the compound of formula (10-4) is prepared according to, for example, the following process.

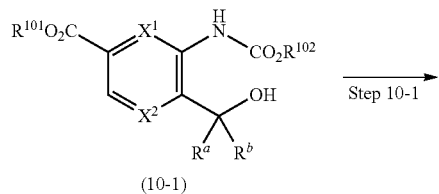

(10-1)

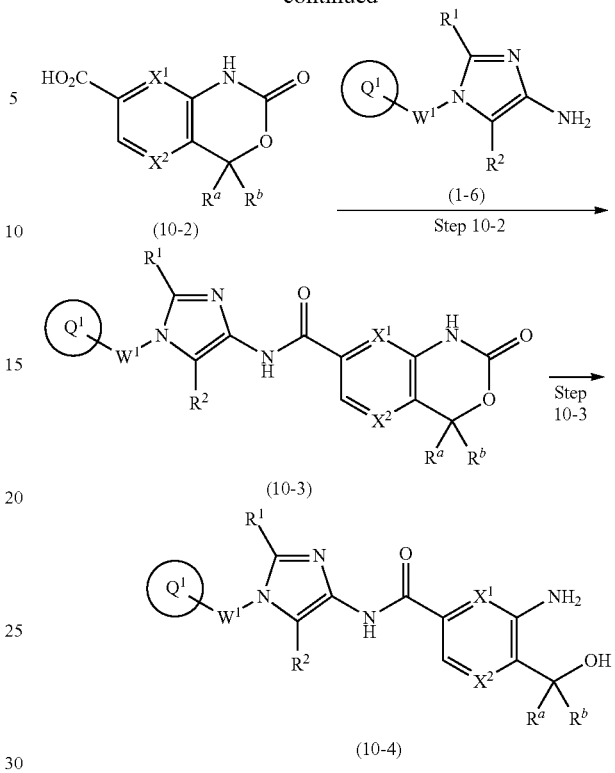

wherein $W^1$, $R^1$, $R^2$, and ring $Q^1$ are as defined in the above [1]; $X^1$ and $X^2$ are as defined in the above [25]; $R^{101}$ is $C_{1-6}$ alkyl group, $R^{102}$ is $C_{1-6}$ alkyl group, bnzyl group, and allyl group; and $R^a$ and $R^B$ are independently the same or different hydrogen atom or methyl group.

Compound (10-1) may be prepared according to, for example, the process of Preparation 2.

Step 10-1: Preparation Process of Compound (10-2)

Compound (10-2) is prepared by reacting compound (10-1) with an aqueous alkaline solution.

Examples of the aqueous alkaline solution include aqueous sodium hydroxide solution, aqueous potassium hydroxide solution, and aqueous lithium hydroxide solution, and the concentration thereof is typically 1-10 mol/L, preferably 1-5 mol/L.

Examples of the solvent used include methanol, ethanol, 2-propanol, THF, 1,4-dioxane, and a mixture thereof.

The reaction temperature is typically 0° C. to 100° C., preferably 0° C. to 50° C., but is not limited thereto. The reaction time is typically 10 minutes to 24 hours, preferably 30 minutes to 12 hours.

Step 10-2: Preparation Process of Compound (10-3)

Compound (10-3) is prepared from compounds (10-2) and (1-6) according to the process of Step 1-4.

Step 10-3: Preparation Process of Compound (10-4)

Compound (10-4) is prepared by reacting compound (10-3) with an aqueous alkaline solution.

Examples of the aqueous alkaline solution include aqueous sodium hydroxide solution, aqueous potassium hydroxide solution, and aqueous lithiuum hydroxide solution, and the concentration thereof is typically 1-10 mol/L, preferably 1-5 mol/L.

Examples of the solvent used include methanol, ethanol, 2-propanol, THF, 1,4-dioxane, and a mixture thereof.

The reaction temperature is typically 0° C. to 100° C., preferably 0° C. to 50° C., but is not limited thereto. The reaction time is typically 1 hour to 24 hours, preferably 1 hour to 6 hours.

Preparation 11

One of the compounds of formula (1'), the compound of formula (11-4) is prepared according to, for example, the following process.

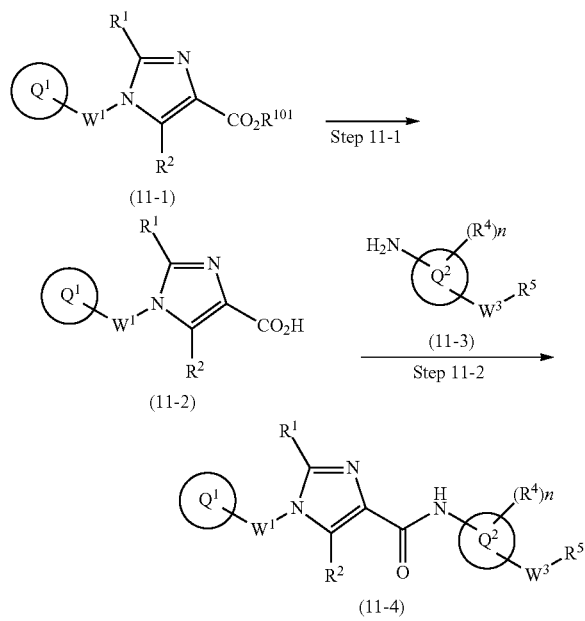

wherein $W^1$, $W^3$, $R^1$, $R^2$, $R^4$, $R^5$, n, and ring $Q^1$, and ring $Q^2$ are as defined in the above [1]; and $R^{101}$ is $C_{1-6}$ alkyl group.

Compound (11-1) may be a commercially available product or be prepared according to known synthesis processes (e.g. WO 2014/125444).

Step 11-1: Preparation Process of Compound (11-2)

Compound (11-2) is prepared by hydrolyzing compound (11-1) according to a similar process to a known process (e.g. Protective Groups in Organic Synthesis 3rd Edition (John Wiley & Sons, Inc.), Comprehensive Organic Transformation, by R. C. Larock, VCH publisher Inc., 1989).

Step 11-2: Preparation Process of Compound (11-4)

Compound (11-4) is prepared from compounds (11-2) and (11-3) according to the process of Step 1-4.

Preparation 12

One of the compounds of formula (1'), the compound of formula (12-5) is prepared according to, for example, the following process.

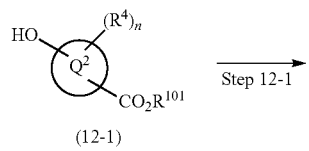

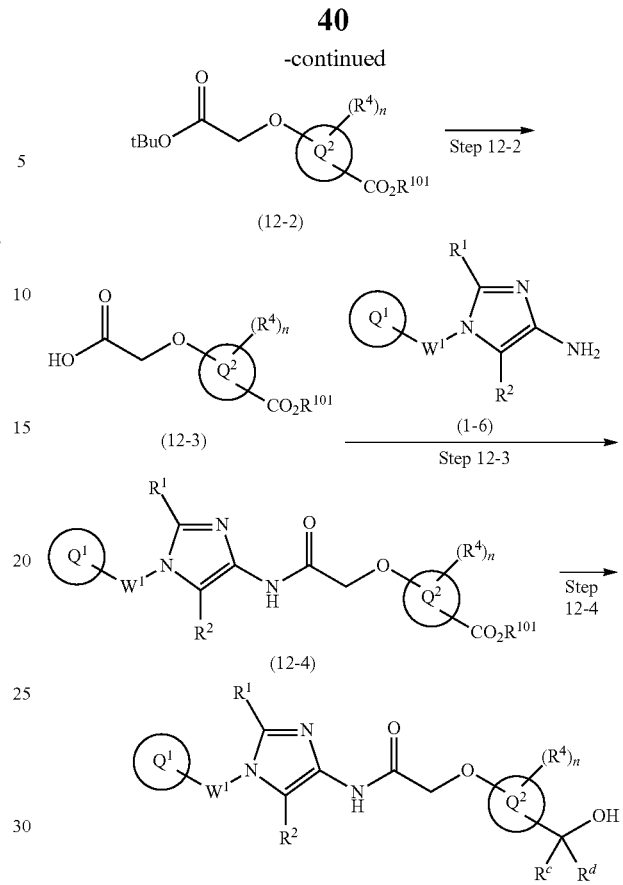

wherein $W^1$, $R^1$, $R^2$, $R^4$, n, ring $Q^1$, and ring $Q^2$ are as defined in the above [1]; $R^{101}$ is $C_{1-6}$ alkyl group; and $R^c$, and $R^d$ are independently the same or different hydrogen atom, deuterium atom, or methyl group.

Step 12-1: Preparation Process of Compound (12-2)

Compound (12-2) is prepared by reacting compound (12-1) with haloacetate in an inert solvent in the presence of a base.

Specific examples of the haloacetate include test-butyl chloroacetate, tert-butyl bromoacetate, and tert-butyl iodoacetate.

Examples of the base include potassium carbonate, sodium carbonate, cesium carbonate, potassium tert-butoxide, sodium hydride, sodium bis(trimethylsilyl)amide, lithium bis(trimethylsilyl)amide, potassium bis(trimethylsilyl)amide, and lithmium diisopropylamide.

Examples of the inert solvent include DMF, THF, acetonitrile, and a mixture thereof.

The reaction temperature is typically 25° C. to 150° C., preferably 70° C. to 100° C., but is not limited thereto. The reaction time is typically 10 minutes to 12 hours, preferably 20 minutes to 6 hours.

Step 12-2: Preparation Process of Compound (12-3)

Compound (12-3) is prepared by cleaving tert-butylester group in compound (12-2) under an acid condition.

Examples of the acid used in the deprotection step include hydrochloric acid, sulfuric acid, HBr, HI, and TFA.

Examples of the solvent used include methanol, ethanol, dichloromethane, 1,2-dichloroethane, THF, 1,4-dioxane, ethyl acetate, a mixture thereof.

The reaction temperature is typically 0° C. to 100° C., preferably 25° C. to 50° C., but is not limited thereto. The reaction time is typically 1 hour to 24 hours, preferably 2 hours to 12 hours.

Step 12-3: Preparation Process of Compound (12-4)

Compound (12-4) is prepared from compounds (12-3) and (1-6) according to the process of Step 1-4.

Step 12-4: Preparation Process of Compound (12-5)

Compound (12-5) is prepared from compound (12-4) according to the process of Step 8-2.

Preparation 13

The compound of formula (2-5) is also prepared from compound (2-1) according to, for example, the following process.

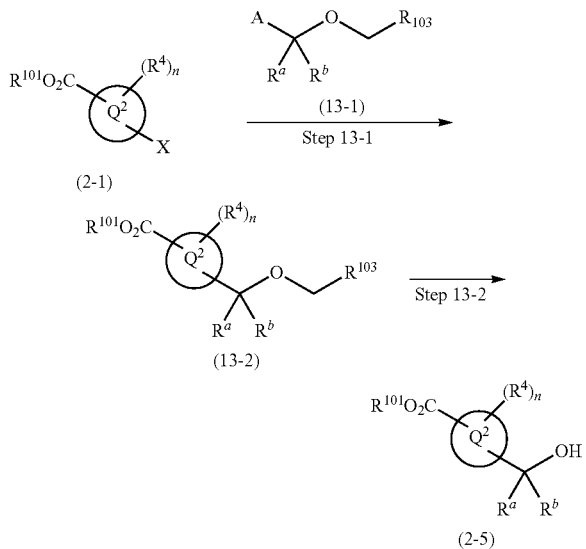

wherein $R^4$, n, and ring $Q^2$ are as defined in the above [1]; $R^{101}$ is $C_{1-6}$ alkyl group; $R^a$ and $R^b$ are independently the same or different hydrogen atom or methyl group; A is boronic acid, boronate, $BF_3K$, or $BF_3Na$; $R^{103}$ is optionally-substituted phenyl group; and X is halogen atom.

Step 13-1: Preparation Process of Compound (13-2)

Compound (13-2) is prepared by reacting compound (2-1) with compound (13-1) in an inert solvent in the presence of a palladium catalyst and a base.

Examples of the palladium catalyst include tetrakis(triphenylphosphine)palladium (0), bis(dibenzylideneacetone)palladium (0), tris(dibenzylideneacetone)dipalladium (0), bis(tri-tert-butylphosphine)palladium (0), [1,1'-bis(diphenylphosphino)ferrocene]palladium (II) dichloride.

Examples of the base include sodium carbonate, potassium carbonate, cesium carbonate, potassium phosphate, sodium hydroxide, and potassium hydroxide.

Examples of the inert solvent include 1,4-dioxane, THF, 1,2-dimethoxyethane, water, and a mixture thereof.

The reaction temperature is typically 50° C. to 200° C., preferably 80° C. to 150° C., but is not limited thereto. The reaction time is typically 1 hour to 48 hours, preferably 6 hours to 18 hours, Step 13-2: Preparation Process of Compound (2-5)

Compound (2-5) is prepared by hydrogenating benzyl group in compound (13-2) with a metal catalyst in an appropriate solvent to cleave the group.

Examples of the metal catalyst include palladium/carbon, Raney nickel, platinum oxide/carbon, and rhodium/carbon.

The amount of the metal catalyst to be used for compound (13-2) is typically 0.1% by weight to 1000% by weight, preferably 1% by weight to 100% by weight.

Examples of the solvent include an alcohol such as methanol; an ether such as tetrahydrofuran; and an ester such as ethyl acetate.

The hydrogen pressure is typically 1 atm to 100 atms, preferably 1 atm to 5 atms.

The reaction temperature is typically 0° C. to 120° C., preferably 20° C. to 80° C., but is not limited thereto. The reaction time is typically 30 minutes to 72 hours, preferably 1 hour to 48 hours.

Also, when $R^{103}$ is phenyl group substituted with group(s) such as 4-methoxy group and 2,4-dimethoxy group, compound (2-5) is prepared by reacting compound (13-2) with an acid.

Examples of the acid include TFA, formic acid, hydrochloric acid, sulfuric acid, p-toluenesulfonic acid, methanesulfonic acid, and (±) 10-camphorsulfonic acid.

Examples of the solvent used include dichloromethane, 1,2-dichloroethane, 1,4-dioxane, THF, toluene, ethyl acetate, methanol, ethanol, 2-propanol, and a mixture thereof.

The reaction temperature is typically 0° C. to 100° C., preferably 25° C. to 50° C., but is not limited thereto. The reaction time is typically 30 minutes to 12 hours, preferably 1 hour to 9 hours.

Preparation 14

One of the compounds of formula (1'), the compound of formula (14-3) is prepared according to, for example, the following process.

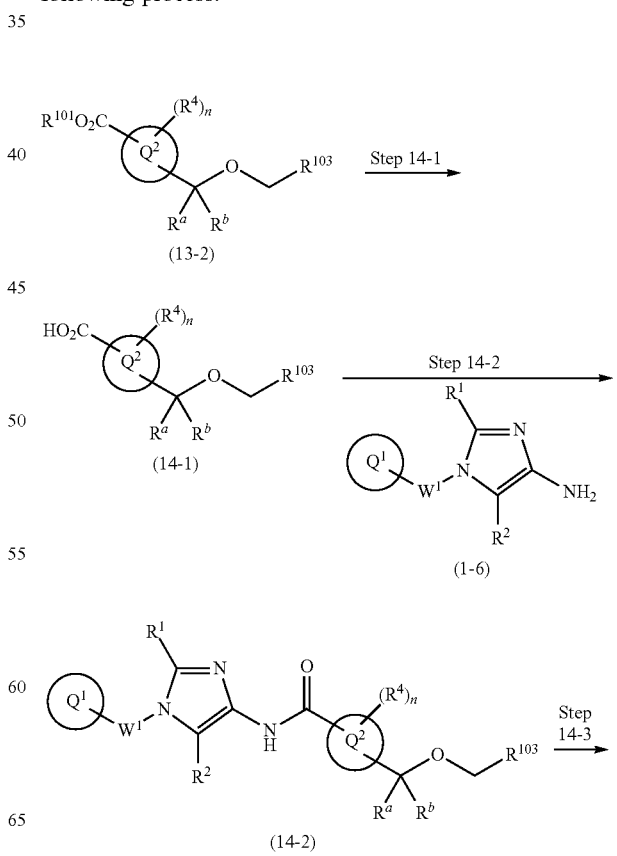

-continued

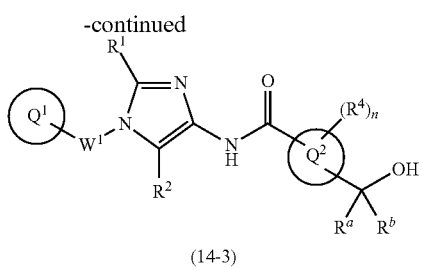

(14-3)

wherein $W^1$, $R^1$, $R^2$, $R^4$, n, ring $Q^1$, and ring $Q^2$ are as defined in the above [1]; $R^{101}$ is $C_{1-6}$ alkyl group; $R^a$ and $R^b$ are independently the same or different hydrogen atom or methyl group; and $R^{103}$ is optionally-substituted phenyl group.

Step 14-1: Preparation Process of Compound (14-1)

Compound (14-1) is prepared by hydrolyzing compound (13-2) according to a similar process to a known process (e.g. Protective Groups in Organic Synthesis 3rd Edition. (John Wiley & Sons, Inc.), Comprehensive Organic Transformation, by R. C. Larock, VCH publisher Inc., 1989).

In this case, compound (14-1) may be also used in the next reaction without any isolation.

For example, compound (13-2) is hydrolyzed according to the above process to neutralize the reaction solution and then the solvent is removed to give compound (14-1), and the resulting compound may be used in Step 14-2.

Step 14-2: Preparation Process of Compound (14-2)

Compound (14-2) is prepared from compounds (14-1) and (1-6) according to the process of Step 1-4.

Step 14-3: Preparation Process of Compound (14-3)

Compound (14-3) is prepared by hydrogenating benzyl group in compound (14-2) with a metal catalyst is an appropriate solvent to cleave the group.

Examples of the metal catalyst include palladium/carbon, Raney nickel, platinum oxide/carbon, and rhodium/carbon.

The amount of the metal catalyst to be used for compound (14-2) is typically 0.1% by weight to 1000% by weight, preferably 1% by weight to 100% by weight.

Examples of the solvent include an alcohol such as methanol; an ether such as tetrahydrofuran; and an ester such as ethyl acetate.

The hydrogen pressure is typically 1 atm to 100 atms, preferably 1 atm to 5 atms.

The reaction temperature is typically 0° C. to 120° C., preferably 20° C. to 80° C., but is not limited thereto. The reaction time is typically 30 minutes to 72 hours, preferably 1 hour to 48 hours.

Also, when $R^{103}$ is phenyl group substituted with group such as 4-methoxy group and 2,4-dimethoxy group, compound (14-3) is prepared by reacting compound (14-2) with an acid.

Examples of the acid include TFA, formic acid, hydrochloric acid, sulfuric acid, p-toluenesulfonic acid, methanesulfonic acid, and (±) 10-camphorsulfonic acid.

Examples of the solvent used include dichloromethane, 1,2-dichloroethane, 1,4-dioxane, THF, toluene, ethyl acetate, methanol, ethanol, 2-propanol, and a mixture thereof.

The reaction temperature is typically 0° C. to 100° C., preferably 25° C. to 50° C., but is not limited thereto. The reaction time is typically 30 minutes to 12 hours, preferably 1 hour to 9 hours.

Preparation 15

One of the compounds of formula (1'), the compound of formula (14-2) is prepared according to, for example, the following process.

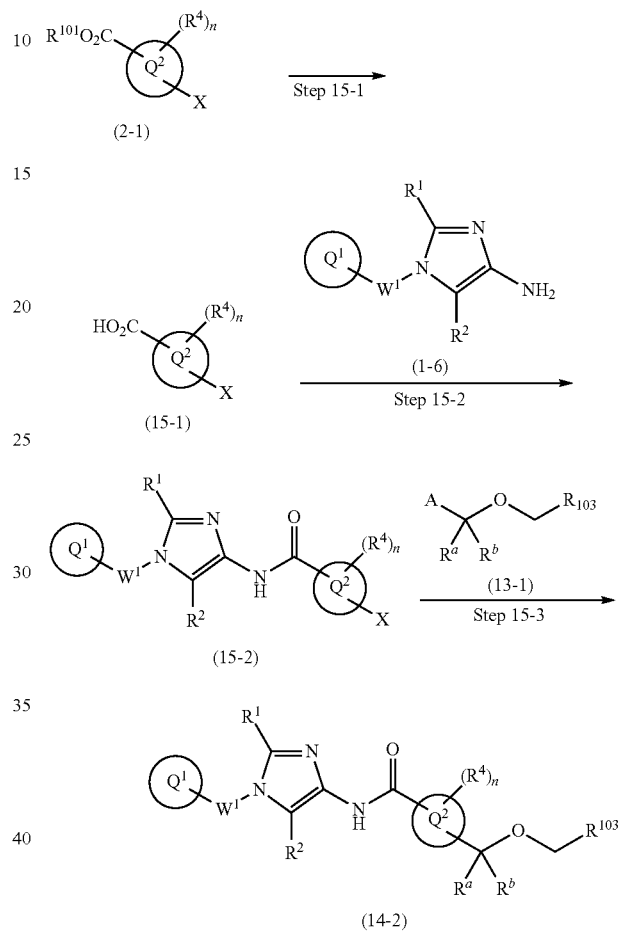

wherein $W^1$, $R^1$, $R^2$, $R^4$, n, ring $Q^1$, and ring $Q^2$ are as defined in the above [1]; $R^{101}$ is $C_{1-6}$ alkyl group; and $R^a$, and $R^b$ are independently the same or different hydrogen atom or methyl group; X is halogen atom; A is boronic acid, boronate, $BF_3K$, or $BF_3Na$; and $R^{103}$ is optionally-substituted phenyl group.

Step 15-1: Preparation Process of Compound (15-1)

Compound (15-1) is prepared by hydrolyzing compound (2-1) according to a similar process to a known process (e.g. Protective Groups in Organic Synthesis $3^{rd}$ Edition (John Wiley & Sons, Inc.), Comprehensive Organic Transformation, by R. C. Larock, VCH publisher Inc., 1989).

In this case, compound (15-1) may be also used in the next reaction without any isolation.

For example, compound (2-1) is hydrolyzed according to the above process to neutralize the reaction solution and then the solvent is removed to give compound (15-1), and the resulting compound may be used in Step 15-2.

Step 15-2: Preparation Process of Compound (15-2)

Compound (15-2) is prepared from compounds (15-1) and (1-6) according to the process of Step 1-4.

Step 15-3: Preparation Process of Compound (14-2)

Compound (14-2) is prepared by reacting compound (15-2) with compound (13-1) in an inert solvent in the presence of a palladium catalyst and a base.

Examples of the palladium catalyst include tetrakis(triphenylphosphine)palladium (0), bis(dibenzylideneacetone)palladium (0), tris(dibenzylideneacetone)dipalladium (0), bis(tri-tert-butylphosphine)palladium (0), [1,1'-bis(diphenylphosphino)ferrocene]palladium (II) dichloride.

Examples of the base include sodium carbonate, potassium carbonate, cesium carbonate, potassium phosphate, sodiuum hydroxide, ant potassium hydroxide.

Examples of the inert solvent include 1,4-dioxane, THF, 1,2-dimethoxyethane, water, and a mixture thereof.

The reaction temperature is typically 50° C. to 200° C., preferably 80° C. to 150° C., but is not limited thereto. The reaction time is typically 1 hour to 48 hours, preferably 6 hours to 18 hours.

Preparation 16

One of the compounds of formula (1'), the compound of formula (1-7) is prepared according to, for example, the following process.

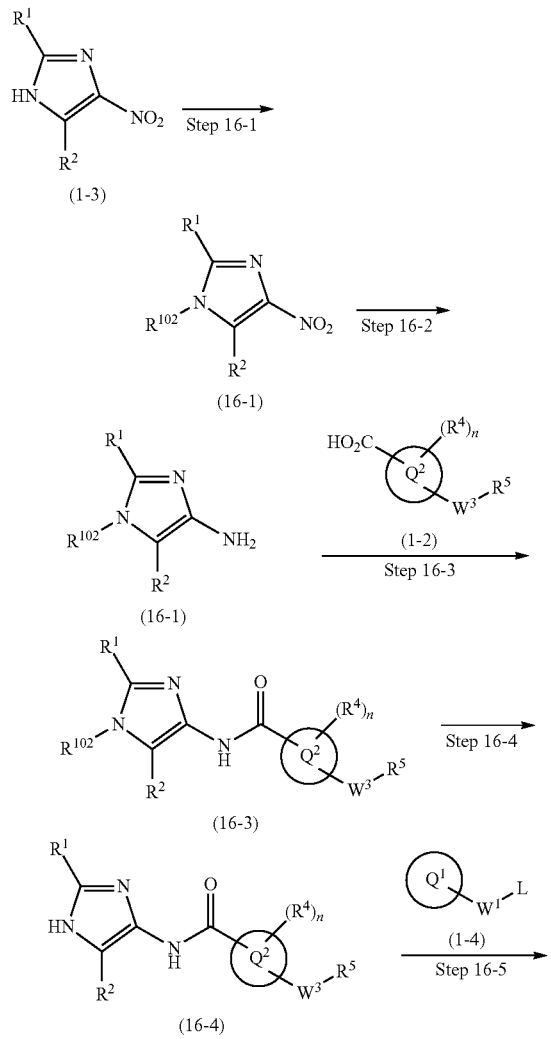

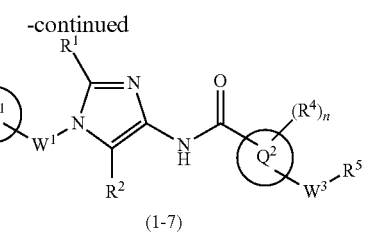

wherein $W^1$, $W^3$, $R^1$, $R^2$, $R^4$, $R^5$, n, ring $Q^1$, and ring $Q^2$ are as defined in the above [1]; $R^{102}$ is protective group; and L is a leaving group (such as iodine atom, bromine atom, chlorine atom, and substituted sulfonyloxy group (such as methanesulfonyloxy group and p-toluenesulfonyloxy group)).

Step 16-1: Preparation Process of Compound (16-1)

Compound (16-1) is prepared by introducing a protective group into nitrogen atom in the 1-position of imidazole group in compound (1-3) in an inert solvent. Examples of the protective group include 2-(trimethylsilyl)ethoxymethyl, benzyloxycarbonyl, tert-butoxycarbonyl, acetyl, and benzyl.

For example, when 2-(trimethylsilyl)ethoxymethyl group introduced, compound (16-1) is prepared by reacting compound (1-3) with 2-(trimethylsilyl)ethoxymethyl chloride in an inert solvent in the presence of a base.

Examples of the base include potassium carbonate, sodium carbonate, cesium carbonate, potassium tert-butoxide, sodium hydride, sodium bis(trimethylsilyl)amide, lithium bis(trimethylsilyl)amide, potassium bis(trimethylsilyl)amide, and lithium diisoproylamide.

Examples of the inert solvent include DMF, THF, acetonitrile, and a mixture thereof.

The reaction temperature is typically 0° C. to 150° C., preferably 0° C. to 100° C., but is not limited thereto. The reaction time is typically 10 minutes to 24 hours, preferably 20 minutes to 6 hours.

Step 16-2: Preparation Process of Compound (16-2)

Compound (16-2) is prepared from compound (16-1) according to the process of Step 1-3.

Step 16-3: Preparation Process of Compound (16-3)

Compound (16-3) is prepared from compounds (16-2) and (1-2) according to the process of Step 1-4.

Step 16-4: Preparation Process of Compound (16-4)

Compound (16-4) is prepared by cleaving the protective group in nitrogen atom of imidazole group in compound (16-3) in an inert solvent.

For example, when 2-(trimethylsilyl)ethoxymethyl group is cleaved, compound (16-4) is prepared by reacting compound (16-3) with an acid or a fluorinating reagent.

Examples of the acid include TFA, formic acid, hydrochloric acid, sulfuric acid, p-toluenesulfonic acid, methanesulfonic acid, and (±) 10-camphorsulfonic acid.

Examples of the fluorinating reagent include tetrabutylammonium fluoride.

Examples of the solvent used include dichloromethane, 1,2-dichloroethane, 1,4-dioxane, THF, toluene, ethyl acetate, methanol, ethanol 2-propanol, and a mixture thereof.

The reaction temperature is typically 0° C. to 150° C., preferably 0° C. to 50° C., but is not limited thereto. The reaction time is typically 5 minutes to 24 hours, preferably 1 hour to 9 hours.

Step 16-5: Preparation Process of Compound (1-7)

Compound (1-7) is prepared from compounds (16-4) and (1-4) according to the process of Step 1-2.

The intermediates and desired compounds in the above preparations may be isolated and purified by a conventional purification method in organic synthetic chemistry such as neutralization, filtration, extraction, washing, drying, concentration, recrystailization, and each type of chromatography. The intermediates may be also used in the next reaction. without any specific purification.

An optically-active product of the present. compound can be prepared from an optically-active starting material or intermediate, or by the optical resolution of the racemate of a final product. The optical resolution method includes a physical separation method with optically-active column, and a chemical separation method such as a fractional crystallization method. A diastereomer of the present compound can be prepared by, for example, a fractional crystallization method.

The pharmaceutically acceptable salt of the compound of formula (1') can be prepared by, for example, mixing the compound of formula (1') with a pharmaceutically acceptable acid in a solvent such as water, methanol, ethanol, and acetone.

The present compound is used as, for example, an anti-tumor agent (anti-cancer agent). The applicable cancer type includes hematopoietic tumor and solid cancer, but is not limited thereto. Specific examples of the hematopoietic tumor include acute leukemia, chronic lymphatic leukemia, chronic myelocytic leukemia, polycythemia vera, malignant lymphoma, and myeloma, and specific examples of the solid cancer include brain tumor, head and neck cancer, esophageal cancer, thyroid cancer, small-cell lung cancer, non-small cell lung cancer, breast cancer, stomach cancer, gallbladder or bile duct cancer, liver cancer, pancreatic cancer, colon cancer, rectal cancer, ovarian cancer, chorioepithelioma, endbmetrial cancer, cervical cancer, urothelial cancer, renal cell cancer, prostate cancer, testicular tumor, Wilms' tumor, malignant melanoma, neuroblastoma, osteosarcoma, Ewing's sarcoma, and soft tissue sarcoma.

The anti-tumor agent is used for the prophylaxis and/or treatment of a cancer, and is expected to produce the reduction or disappearance of carcinoma or inhibit the growth of carcinoma down to a certain level. The "prophylaxis" used herein means the administration of the active ingredient of the present invention to a healthy subject who does not develop a disease. For example, the prophylaxis is intended to prevent the development of a disease. The "treatment" used herein means the administration of the active ingredient of the present invention to a person diagnosed with the development of a disease by a doctor (i.e. a patient). For example, the treatment is intended to alleviate a disease or symptom thereof, inhibit the growth of carcinoma, or improve the condition of a patient to the previous condition before a disease is developed. Also, even if an anti-tumor agent is administered for the purpose of preventing the worsening of a disease or symptom thereof or the growth of carcinoma, the administration is referred to as "treatment" when the subject to be administered is a patient.

The present compound has any remarkable effects for inhibiting self-renewal ability of CSCs, and thus is expected to be useful as a novel anti-tumor agent for inhibiting the persistent proliferation, metastasis, and recurrence of malignant tumors derived from CSCs.

The present compound may be formulated into a suitable dosage form and administered orally or parenterally. Examples of the dosage form include a tablet, a capsule, a powder, a granule, a solution, a suspension, arm injection, a patch, and a poultice, but are not limited thereto. The preparation is formulated using pharmaceutically acceptable addjtivet according to a known method.

As appropriate, an additive such as an excipient, a disintegrant, a binder, a fluidizer, a lubricant, a coating agent, a solubilizer, a solubilizing agent, a thickening agent, a dispersant, a stabilizing agent, a sweetening agent, and a flavor may be used. Specific examples thereof include lactose, mannitol, crystalline cellulose, low substituted hydroxypropylcellulose, corn starch, partly pregelatinized. starch, carmellose calcium, croscarmellose sodium, hydroxypropylcellulose, hydroxypropylmethylcellulose, polyvinylalcohol, magnesium stea rate, sodium stearyl fumarate, polyethylene glycol, propylene glycol, titanium oxide, and talc.

The present compound may be used in combination with another drug(s) to enhance the therapeutic effect thereof and/or reduce side effects thereof. Specifically, the present compound can be used in combination with a drug such as a hormone therapeutic drug, a chemotherapeutic drug, an immunotherapeutic drug or a cell growth factor and a drug for inhibiting a receptor effect thereof. Hereinafter, a drug which can be used in combination with the present compound is referred to as "combined medicine".

Examples of the combined medicine include an anti-cancerous alkylating agent, an anti-cancerous antimetabolite, an anti-cancerous antibiotic, a plant-based anti-cancer agent, an anti-cancerous platinum coordination compound, an anti-cancerous camptothecin derivativ an anti-cancerous tyrosine kinase inhibitor, a serine-threonine kinase, a phospholipid kinase, a monoclonal antibody, an interferon, a biological response modifier, a hormone preparation, an immune checkpoint inhibitor, an epigenetics-related molecule inhibitor, a post-translational protein modification inhibitor, and other anti-cancer agents.

The administration timing of the present compound and a combined medicine is not necessarily limited, and they may be administered simultaneously or administered with time -interval to a subject. In addition, the present compound and a combined medicine may be used in the form of a combination drug. The dosage of the combined medicine may be optionally determined based on the dosage in the clinical use. Also, the mixing ratio of the present compound and a combined medicine may be optionally determined depending on the subject to be administered, the administration route, the disease to be treated, the symptom, and a combination thereof. For example, when the subject is human, the combined medicine may be used in an amount of 0.01 to 100 parts by weight relative to 1 part by weight of the present compound. In addition, a drug (a combined medicine) such as an antiemetic, a sleep inducing agent, and an anticonvulsant may be used in combination with the present compound to inhibit side effects thereof.

The dosage can vary according to each compound and various conditions such as patient's disease, age, body weight, sex, symptom, and administration route. Typically, the present compound is administered to an adult (body weight: 50 kg) at a dose of 0.1 to 1000 mg/day, preferably at a dose of 0.1 to 300 mg/day, which may be administered once a day or 2 or 3 times a day. In addition, the present compound may be administered once in several days to several weeks.

EXAMPLES

Hereinafter, the invention is illustrated in more detail with Reference Examples, Examples, and Test Examples, but the invention should not be limited thereto. The compound names as shown in the following Reference Examples ant Examples do not necessarily follow the IUPAC nomenclature system.

The following abbreviations may be used herein.
THF: tetrahydrofuran
TFA: trifluoroacetic acid
$(Boc)_2O$: di-tert-butyl dicarbonate
DBU: 1,8-diazabicyclo[5.4.0]-7-undecene
DMF: N,N-dimethylformamide
DME: 1,2-dimethoxyethane
DIEA: N,N-diisopropylethylamine
DMAP: N,N-dimethyl-4-aminopyridine
EDCI: 1-ethyl-3-(3-dimethylaminopropyl)carbodiimide
EDCI.HCl: 1-ethyl-3-(3-dimethylaminopropyl)carbodiimide hydrochloride
HOBt: 1-hydroxybenzotriazole
$HOBt.H_2O$: 1-hydroaybenzotriazole monohydrate
NBS: N-bromosuccinimide
TBSCl: tert-butyldimethylchlorosilane
Me: methyl
Et: ethyl
Ac: acetyl
Boc: tert-butoxycarbonyl
SEM: 2-(trimethylsilyl)ethoxymethyl
Rt: retention time
LC/MS analysis condition in the compound identification is as follows.
LC/MS measurement:
Detection device: ACQUITY® SQ deteceter (Waters)
HPLC: ACQUITY UPLC® system
Column: Waters ACQUITY UPLC® BEH C18 (1.7 µm, 2.1 mm×30 mm)
Solvent: A solution: 0.06% formic acid/$H_2O$, B solution: 0.06% formic acid/MeCN
Gradient condition: 0.0-1.3 min Linear gradient from B 2% to 96%
Flow rate: 0.8 mL/min
UV: 220 nm and 254 nm Reference Example 1

4-Nitro-1-[3-(trifluoromethyl)benzyl]-1H-imidazole

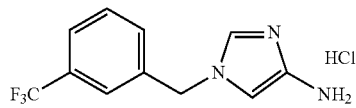

A mixture of 4-nitro-1H-imidazole (35.8 g), 3-trifluoromethylbenzyl bromide (75.7 g), potassium iodide (0.131 g), potassium carbonate (48.1 g), and acetonitrile (270 mL) was stirred at 80° C. for 5 hours. The reaction mixture was cooled to room temperature, and then water was added thereto, and the mixture was extracted with ethyl acetate. The organic layer was washed with brine, dried over magnesium sulfate, filtered, and then concentrated in vacuo. To the resulting solid was added diisopropyl ether (300 mL), and the mixture was stirred at room temperature for 1 hour. The resulting precipitate was collected on a filter, washed with diisopropyl ether, and dried at 50° C. in vacuo to give the title compound (69.0 g).
LC-MS ($[M+H]^+$/Rt (min)): 272.1/0.835

Reference Examples 2-3

According to the process of Reference Example 1, the compounds of Reference Examples 2-3 were prepared from each corresponding starting compound.

| Reference Examples | chemical structural formula | LC-MS: $[M + H]^+$/Rt (min) |
|---|---|---|
| 2 | | 238.1/0.776 |
| 3 | | 258.1/0.742 |

Reference Example 4

1-[3-(Trifluoromethyl)benzyl]-1H-imidazole-4-amine hydrochloride

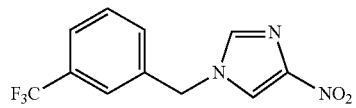 [SMILES: O=[N+]([O-])c1cn(Cc2cccc(C(F)(F)F)c2)cn1]

To the compound of Reference Example 1 (34.0 g) and rhodium-activated carbon (5%, 17.0 g) was added ethyl acetate (330 mL), and the mixture was stirred at room temperature under hydrogen atmosphere for 14 hours. The reaction mixture was filtered through Celite®, wahsed with ethyl acetate (50 mL×4), and then to the filtrate was added hydrogen chloride (4 mol/L in ethyl acetate, 38.0 mL). The filtrate was concentrated in vacuo, and then to the resulting crude product were added ethyl acetate (200 mL) and hexane (200 mL), and the mixture was stirred at room temperature for 10 minutes. The resulting precipitate was collected on a filter and washed with hexane/ethyl acetate (1/1, 20 mL×3), and then the resutling solid was dried at 40° C. in vacuo to give the title compound (31.4 g).
LC-MS ($[M+H]^+$/Rt (min)): 242.1/0.548

Reference Examples 5-6

According to the process of Reference Example 4, the compounds of Reference Examples 5-6 were prepared from each corresponding starting compound.

| Reference Examples | chemical structural formula | LC-MS: $[M + H]^+$/Rt (min) |
|---|---|---|
| 5 | | 208.1/0.460 |
| 6 | | 228.1/0.473 |

Reference Example 7

Methyl 6-({1-[3-(trifluoromethyl)benzyl]-1H-imidazol-4-yl}carbamoyl)nicotinate

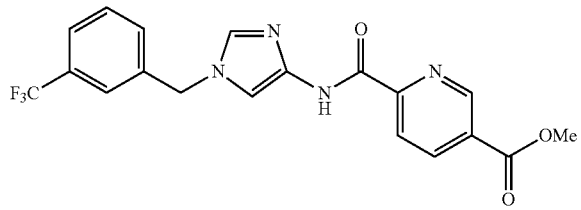 [SMILES: COC(=O)c1ccc(C(=O)Nc2cn(Cc3cccc(C(F)(F)F)c3)cn2)nc1]

To a suspension of the compound of Reference Example 4 (300 mg) in DMF (5 mL) were added 5-(methoxycarbonyl)picolinic acid (235 mg), EDCl.HCl (248 mg), HOBt (175 mg), and N,N-diisopropylethylamine (0.279 mL), and the mixture was stirred at room temperature for 2 hours. To the reaction mixture were added water and saturated aqueous sodium carbonate solution, and the mixture was extracted with ethyl acetate. The organic layer was washed with saturated aqueous sodium carbonate solution and then brine, dried over sodium sulfate, filtered, and concentrated in vacuo. The residue was purified by silica gel column chromatography (chloroform/methanol) to give the title compound (281 mg).
LC-MS ([M+H]$^+$/Rt (min)): 404.9/0.901

Reference Examples 8-19

According to the process of Reference Example 7, the compounds of Reference Examples 8-19 were prepared from each corresponding starting compound.

| Reference Examples | chemical structural formula | LC-MS: [M + H]$^+$/Rt (min) |
|---|---|---|
| 8 | | 404.9/0.780 |
| 9 | | 443.1/0.960 |
| 10 | | 415.2/0.992 |
| 11 | | 503.1/1.017 |
| 12 | | 411.2/0.897 |
| 13 | | 395.2/0.863 |

| Reference Examples | chemical structural formula | LC-MS: [M + H]⁺/Rt (min) |
|---|---|---|
| 14 | | 395.2/0.888 |
| 15 | | 415.1/0.915 |
| 16 | | 431.1/0.942 |
| 17 | | 415.1/0.849 |
| 18 | | 489.0/0.991 |
| 19 | | 401.1/0.967 |

Reference Example 20

6-Ethenyl-5-fluoro-N-{1-[3-(trifluoromethyl)benzyl]-1H-imidazol-4-yl}nicotinamide

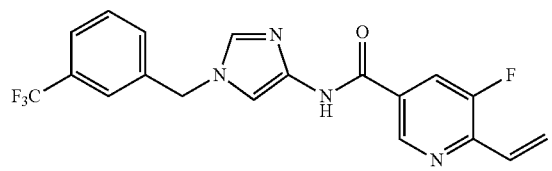 [SMILES: C=Cc1ncc(C(=O)Nc2cn(Cc3cccc(C(F)(F)F)c3)cn2)cc1F]

To a solution of the compound of Reference Example 9 (300 mg) in a mixture of 1,4-dioxane (5 mL)/water (0.5 mL) were added vinylboronic acid pinacol ester (0.232 mL), tetrakis(triphenyiphosphine)pailadium (78 mg), and potassium carbonate (281 mg), and the mixture was stirred under microwave irradiation at 120° C. for 1 hour. The reaction mixture was cooled to room temperature, and water was added thereto, and then the mixture was extracted with ethyl acetate. The organic layer was washed with brine, dried over sodium sulfate, filtered, and then concentrated in vacuo. The residue was purified by silica gel column chromatography (hexane/ethyl acetate, ethyl acetate/methanol) to give the title compound (122 mg).

LC-MS ([M+H]⁺/Rt (min)): 391.2/0.936

Reference Examples 21-30

According to the process of Reference Example 20, the compounds of Reference Examples 21-30 were prepared from each corresponding starting compound.

| Reference Examples | chemical structural formula | LC-MS: [M + H]+/Rt (min) |
|---|---|---|
| 21 | | 407.2/1.004 |
| 22 | | 451.2/1.017 |
| 23 | | 403.3/0.895 |
| 24 | | 387.2/0.767 |
| 25 | | 387.2/0.815 |
| 26 | | 407.2/0.894 |
| 27 | | 379.2/0.897 |
| 28 | | 363.2/0.834 |
| 29 | | 437.1/0.989 |

| Reference Examples | chemical structural formula | LC-MS: [M + H]+/Rt (min) |
|---|---|---|
| 30 | 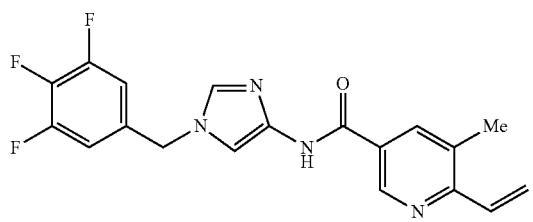 [SMILES: C=Cc1ncc(C(=O)Nc2cn(Cc3cc(F)c(F)c(F)c3)cn2)cc1C] | 393.2/0.976 |

Reference Example 31

6-Ethenyl-5-methyl-N-[1-(3,4,5-trifluorobenzyl)-1H-imidazol-4-yl]nicotinamide

To a solution of the compound of Reference Example 29 (200 mg) in THF (4 mL) were added bis (tri-tert-butylphosphine)palladium (0) (23 mg) and methylzinc chloride (2 mol/L THF, 0.69 mL), and the mixture was stirred at room temperature for 2 hours. To the reaction mixture were added saturated aqueous ammonium chloride solution and water, and the mixture was extracted with ethyl acetate. The organic layer was washed with saturated aqueous sodium carbonate solution and brine, dried over sodium sulfate, filtered, and then concentrated in vacuo. The residue was purified by amino silica gel column chromatography (chloroform/methanol) to give the title compound (135 mg).
LC-MS ([M+H]+/Rt (min)): 373.2/0.824

Reference Example 32

6-(1,2-Dihydroxyethyl)-5-methoxy-N-{1-[3-(trifluoromethyl)benzyl]-1H-imidazol-4-yl}nicotinamide To a solution of the compound of Reference Example 23 (490 mg) in acetone (5 mL)/water (2.5 mL) were added N-methylmorpholine-N-oxide (285 mg) and osmium tetroxide (2.5 wt % in tert-butanol, 0.764 mL), and the mixture was stirred at room temperature for 24 hours. To the reaction mixture were then added saturated aqueous sodium thiosulfate solution and water, and the mixture was extracted with ethyl acetate. The organic layer was washed with brine, dried over sodium sulfate, filtered, and then concentrated in vacuo. The residue was purified by amino silica gel column chromatography (chloroform/methanol) to give the title compound (142 mg).
LC-MS ([M+H]+/Rt (min)): 437.3/0.684

Reference Examples 33-38

According to the process of Reference Example 32, the compounds of Reference Examples 33-38 were prepared from each corresponding starting compound.

| Reference Examples | chemical structural formula | LC-MS: [M + H]+/Rt (min) |
|---|---|---|
| 33 | 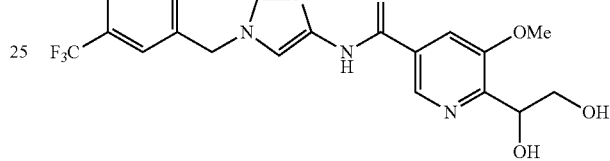 | 421.2/0.642 |

| Reference Examples | chemical structural formula | LC-MS: [M + H]⁺/Rt (min) |
|---|---|---|
| 34 | | 421.2/0.656 |
| 35 | | 441.2/0.710 |
| 36 | | 397.2/0.647 |
| 37 | | 471.2/0.702 |
| 38 | | 407.2/0.612 |

Reference Example 39-1

6-(Chloromethyl)-N-{1-[3-(trifluoromethyl)benzyl]-1H-imidazol-4-yl}nicotinamide

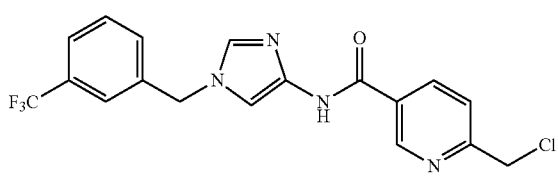 [SMILES: O=C(Nc1cn(Cc2cccc(C(F)(F)F)c2)cn1)c1ccc(CCl)nc1]

To a suspension of the compound of Example 12 (400 mg) in THF were added lithium chloride (90 mg), N,N-diisopropylethylamine (0.366 mL) and then methanesulfonyl chloride (0.165 mL), and the mixture was stirred at room temperature for 4 hours. Lithium chloride (45 mg), N,N-diisopropylethylamine (0.183 ml), and methanesulfonyl chloride (0.083 mL) were added thereto, and then the mixture was additionally stirred at room temperature for 17 hours. To the reaction mixture was added water, and the mixture was extracted with ethyl acetate. The organic layer was washed with brine, dried over sodium sulfate, filtered, and then concentrated in vacuo. The residue was purified by silica gel column chromatography (chloroform/methanol) to give the title compound (269 mg).

LC-MS ([M+H]⁺/Rt (min)): 395.2/0.835

Reference Example 39-2

6-[(Di-tert-butoxycarbonyl)aminomethyl]-N-{1-[3-(trifluoromethyl)benzyl]-1H-imidazol-4-yl}nicotinamide

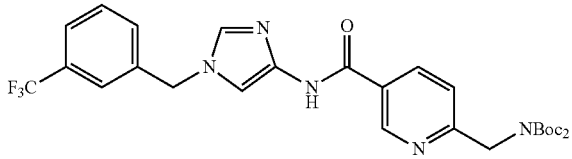

To a solution of di-tert-butyl iminodicarbonate (586 mg) in DMF (3 ml) was added sodium hydride (118 mg), and the mixture was stirred at room temperature for 25 minutes. To the reaction mixture was added a solution of the compound of Reference Example 39-1 obtained by the above process (213 mg) in DMF (6 mL), and the mixture was stirred at room temperature for 2 hours and then at 50° C. for 4 hours. The mixture was cooled to room temperature, and to the reaction mixture was added saturated aqueous ammonium chloride solution, and then the mixture was extracted with ethyl acetate. The organic layer was washed with brine, dried over sodium sulfate, filtered, and then concentrated in vacuo. The residue was purified by silica gel column chromatography (chloroform/methanol) to give the title compound (119 mg).
LC-MS ([M+H]$^+$/Rt (min)): 576.5/1.080

Reference Example 40

Ethyl 6-(ethoxymethyl)-nicotinate

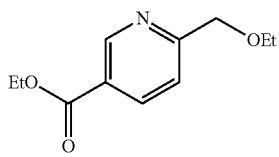 [SMILES: CCOCc1ccc(C(=O)OCC)cn1]

To ethanol (20 mL) was added sodium (237 mg) over 1 hour, and ethyl 6-(bromomethyl)-nicotinate (500 mg) was added thereto, and then the mixture was stirred at room temperature overnight. The reaction mixture was concentrated in vacuo to remove the ethanol, and saturated aqueous sodium hydrogen carbonate solution was added thereto, and then the mixture was extracted with chloroform. The organic layer was dried over anhydrous sodium sulfate, filtered, and concentrated in vacuo. The residue was purified by silica gel column chromatography (chloroform/methanol) to give the title compound (159 mg).
LC-MS ([M+H]$^+$/Rt (min)): 210.3/0.800

Reference Example 41-1

Methyl 5-[(tert-butoxycarbonyl)amino]-6-chloro-nicotinate

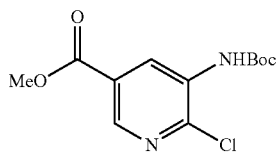 [SMILES: COC(=O)c1cnc(Cl)c(NC(=O)OC(C)(C)C)c1]

To solution of methyl 5-amino-6-chloro-nicotinate (325 mg) in THF (10 mL) were added di-tert-butyl dicarbonate (760 mg) and DHAP (11 mg), and the mixture was stirred at room temperature for 15.5 hours. Additional di-tert-butyl dicarbonate (38 mg) was added thereto, and the mixture was stirred at 60° C. for 45 minutes. The mixture was cooled to room temperature, and then the solvent was removed. To the residue were added methanol (5 mL) and potassium carbonate (481 mg), and the mixture was stirred at room temperature for 2.5 hours. Saturated aqueous ammonium chloride solution was added thereto, and the mixture was extracted with ethyl acetate. The organic layer was washed with brine, dried over anhydrous sodium sulfate, filtered, and then concentrated in vacuo. The residue was purified by silica gel column chromatography (hexane/ethyl acetate) to give the title compound (321 mg).
LC-MS ([M+H]$^+$/Rt (min)): 287.1/0.985

Reference Example 41-2

Methyl 5-[(tert-butoxycarbonyl)amino]-6-ethenyl-nicotinate

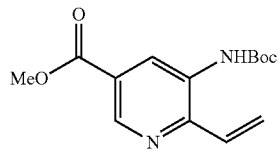

According to the process of Reference Example 20, the title compound was prepared from the compound of Reference Example 41-1.
LC-MS ([M+H]$^+$/Rt (min)): 279.5/0.885

Reference Example 41-3

Methyl 5-[(tert-butoxycarbonyl)amino]-6-formyl-nicotinate

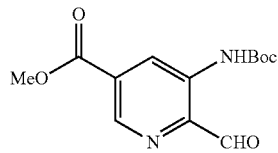

To a solution of the compound of Reference Example 41-2 (207 mg) in a mixture of acetone (8 mL)/water (4 mL) were added sodium periodate (659 mg) and osmium tetroxide (2.5 wt % in test-butanol, 0.71 mL), and the mixture was stirred at room temperature for 3 hours. To the reaction mixture were then added saturated aqueous sodium thiosulfate solution and water, and the mixture was extracted with ethyl acetate. The organic layer was washed with brine, dried over sodium sulfate, filtered, and then concentrated in vacuo. The residue was purified by silica gel column chromatography (hexane/ethyl acetate) to give the title compound (110 mg).
LC-MS ([M+H]$^+$/Rt (min)): 281.2/1.037

Reference Example 41-4

Methyl 5-[(tert-butoxycarbonyl)amino]-6-(hydroxymethyl)-nicotinate

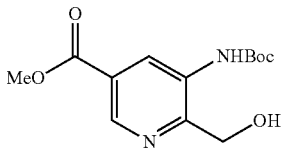 [SMILES: COC(=O)c1cnc(CO)c(NC(=O)OC(C)(C)C)c1]

To a solution of the compound of Reference Example 41-3 (110 mg) in methanol was added sodium borohydride (15 mg), and the mixture was stirred at room temperature for 1 hour. To the reaction mixture were then added saturated aqueous ammonium chloride solution and water, and the mixture was extracted with ethyl acetate. The organic layer was washed with brine, dried over sodium sulfate, filtered, and then concentrated in vacuo to give the title compound (111 mg).
LC-MS ([M+H]$^+$/Rt (min)): 282.8/0.761

Reference Example 41-5

2-Oxo-1,4-dihydro-2H-pyrido[3,2-d][1,3]oxazine-7-carboxylic acid

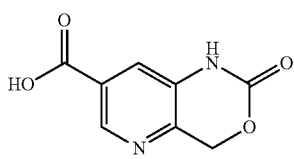 [SMILES: O=C1Nc2cc(C(=O)O)cnc2CO1]

To a solution of the compound of Reference Example 41-(111 mg) in THF (2 mL)/methanol (4 mL) was added 2 mol/L aqueous sodium hydroxide solution (0.39 mL), and the mixture was stirred at room temperature for 16 hours. To the reaction solution was added 2 mol/L hydrochloride (0.25 mL) to adjust pH to 7. The reaction mixture was concentrated in vacuo to give the title compound (76 mg).
LC-MS ([M+H]$^+$/Rt (min)): 195.1/0.325

Reference Example 41-6

2-Oxo-N-{1-[3-(trfluoromethyl)benzyl]-1H-imidazol-4-yl}-1,4-dihydro-2H-pyrido[3,2-d][1,3]oxazine-7-carboxamide

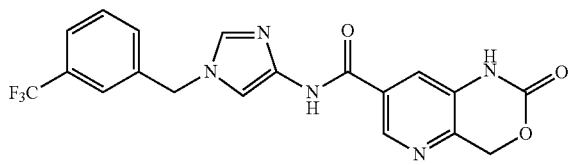 [SMILES: O=C1Nc2cc(C(=O)Nc3cn(Cc4cccc(C(F)(F)F)c4)cn3)cnc2CO1]

According to the process of Reference Example 7, the title compound was prepared from the compounds of Reference Examples 41-5 and 4.
LC-MS ([M+H]$^+$/Rt (min)): 418.2/0.711

Reference Example 42

2-Oxo-N-[1-(3,4,5-trifluorobenzylimidazol)-1H-4-yl]-1,4-dihydro-2H-pyrido[3,2-d][1,3]oxazine-7-carboxamide

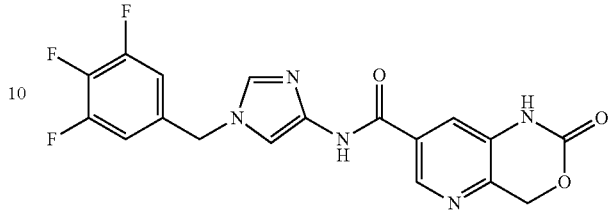

According to the process of Reference Example 7, the title compound was prepared from the compounds of Reference Examples 41-5 and 6.
LC-MS ([M+H]$^+$/Rt (min)): 404.2/0.670

Reference Example 43-1

Methyl 6-chloro-5-(dibromomethyl)-nicotinate

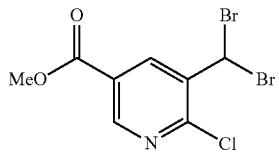 [SMILES: COC(=O)c1cnc(Cl)c(C(Br)Br)c1]

To a suspension of methyl 6-chloro-5-methyl-nicotinate (467 mg) in carbon tetrachloride (25 ml,) were added N-bromosuccinimide (1.34 g) and benzoyl peroxide (218 mg), and the mixture was stirred at 100° C. for 7.5 hours. The mixture was cooled to room temperature, and to the reaction mixture were added saturated aqueous sodium thiosulfate solution and water, and then the mixture was extracted with chloroform. The organic layer was washed with brine, dried over anhydrous sodium sulfate, filtered, and then concentrated in vacuo. The residue was purified by silica gel column chromatography (hexane/ethyl acetate) to give the title compound (833 mg).
LC-MS ([M+H]$^+$/Rt (min)): 341.9/1.011

Reference Example 43-2

Methyl 6-chloro-5-formyl-nicotinate

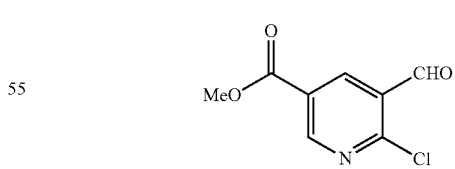

To a solution of the compound of Reference Example 43-1 (2.71 g) in acetonitrile (40 mL)/water (20 mL) was added silver nitrate (6.70 g), and the mixture was stirred at 100° C. for 3 hours. The insoluble product was removed by filtration, and the solvent was removed. To the residue was added saturated aqueous sodium hydrogen carbonate solution to adjust pH to 8, and the mixture was extracted with ethyl acetate. The organic layer was washed with brine,

Reference Example 43-3

Methyl 6-chloro-5-(difluoromethyl)-nicotinate

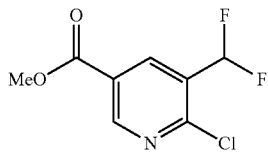 [SMILES: COC(=O)c1cnc(Cl)c(C(F)F)c1]

To a solution of the compound of Reference Example 432 (0.84 g) in dichloromethane (20 mL) was added DAST (1.11 mL) with ice-cooling, and the mixture was stirred with ice-cooling for 30 minutes. To the reaction mixture was added saturated aqueous sodium hydrogen carbonate solution to adjust pH to 8, and the mixture was extracted with chloroform.

The organic layer was washed with brine, dried over anhydrous sodium sulfate, filtered, and then concentrated in vacuo. The residue was purified by silica gel column chromatography (hexane/ethyl acetate) to give the title compound (0.45 g).

LC-MS ([M+H]$^+$/Rt (min)): 222.0/0.828

Reference Example 43-4

Methyl 5-(difluoromethyl)-6-(hydroxymethyl)-nicotinate

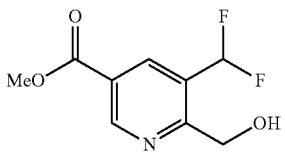 [SMILES: COC(=O)c1cnc(CO)c(C(F)F)c1]

According to the processes of Reference Examples 20, 41-3, and 41-4, the title compound was prepared from the compound of Reference Example 43-3.

LC-MS ([M+H]$^+$/Rt (min)): 218.1/0.564

Reference Example 44

Methyl 6-(hydroxymethyl)-5-(trifluoromethyl)-nicotinate

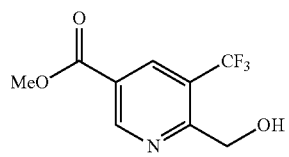 [SMILES: COC(=O)c1cnc(CO)c(C(F)(F)F)c1]

According to the processes of Reference Examples 20, 41-3, and 41-4, the title compound was prepared from methyl 6-chloro-5-(trifluoromethyl)-nicotinate.

LC-MS ([M+H]$^+$/Rt (min)): 236.1/0.649

Reference Example 45-1

Methyl 5-(2-tert-butoxy-2-oxoethoxy)-picolinate

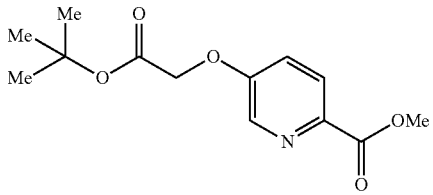 [SMILES: COC(=O)c1ccc(OCC(=O)OC(C)(C)C)cn1]

To a solution of methyl 5-hydroxy-picolinate (200 mg) in DMF (5 mL) were added potassium carbonate (361 mg) and test-butyl bromoacetate, and the mixture was stirred at 70° C. for 20 minutes. The mixture was cooled to room temperature, ant to the reaction mixture was added water, and then the mixture was extracted with ethyl acetate. The organic layer was washed with brine twice, dried over anhydrous sodium sulfate, filtered, and then concentrated in vacuo to give the title compound (320 mg).

LC-MS ([M+H]$^+$/Rt (min)): 268.2/0.777

Reference Example 45-2

{[6-(Methoxycarbonyl)pyridin-3-yl]oxy}acetic acid

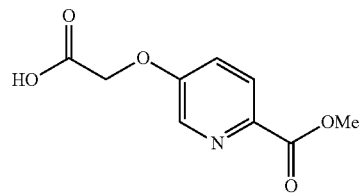 [SMILES: COC(=O)c1ccc(OCC(=O)O)cn1]

To a solution of the compound of Reference Example 45-1 (320 mg) in dichloromethane (4 mL) was added TFA (2 mL), and the mixture was stirred at room temperature for 2 hours. The solvent was removed to give the title compound (253 mg).

LC-MS ([M+H]$^+$/Rt (min)): 212.1/0.394

Reference Example 45-3

Methyl 5-(2-oxo-2-{[1-(3,4,5-trifluorobenzyl)-1H-imidazol-4-yl]amino}ethoxy)-picolinate

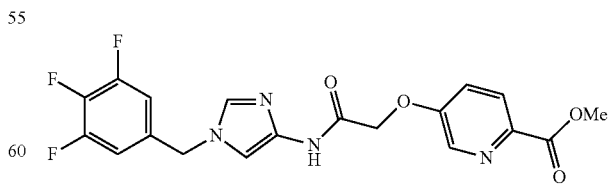

According to the process of Reference Example 7, the title compound was prepared from the compounds of Reference Example 45-2 and 6.

LC-MS ([M+H]$^+$/Rt (min)): 421.2/0.731

Reference Example 46-1

4-({[Tert-butyl(dimethyl)silyl]oxy}methyl)-5-methyl-1,3-thiazole-2-carboxylic acid

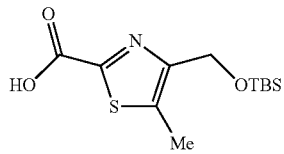 [SMILES: Cc1sc(C(=O)O)nc1CO[Si](C)(C)C(C)(C)C]

To a solution of (2-bromo-5-methyl-1,3-thiazol-4-yl)methanol (151 mg) in DMF (3 was added imidazole (59 mg) and TBSCl (131 mg), and the mixture was stirred at room temperature for 1 hour. To the reaction mixture were then added saturated aqueous ammonium chloride solution and water, and the mixture was extracted with ethyl acetate. The organic layer was washed with saturated aqueous ammonium chloride solution and brine, dried over anhydrous sodium sulfate, filtered, and then concentrated in vacuo. The residue was purified by silica gel column chromatography (hexane/ethyl acetate) to give 2-bromo-4-({[tert-butyl(dimethyl)silyl]oxy}methyl)-5-methyl-1,3-thiazole.

To a solution of the resulting 2-bromo-4-({[tert-butyl(dimethyl)silyl]oxy}methyl)-5-methyl-1,3-thiazole in THF (4 mL) was added n-butyllithium (0.91 mL) at −78° C., and the mixture was stirred at this to for 1 hour. An excess amount of powdered dry ice was then added thereto, and the mixture was stirred at this temperature for 45 minutes and then at room temperature for 40 minutes. To the reaction mixture was added saturated aqueous ammonium chloride solution, and then the mixture was extracted with ethyl acetate. The organic layer was washed with brine, dried over anhydrous sodium sulfate, filtered, and then concentrated in vacuo to give the title compound (127 mg).
LC-MS ([M+H]$^+$/Rt (min)): 288.1/1.058

Reference Exam 46-2

4-({[Tert-butyl(dimethyl)silyl]oxy}methyl)-5-methyl-N-[1-(3,4,5-trifluorobenzyl)-1H-imidazol-4-yl]-1,3-thiazole-2-carboxamide

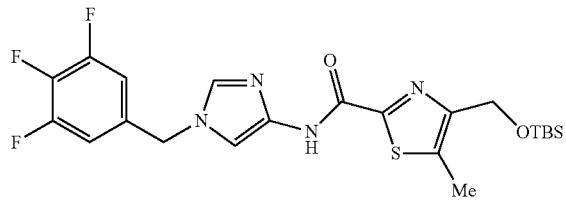 [SMILES: Cc1sc(C(=O)Nc2cn(Cc3cc(F)c(F)c(F)c3)cn2)nc1CO[Si](C)(C)C(C)(C)C]

According to the process of Reference Example 7, the title compound was prepared from the compounds of Reference Examples 46-1 and 6.
LC-MS ([M+H]$^+$/Rt (min)): 497.1/1.314

Reference Example 47

5-({[Tert-butyl(dimethyl)silyl]oxy}methyl)-4-methyl-N-[1-(3,4,5-trifluorobenzyl)-1H-imidazol-4-yl]-1,3-thiazole-2-carboxamide

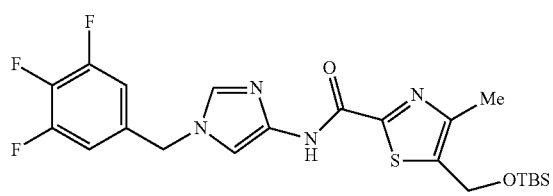 [SMILES: Cc1nc(C(=O)Nc2cn(Cc3cc(F)c(F)c(F)c3)cn2)sc1CO[Si](C)(C)C(C)(C)C]

According to the processes of Reference Examples 46-1 and 7, the title compound was prepared from the corresponding starting compound.
LC-MS ([M+H]$^+$/Rt (min)): 497.1/1.333

Reference Example 48

6-Formyl-N-{1-[3-(trifluoromethyl)benzyl]-1H-imidazol-4-yl}nicotinamide

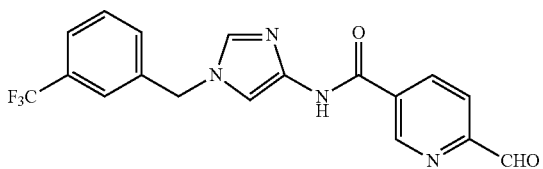 [SMILES: O=Cc1ccc(C(=O)Nc2cn(Cc3cccc(C(F)(F)F)c3)cn2)cn1]

To a suspension of the compound of Example 12 (200 mg) in dichloromethane (10 mL) was added manganese dioxide (2 g), and the mixture was stirred at room temperature for 19 hours. The reaction mixture was filtered through Celite®, and the filter cake was washed with ethyl acetate and methanol. The filtrate was concentrated in vacuo, and the residue was purified by silica gel column chromatography (chloroform/methanol) to give the title compound (55 mg).
LC-MS ([M+H]$^+$/Rt (min)): 375.2/0.793

Reference Example 49-1

Methyl 1-(3,4,5-trifluorobenzyl-1H-imidazole-4-carboxylate

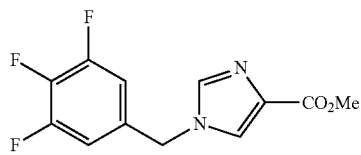 [SMILES: COC(=O)c1cn(Cc2cc(F)c(F)c(F)c2)cn1]

To a solution of methyl 1H-imidazole-4-carboxylate (14.0 g) in acetonitrile (200 mL) were added potassium carbonate (19.9 g) and potassium iodide (0.092 g), and 3,4,5-trifluorobenzyl bromide (14.6 mL) was added dropwise thereto at room temperature, and then the mixture was stirred at 70° C. for 6 hours. The mixture was cooled to room temperature, and to the reaction mixture was added water, and then the mixture was extracted with ethyl acetate. The organic layer was dried over anhydrous magnesium sulfate, filtered, and then concentrated in vacuo. The resulting crude product was washed with hexane/ethyl acetate (1/2, 60 mL) to give the title compound (14.0 g).
LC-MS ([M+H]$^+$/Rt (min)): 271.4/0.725

Reference Example 49-2

1-(3,4,5-Trifluorobenzyl)-1H-imidazole-4-carboxylic acid

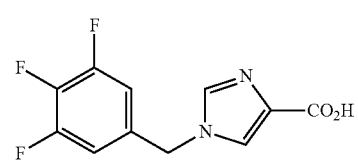

To a solution of the compound of Reference Example 49-1 (4.75 g) in methanol/THF (50 mL/50 mL) was added 2 mol/L aqueous sodium hydroxide solution (13.2 mL), and the mixture was stirred at 50° C. for 5 hours. The reaction mixture was concentrated in vacuo, and the residue was dissolved in water, and then aqueous hydrochloric acid solution was added thereto to adjust pH to 5. The resulting precipitate was collected on a filter, washed with water and hexane, and then dried at 50° C. in vacuo to give the title compound (4.52 g).

LC-MS ([M+H]$^+$/Rt (min)): 257.1/0.513

Reference Example 50

6-({[Tert-butyl(dimethyl)silyl]oxy}methyl)pyridine-3-amine

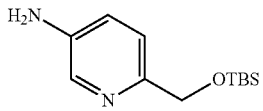

To a solution of (5-aminopyridin-2-yl)methanol (135 mg) in THF (15 ml) were added triethylamine (0.30 mL) and TBSCl (328 mg), and the mixture was stirred at room temperature for 6 hours. The solvent was removed in vacuo, and the resulting residue was purified by silica gel column chromatography (chloroform/methanol) to give the title compound (99 mg).
LC-MS ([M+H]$^+$/Rt (min)): 239.2/0.726

Reference Example 51

2-({[Tert-butyl(dimethyl)silyl]oxy}methyl)quinoline-6-amine

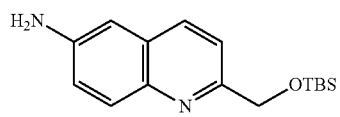 [SMILES: CC(C)(C)[Si](C)(C)OCc1ccc2cc(N)ccc2n1]

According to the process of Reference Example 50, the title compound was prepared from (6-aminoquinolin-2-yl)methanol.
LC-MS ([M+H]$^+$/Rt (min)): 289.9/0.836

Reference Examples 52-53

According to the process of Reference Example 7, the compounds of Reference Examples 52-53 were prepared from the compound of Reference Example 49 and each corresponding starting compound.

| Reference Examples | chemical structural formula | LC-MS: [M + H]$^+$/Rt (min) |
|---|---|---|
| 52 | ![structure] | 527.3/1.289 |
| 53 | ![structure] | 411.2/0.915 |

Reference Example 54

Methyl 6-(3-hydroxyprop-1-en-2-yl)nicotinate

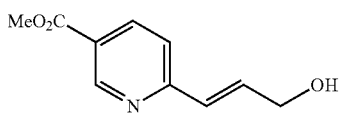 [SMILES: COC(=O)c1ccc(/C=C/CO)nc1]

To a solution of methyl 6-methylnicotinate (420 mg) in water (2 mL) were added triethylamine (0.065 mL) and paraformaldehyde (42 mg), and the mixture was stirred under microwave irradiation at 150° C. for 3 hours. To the reaction mixture was added water, and the mixture was extracted with ethyl acetate. The organic layer was washed with brine, dried over magnesium sulfate, filtered, and then concentrated in vacuo. The residue was purified by silica gel column chromatography (hexane/ethyl acetate) to give the title compound (24 mg).
LC-MS ([M+H]$^+$/Rt (min)): 194.1/0.532
$^1$H-NMR (400 MHz, CDCl$_3$): δ9.15-9.13 (1H, m), 8.29 (1H, dd, J=8.4, 2.0 Hz), 7.70 (1H, d, J=8.4 Hz), 5.94 (1H, s), 5.65 (1H, s), 4.61 (2H, s), 3.97 (3H, s).

Reference Example 55

Methyl 6-[(1E)-3-hydroxyprop-1-en-1-yl]nicotinate

To a solution of (2E)-3-[5-(methoxycarbonyl)pyridin-2-yl]prop-2-enoic acid (50 mg) in DME (1 mL) were added N-methylmorpholine (0.056 mL) and isobutyl chloroformate (0.035 mL), and the mixture was stirred at 0° C. for 1 hour. The precipitate was removed by filtration, and the filtrate was concentrated to give a crude product of mixed anhydxate.

To a suspension of sodium bocohydride (23.3 mg) in THF/water (2 mL/0.5 mL) was added a solution of the resulting mixed anhydrate in THF at 0° C. The reaction solution was stirred at room temperature for 3 hours. To the reaction mixture was added saturated aqueous sodium hydrogen carbonate solution, and the mixture was extracted with ethyl acetate. The organic layer was washed with brine, dried over magnesium sulfate, filtered, and then concentrated in vacuo. The residue was purified by silica gel column chromatography (chloroform/methanol) to give the title compound (19 mg).
LC-MS ([M+H]$^+$/Rt (min)): 194.3/0.741

Reference Example 56-1

Methyl 6-(oxiran-2-yl)-nicotinate

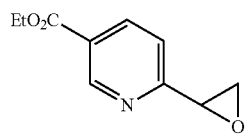 [SMILES: CCOC(=O)c1ccc(C2CO2)nc1]

To a solution of ethyl 6-ethenyl-nicotinate (210 mg) in tert-butylalcohol/water (6 mL/3 mL) was added NBS (232 mg), and the mixture was stirred at 40° C. for 2 hours. The reaction was quenched with aqueous sodium hydroxide solution in an ice bath, and the reaction solution was neutralized with hydrochloric acid, and then the mixture was extracted with ethyl acetate. The organic layer was washed with brine, dried over magnesium sulfate, filtered, and then concentrated in vacuo.

The residue was dissolved in THF (10 mL), and sodium hydride (78 mg) was added thereto in an ice bath, and the mixture was stirred at room temperature for 1 hour. To the reaction mixture was added brine, and the mixture was extracted with ethyl acetate. The organic layer was washed with brine, dried over magnesium sulfate, filtered, and then concentrated in vacuo. The residue was purified by silica gel column chromatography (hexane/ethyl acetate) to give the title compound (125.3 mg).
LC-MS ([M+H]$^+$/Rt (min)): 194.1/0.654

Reference Example 56-2

Ethyl 6-(2-hydroxyethyl)-nicotinate

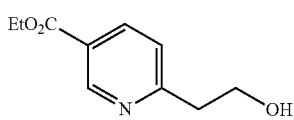 [SMILES: CCOC(=O)c1ccc(CCO)nc1]

To a solution of the compound of Reference Example 56-1 (125 mg) in ethanol (10 mL) were added 5% palladium/carbon (138 mg) and ammonium formate (204 mg), and the mixture was stirred at 50° C. for 3 hours. The palladium was filtered through Celite®, and the filtrate was concentrated in vacuo. The residue was purified by silica gel column chromatography (ethyl acetate/hexane) to give the title compound (87.3 mg).
LC-MS ([M+H]$^+$/Rt (min)): 196.1/0.467
$^1$H-NMR (400 MHz, CDCl$_3$): δ9.12 (1H, d, J=2.4 Hz), 8.23 (1H, dd, J=8.0, 2.4 Hz), 7.26 (1H, d, J=8.0 Hz), 4.41 (2H, q, J=7.6 Hz), 4.06-4.03 (2H, m), 3.11-3.07 (2H, m), 1.41 (3H, t, J=7.6 Hz).

Reference Example 57

Methyl 5-(hydroymethyl)pyrazine-2-carboxylate

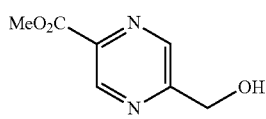

According to the processes of Reference Examples 20, 41-3, and 41-4, the title compound was prepared from methyl 5-chloropyrazine-2-carboxylate.
LC-MS ([M+H]$^+$/Rt (min)): 169.0/0.334

Reference Example 58

6-({Methyl[(2-nitrophenyl)sulfonyl]amino}methyl)-N-{1-[3-(trifluoromethyl)benzyl]-1H-imidazol-4-yl}nicotinamide

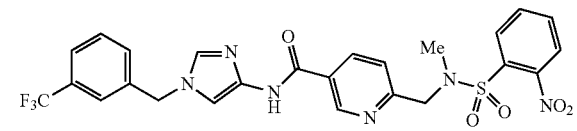 [SMILES: CN(Cc1ccc(C(=O)Nc2cn(Cc3cccc(C(F)(F)F)c3)cn2)cn1)S(=O)(=O)c1ccccc1[N+](=O)[O-]]

To a solution of the compound of Example 12 (101 mg) in chloroform (4 mL) were added N-methyl-2-nitrobenzenesulfonamide (79 mg), diethyl azodicarboxylate (2.2 mol/L toluene solution, 159 μL), and triphenylphosphine (92 mg), and the mixture was stirred at room temperature for 20 hours. N-methyl-2-nitrobenzenesulfonamide (80 mg), diethyl azodicarboxylate (2.2 mol/L toluene solution, 159 μL), and triphenylphosphine (93 mg) were additionally added thereto, and the mixture was stirred at 60° C. for 6 hours. N-methyl-2-nitrobenzenesulfonamide (157 mg), diethyl azodicarboxylate (2.2 mol/L toluene solution, 318 μL), and triphenylphosphine (194 mg) were additionally added thereto, and the mixture was stirred at 60° C. for 2 hours. The reaction solution was concentrated in vacuo, and the residue was purified by silica gel chromatography (hexane/ethyl acetate) to give the title compound (174 mg).
LC-MS ([M+H]$^+$/Rt (min)): 575.3/0.944

Reference Example 59-1

Methyl 5-ethenyl-6-hydroxy-nicotinate

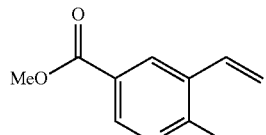

According to the process of Reference Example 20, the title compound was prepared from methyl 5-bromo-6-hydroxynicotinate.
LC-MS ([M+H]$^+$/Rt (min)): 180.0/0.541

Reference Example 59-2

Methyl 6-chloro-5-ethenyl-nicotinate

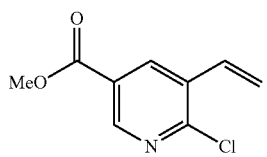

To a suspension of the compound of Reference Example 59-1 (1.37 g) in phosphorous oxychloride (14.3 mL) was stirred at 90° C. for 1 hour. The reaction mixture was cooled to room temperature and concentrated in vacuo. The residue was diluted with ethyl acetate, neutralized with saturated aqueous sodium hydrogen carbonate solution, and then extracted with ethyl acetate. The organic layer was washed with brine, dried over sodium sulfate, filtered, and then concentrated in vacuo to give the title compound (1.45 g).
LC-MS ([M+H]$^+$/Rt (min)): 198.0/0.870

Reference Example 59-3

Methyl 6-chloro-5-formyl-nicotinate

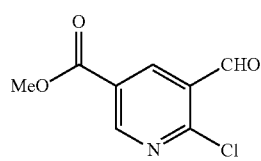 [SMILES: COC(=O)c1cnc(Cl)c(C=O)c1]

According to the process of Reference Example 41-3, the title compound was prepared from the compound of Reference Example 59-2.
LC-MS ([M+H]$^+$/Rt (min)): 200.0/0.671

Reference Example 60-1

Isopropyl 5-bromo-6-chloro-nicotinate

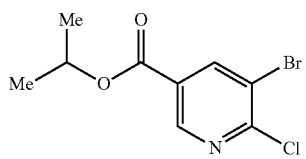 [SMILES: CC(C)OC(=O)c1cnc(Cl)c(Br)c1]

A suspension of 5-promo-6-hydroxy-nicotinic acid (10 g) in thionyl chloride (17 mL)/DMF (0.36 mL) was stirred at 80° C. for 2 hours. The reaction mixture was cooled to room temperature and concentrated in vacuo. To the residue was then added 2-propanol (25 mL), and the mixture was stirred at 100° C. for 40 minutes. The reaction mixture was cooled to room temperature and concentrated in vacuo. To the residue were then added saturated aqueous sodium carbonate solution and water, and the mixture was extracted with ethyl acetate. The organic layer was washed with brine, dried over sodium sulfate, filtered, and then concentrated in vacuo to give the title compound (12.4 g).
LC-MS ([M+H]$^+$/Rt (min)): 278.0/1.102

Reference Example 60-2

Isopropyl 6-chloro-5-formyl-nicotinate

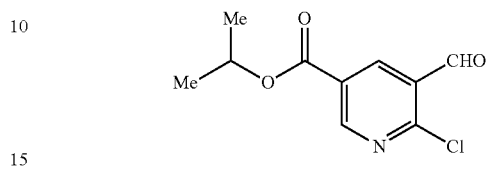

To a solution of the compound of Reference Example 60-1 (2.0 g) in THF (30 mL) was cooled to −20° C., and isopropylmagnesium chloride lithium chloride complex (1.3 mol/L in THF, 7.2 ml) was added thereto, and then the reaction mixture was stirred at −20° C. for 35 minutes. Isopropylmagnesium chloride lithium chloride complex (1.3 mol/L in THF, 0.55 mL) was added thereto, and the mixture was additionally stirred at −20° C. for 25 minutes. DMF (1.11 mL) was added thereto, and the reaction mixture was stirred at room temperature for 1 hour 10 minutes. Saturated aqueous ammonium chloride solution and water were added thereto, and the mixture was extracted with ethyl acetate. The organic layer was washed with brine, dried over sodium sulfate, filtered, and then concentrated in vacuo to give the title compound (1.64 g).
LC-MS ([M+H]$^+$/Rt (min)): 228.1/0.897

Reference Example 60-3

Isopropyl 6-chloro-5-(difluoromethyl)-nicotinate

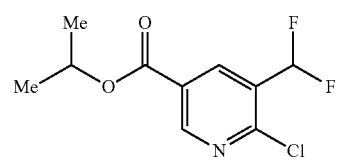 [SMILES: CC(C)OC(=O)c1cnc(Cl)c(C(F)F)c1]

According to the process of Reference Example 43-3, the title compound was prepared from the compound of Reference Example 60-2.
LC-MS ([M+H]$^+$/Rt (min)): 250.1/1.014

Reference Example 60-4

Isopropyl 6-bromo-5-(difluoromethyl)-nicotinate

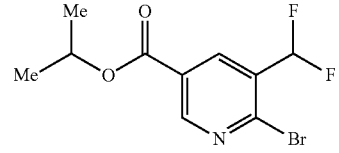

To a solution of the compound of Reference Example 60-3 (500 mg) in acetonitrile (10 mL) was added bromotrimethylsilane (0.52 mL), and the mixture was stirred at 100° C. for 4 hours. The reaction mixture was cooled to room temperature, and then concentrated in vacuo. The residue was purified by silica gel column chromatography (hexane/ethyl acetate) to give the titie compound (585 mg).
LC-MS ([M+H]$^+$/Rt (min)): 294.0/1.035

Reference Example 60-5

Isopropyl 5-(difluoromethyl)-6-{[(4-methoxybenzyl)oxy]methyl}-nicotinate

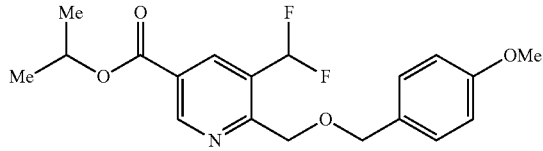 [SMILES: COc1ccc(COCc2ncc(C(=O)OC(C)C)cc2C(F)F)cc1]

To a solution of the compound of Reference Example 60-4 (100 mg) in 1,4-dioxane (3 mL) /water (0.3 mL) were added [1,1'-bis(diphenylphosphino)ferrocene]palladium (II) dichloride dichloromethane adduct (28 mg), potassium (4-methoxy)benzyloxymethyltrifluoroborate (114 mg), and cesium carbonate (222 mg), and then the mixture was stirred at 120° C. for 9.5 hours, The reaction mixture was cooled to room temperature and concentrated in vacuo. The residue was purified by silica gel column chromatography (hexane/ethyl acetate) to give the title compound (70 mg).
LC-MS ([M+H]$^+$/Rt (min)): 366.5/1.129
$^1$H-NMR (400 MHz, CDCl$_3$): δ9.20 (1H, s), 8.54 (1H, s), 7.27 (2H, d, J=8.7 Hz), 7.16 (1H, t, J=54.8 Hz), 6.89 (2H, d, J=8.7 Hz), 5.30 (1H, sep, J=5.9 Hz), 4.83 (2H, s), 4.52 (2H, s), 3.81 (3H, s), 1.40 (6H, d, J=5.9 Hz).

Reference Example 60-6

Isopropyl 5-(difluoromethyl)-6-(hydroxymethyl)-nicotinate

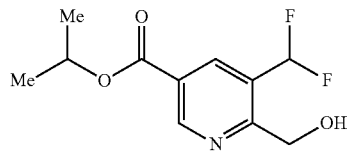

To a solution of the compound of Reference Example 60-5 (44 mg) in dichloromethane (1.5 mL) was added TFA (1.5 mL), and the mixture was stirred at room temperature for 17 hours. The reaction mixture was concentrated in vacuo, and the residue was neutralized with saturated aqueous sodium hydrogen carbonate solution, and then extracted with ethyl acetate. The organic layer was washed with brine, dried over sodjum sulfate, filtered, and then concentrated in vacuo.
The residue was purified by silica gel column. chromatography (hexane/ethyl acetate) to give the title compound (16 mg).
LC-MS ([M+H]$^+$/Rt (min)): 246.1/0.756

Reference Example 61

Tert-butyl 5-boom-6-chloro-nicotinate

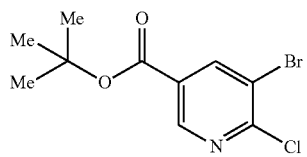 [SMILES: CC(C)(C)OC(=O)c1cnc(Cl)c(Br)c1]

A suspension of 5-bromo-6-hydroxy-nicotinic acid (10 g) in thionyl chloride (17 mL)/DMF (0.36 mL) was stirred at 80° C. for 2 hours. The reaction mixture was cooled to room temperature and concentrated in vacuo. To the residue were added. toluene (50 mL), N,N-diisopropylethylamine (16 mL), and tert-butanol (22 mL), and then the mixture was stirred at room temperature for 3 hours and then at 80° C. for 1 hour. DMAP (0.28 g) was added thereto, and the mixture was additionally stirred at 80° C. for 2 hours. The reaction mixture was cooled to room temperature, and saturated aqueous sodium carbonate solution and water were added thereto, and then the mixture was extracted with ethyl acetate. The organic layer was washed with saturated aqueous sodium carbonate solution, saturated aqueous potassium hydrogen sulfate solution, saturated aqueous sodium hydrogen carbonate solution, and then brine, dried over sodium sulfate, filtered, and then concentrated in vacuo. The residue was purified by silica gel column chromatography (hexane/ethyl acetate) to give the title compound (5.85 g)
LC-MS ([M+H]$^+$/Rt (min)): 292.0/1.188

Reference Example 62

Isopropyl 5-(difluoromethyl)-6-iodo-nicotinate

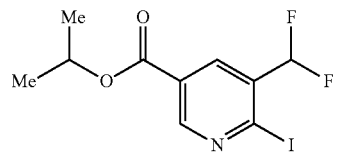 [SMILES: CC(C)OC(=O)c1cnc(I)c(C(F)F)c1]

According to the process of Reference Example 60-4, the title compound was prepared from the compound of Reference Example 60-3 and iodotrimethylsilane.
LC-MS ([M+H]$^+$/Rt (min)): 342.0/1.054

Reference Example 63

Methyl 5-(difluoromethyl)-6-iodo-nicotinate

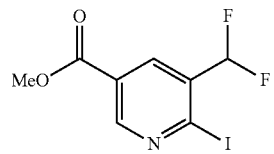 [SMILES: COC(=O)c1cnc(I)c(C(F)F)c1]

According to the process of Reference Example 60-4, the title compound was prepared from the compound of Reference Example 43-3 and iodotrimethylsilane.
LC-MS ([M+H]$^+$/Rt (min)): 314.0/0.875

Reference Example 64-1

4-Nitro-1-{[2-(trimethylsilyl)ethoxy]methyl}-1H-imidazole

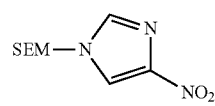

A suspension of sodium hydride (3.04 g) in DMF (15 mL) was cooled with an ice, and a solution of 4-nitroimidazole (5.66 g) in DMF (40 mL) was added thereto, and then the mixture was stirred with ice-cooling for 45 minutes. 2-(Trimethylsiiyi)ethoxymethyl chloride (9.65 mL) was added thereto, and the mixture was stirred at room temperature for 2 hours. Methanol, an ice, and brine were added thereto, and the mixture was extracted with hexane/ethyl acetate (1/1). The organic layer was dried over sodium sulfate, filtered, and then concentrated in vacuo. The residue was purified by silica gel column chromatography (hexane/ethyl acetate) to give the title compound (8.62 g).
LC-MS ([M+H]$^+$/Rt (min)): 244.1/0.927

Reference Example 64-2

1-{[2-(Trimethylsilyl)ethoxy]methyl}-1H-imidazole-4-amine

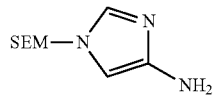 [SMILES: C[Si](C)(C)CCOCn1cnc(N)c1]

A suspension of the compound of Reference Example 64-1 (7.84 g) and rhodium/carbon (3.92 g) in ethyl acetate (200 mL) was stirred under hydrogen atmosphere at room temperature for 10 hours. The reaction mixture was filtered through Celite®, and to the filtrate was added hydrogen chloride (4 mol/L in 1,4-dioxane, 8 mL), and then the mixture was concentrated in vacuo to give the title compound (6.22 g).
LC-MS ([M+H]$^+$/Rt (min)): 214.2/0.665

Reference Example 64-3

5-(Difluoromethyl)-6-{[(4-methoxybenzyl)oxy]methyl}-N-(1-{[2-(trimethylsilyl)ethoxy]methyl}-1H-imidazol-4-yl)nicotinamide

According to the process of Example 49, the title compound was prepared from the compounds of Reference Examples 64-2 and 60-5.
LC-MS ([M+H]$^+$/Rt (min)): 519.4/1.105

Reference Example 64-4

5-(Difluoromethyl)-6-(hydroxymethyl)-N-(1H-imidazol-4-yl)nicotinamide

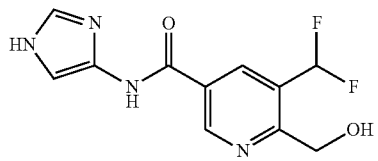 [SMILES: O=C(Nc1c[nH]cn1)c1cnc(CO)c(C(F)F)c1]

According to the process of Example 50, the title compound was prepared from the compound of Reference Example 64-3.
LC-MS ([M+H]$^+$/Rt (min)): 269.1/0.322

Reference Example 65-1

N-{1-[3-(Trifluoromethyl)benzyl]-1H-imidazol-4-yl}prop-2-enamide

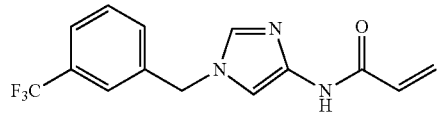 [SMILES: C=CC(=O)Nc1cn(Cc2cccc(C(F)(F)F)c2)cn1]

To a solution of the compound of Reference Example 4 (1 g) and DIEA (1.4 mL) in THF (25 mL) was added acryloyl chloride (0.32 mL) slowly. The reaction mixture was stirred at room temperature for 1.5 hours, and water was added thereto, and then the mixture was extracted with chloroform. The organic layer was washed with brine, dried over anhydrous sodium sulfate, filtered, and then concentrated in vacuo. The resulting residue was purified by silica gel column chromatography (chloroform/methanol) to give the title compound (0.13 g).
LC-MS ([M+H]$^+$/Rt (min)): 296.2/0.718
$^1$H-NMR (400 MHz, DMSO-d$_6$): δ10.56 (1H, s), 7.69-7.66 (3H, m), 7.62-7.57 (2H, m), 7.33 (1H, s), 6.44 (1H, dd, J=17.1, 10.4 Hz), 6.15 (1H, dd, J=17.1, 2.4 Hz), 5.63 (1H, dd, J=10.4, 2.4 Hz), 5.27 (2H, s).

Reference Example 65-2

Methyl 5-[(1E)-3-oxo-3-({1-[3-(trifluoromethyl)benzyl]-1H-imidazol-4-yl}amino)prop-1-en-1-yl]picolinate

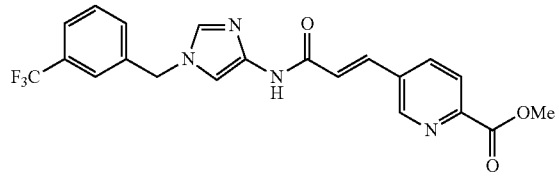 [SMILES: COC(=O)c1ccc(/C=C/C(=O)Nc2cn(Cc3cccc(C(F)(F)F)c3)cn2)cn1]

To a solution of the compound of Reference Example 65-1 (60 mg) in DMF (2 mL) were added methyl 5-bromopicolinate (53 mg), dichlorobis(tri-O-tolylphosphine)palladium (II) (16 mg), and triethylamine (0.042 mL), and the mixture was stirred at 90° C. for 3.5 hours and then at 130° C. for 2 hours. The mixture was cooled to room temperature, and water and a small amount of methanol were added thereto, and then the mixture was extracted with ethyl acetate. The organic layer was washed with brine, dried over anhydrous sodium sulfate, filtered, and then concentrated in vacuo. The resulting residue was purified by amino silica gel column chromatography (ethyl acetate/methanol) to give the title compound (42 mg).
LC-MS ([M+H]$^+$/Rt (min)): 431.2/0.790
$^1$H-NMR (400 MHz, DMSO-d$_6$): δ10.73 (1H, s), 8.87 (1H, s), 8.14-8.08 (2H, m), 7.71-7.56 (6H, m), 7.41 (1H, s), 7.07 (1H, d, J=15.8 Hz), 5.29 (2H, s), 3.88 (3H, s).

Reference Example 66

Ethyl (2E)-3-[6-(hydroxymethyl)pyridin-3-yl]prop-2-enoate

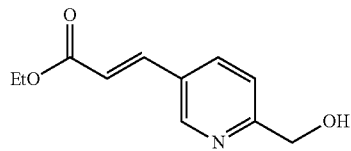 [SMILES: CCOC(=O)/C=C/c1ccc(CO)nc1]

To a solution of 2-ethoxycarbonyl vinylboronic acid pinacol ester (361 mg) in 1,4-dioxane (15 mL)/water (1.5 mL) were added 5-bromo-2-hydroxymethylpyridine (300 mg), bis(tri-t-butylphosphine)palladium (0) (122 mg), and potassium carbonate (662 mg), and the mixture was stirred under microwave irradiation at 130° C. for 1.5 hours. The reaction mixture was cooled to room temperature, and water was added thereto, and then the mixture was extracted with ethyl acetate. The organic layer was washed with brine, dried over anhydrous sodium sulfate, filtered, and then concentrated in vacuo. The resulting residue was purified by silica gel column chromatography (hexane/ethyl acetate) to give the title compound (204 mg).
LC-MS ([M+H]$^+$/Rt (min)): 208.1/0.476

Reference Example 67

Ethyl (2E)-3-[5-chloro-6-(hydroxymethyl)pyridin-3-yl]prop-2-enoate

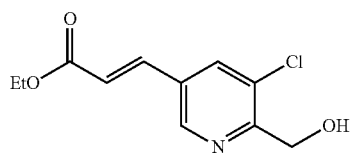 [SMILES: CCOC(=O)/C=C/c1cnc(CO)c(Cl)c1]

According to the process of Reference Example 66, the title compound was prepared from the corresponding starting compound.
LC-MS ([M+H]$^+$/Rt (min)): 242.1/0.719

Reference Example 68-1

6-Chloro-N-[1-(3,4,5-trifluorobenzyl)-1H-imidazol-4-yl]pyridazine-3-carboxamide

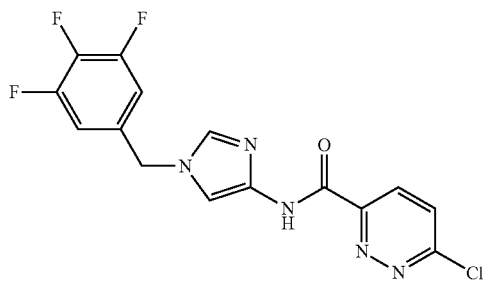 [SMILES: O=C(Nc1cn(Cc2cc(F)c(F)c(F)c2)cn1)c1ccc(Cl)nn1]

According to the process of Reference Example 7, the title compound was prepared from the compound of Reference Example 6 and the commercially available starting compound.
LC-MS ([M+H]$^+$/Rt (min)): 368.2/0.820

Reference Example 68-2

6-Ethenyl-N-[1-(3,4,5-trifluorobenzyl)-1H-imidazol-4-yl]pyridazine-3-carboxamide

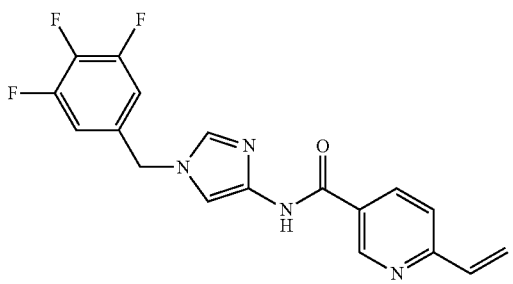 [SMILES: C=Cc1ccc(C(=O)Nc2cn(Cc3cc(F)c(F)c(F)c3)cn2)cn1]

According to the process of Reference Example 20, the title compound was prepared from the compound of Reference Example 68-1.
LC-MS ([M+H]$^+$/Rt (min)): 360.2/0.809

Example 1

5-(Hydroxymethyl)-N-{1-[3-(trifluoromethyl)benzyl]-1H-imidazol-4-yl}picolinamide

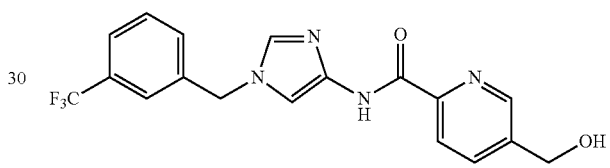

To a solution of Reference Example 7 (100 mg) in THF (2 mL)/methanol (1 mL) was added lithium borohydride (3 mol/L in THF, 0.08 mL), and the mixture was stirred at room temperature for 3 hours. To the reaction mixture were added saturated aqueous ammonium chloride solution and water, and the mixture was extracted with ethyl acetate. The organic layer was washed with brine, dried over anhydrous sodium sulfate, filtered, and then concentrated in vacuo. To the resulting solid were added ethyl acetate (2 mL) and hexane (2 mL), and the mixture was placed in an ultrasound bath, ant then the resulting solid was collected on a filter, washed with hexane/ethyl acetate (1/1, 1 mL×2), and dried at 40° C. in vacuo to give the title compound (70 mg).
LC-MS ([M+H]$^+$/Rt (min)): 377.2/0733

Examples 2-3

According to the process of Example 1, the compounds of Examples 2-3 were prepared from the corresponding compound of each Reference Example.

| Examples | chemical structural formula | LC-MS: [M + H]$^+$/Rt (min) |
|---|---|---|
| 2 |  | 393.2/0.594 |

| Examples | chemical structural formula | LC-MS: [M + H]+/Rt (min) |
|---|---|---|
| 3 | 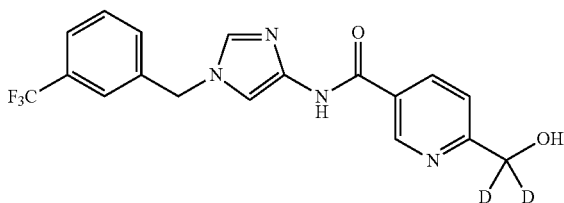 [SMILES: [2H]C([2H])(O)c1ccc(C(=O)Nc2cn(Cc3cccc(C(F)(F)F)c3)cn2)cn1] | 369.1/0.732 |

Example 4

6-[Hydroxy($^2$H$_2$)methyl]-N-{1-[3-(trifluoromethyl)benzyl]-1H-imidazol-4-yl}nicotinamide

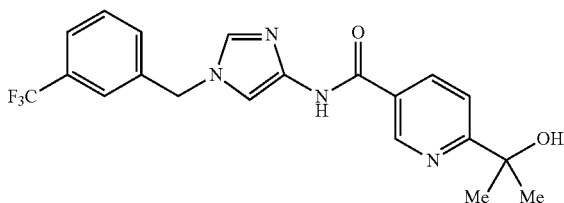 [SMILES: CC(C)(O)c1ccc(C(=O)Nc2cn(Cc3cccc(C(F)(F)F)c3)cn2)cn1]

To a suspension of lithium aluminum deuteride (21 mg) in THF (3 mL) was added the compound of Reference Example 8 (100 mg) with ice-cooling, and the mixture was stirred at this temperature for 30 minutes ant then at room temperature for 2 hours. Lithium aluminum deuteride (11 mg) was added thereto, and the mixture was additionally stirred at room temperature for 1 hour. Water (0.040 mL), 10% aqueous sodium hydroxide solution (0.060 mL), and then water (0.12 mL) were added thereto, and the mixture was stirred at room temperature for 20 minutes. The insoluble product was removed by filtration, and the residue was washed with water, ethyl acetate/methanol (1/1), ethyl acetate, and then methanol. The filtrate was concentrated in vacuo, and to the residue were added methanol and water, and then the mixture was placed in an ultrasound bath. The resulting precipitate was collected on a filter, washed with water, and then dried at 50° C. in vacuo to give the title compound (53 mg).
LC-MS ([M+H]+/Rt (min)): 379.2/0.673
$^1$H-NMR (400 MHz, DMSO-d$_6$): δ11.00 (1H, s), 9.01 (1H, d, J=1.8 Hz), 8.30 (1H, d, J=8.2, 1.8 Hz), 7.73-7.68 (3H, m), 7.64-7.61 (2H, m), 7.54 (1H, d, J=8.2 Hz), 7.47 (1H, d, J=1.2 Hz), 5.48 (1H, s), 5.31 (2H, s).

Example 5

6-(2-Hydroxypropan-2-yl)-N-{1-[3-(trifluoromethyl)benzyl]-1H-imidazol-4-yl}nicotinamide To a solution of the compound of Reference Example 8 (70 mg) in THF (5 mL) was added methylmagnesium bromide (0.97 mol/L in THF, 0.89 mL), and the mixture was stirred at room temperature for 20 hours. Methylmagnesium bromide (0.97 mol/L in THF, 0.45 mL) was added thereto, and the mixture was additionally stirred for 5.5 hours. To the reaction mixture were added saturated aqueous ammonium chloride solution and water, and the mixture was extracted with ethyl acetate. The organic layer was washed with brine, dried over anhydrous sodium sulfate, filtered, and then concentrated in vacuo. The residue was purified by silica gel column chromatography (chloroform/methanol) to give the title compound (10 mg).
LC-MS ([M+H]+/Rt (min)): 405.2/0.742
$^1$H-NMR (400 MHz, DMSO-d$_6$): δ10.97 (1H, s), 8.99 (1H, s), 8.27 (1H, d, J=8.2 Hz), 7.77-7.61 (6H, m), 7.47 (1H, s), 5.31-5.30 (3H, m), 1.44 (6H, s).

Example 6

6-(1-Hydroxyethyl)-N-{1-[3-(trfluoromethyl)benzyl]-1H-imidazol-4-yl}nicotinamide

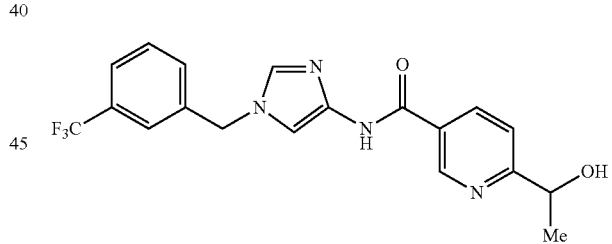

According to the process of Example 5, the title compound was prepared from the compound of Reference Example 48.
LC-MS ([M+H]+/Rt (min)): 391.2/0.717
$^1$H-NMR (400 MHz, DMSO-d$_6$): δ10.98 (1H, s), 9.00 (1H, d, J=1.8 Hz), 8.29 (1H, dd, J=8.3, 1.8 Hz), 7.73-7.72 (2H, m), 7.70-7.68 (1H, m), 7.64-7.61 (2H, m), 7.57 (1H, d, J=8.3 Hz), 7.47 (1H, d, J=1.2 Hz), 5.46 (1H, d, J=4.9 Hz), 5.30 (2H, s), 4.75 (1H, qd, J=6.7, 4.9 Hz), 1.36 (1H, d, J=6.7 Hz).

Examples 7-9

According to the process of Reference Example 7, the compounds of Examples 7-9 were prepared from the corresponding compounds of each Reference Example.

| Examples | chemical structural formula | LC-MS: [M + H]⁺/Rt (min) |
|---|---|---|
| 7 | F₃C-benzyl-imidazole-NH-C(O)-thiazole-CH₂OH | 383.2/0.729 |
| 8 | 3,4,5-trifluorobenzyl-imidazole-NH-C(O)-thiazole-CH₂OH | 369.1/0.690 |
| 9 | F₃C-benzyl-imidazole-NH-C(O)-pyridine-CH₂OMe | 391.2/0.773 |

Example 10

6-(Hydroxymethyl)-N-[1-(3,4,5-trifluorobenzyl)-1H-imidazol-4-yl]nicotinamide

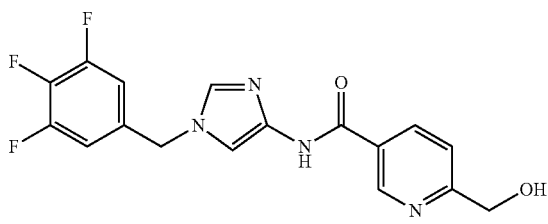 [SMILES: O=C(Nc1cn(Cc2cc(F)c(F)c(F)c2)cn1)c1ccc(CO)nc1]

To a solution of methyl 6-(hydroxymethyl)-nicotinate (0.924 g) in THF (22 mL) was added 5 mol/L aqueous potassium hydroxide solution (2.2 mL). The mixture was stirred at room temperature overnight, concentrated in vacuo to remove the solvent, and then dried in vacuo. To a solution of the resulting solid in DMF (25 mL) were added the compound of Reference Example 6 (1.61 g), HATU (2.52 g), and diisopropylethylamine (2.38 mL), and the mixture was stArred at room temperature for 1 hour. To the reaction mixture were then added saturated aqueous sodium hydrogen carbonate solution and water, and the resulting precipitate was collected on a filter. The resulting filter cake was washed with water/acetonitrile and then ethyl acetate, and dried in vacuo to give the title compoud (1.375 g).

LC-MS ([M+H]⁺/Rt (min)): 363.1/0.66

¹H-NMR (400 MHz, DMSO-d₆): δ11.00 (1H, s), 9.01 (1H, d, J=1.8 Hz), 8.30 (1H, dd, J=7.9, 1.8 Hz), 7.69 (1H, d, J=1.2 Hz), 7.54 (1H, d, J=7.9 Hz), 7.48 (1H, d, J=1.2 Hz), 7.38-7.30 (2H, m), 5.52 (1H, t, J=6.1 Hz), 5.18 (2H, s), 4.60 (2H, d, J=6.1 Hz).

Examples 11-21

According to the process of Example 10, the compounds of Examples 11-21 were prepared from the corresponding compounds of each Reference Example.

| Examples | chemical structural formula | instrumental analysis data |
|---|---|---|
| 11 | Cl-benzyl-imidazole-NH-C(O)-pyridine-CH₂OH | LC-MS: [M + H]⁺/Rt (min): 343.2/0.611 |
| 12 | F₃C-benzyl-imidazole-NH-C(O)-pyridine-CH₂OH | ¹H-NMR (400 MHz, DMSO-d₆): 10.99 (1H, s), 9.01 (1H, d, J = 1.8 Hz), 8.30 (1H, dd, J = 8.5, 1.8 Hz), 7.73-7.72 (2H, m), 7.70-7.68 (1H, m), 7.64-7.59 (2H, m), 7.54 (1H, d, J = 8.5 Hz), 7.47 (1H, d, J = 1.2 Hz), 5.51 (1H, t, J = 6.1 Hz), 5.31 (2H, s), 4.60 (2H, d, J = 6.1 Hz). LC-MS: [M + H]⁺/Rt (min): 377.3/0.672 |

| Examples | chemical structural formula | instrumental analysis data |
| --- | --- | --- |
| 13 | | LC-MS:<br>[M + H]⁺/Rt (min): 377.2/0.637 |
| 14 | | LC-MS:<br>[M + H]⁺/Rt (min): 403.3/0.712 |
| 15 | | $^1$H-NMR (400 MHz, DMSO-d$_6$): 9.88 (1H, s), 9.06 (1H, s), 8.22-8.18 (1H, m), 7.72 (1H, d, J = 8.4 Hz), 7.61 (1H, d, J = 8.0 Hz), 7.54-7.44 (4H, m), 7.39 (1H, d, J = 8.0 Hz), 5.92 (1H, s), 5.64 (1H, s), 5.61 (2H, s), 4.61(2H, s).<br>LC-MS:<br>[M + H]⁺/Rt (min): 403.3/0.745 |
| 16 | | $^1$H-NMR (400 MHz, DMSO-d$_6$): 11.03 (1H, s), 9.03 (1H, d, J = 1.8 Hz), 8.31 (1H, dd, J = 7.9, 2.4 Hz), 7.69 (1H, d, J = 1.8 Hz), 7.51-7.48 (2H, m), 7.38-7.31 (2H, m), 5.18 (2H, s), 4.58 (2H, s), 3.56 (2H, q, J = 6.7 Hz), 1.19 (3H, t, J = 6.7 Hz).<br>LC-MS:<br>[M + H]⁺/Rt (min): 391.3/0.82 |
| 17 | | $^1$H-NMR (400 MHz, DMSO-d$_6$): 11.27 (1H, s), 9.17 (1H, d, J = 1.8 Hz), 8.54 (1H, d, J = 1.8 Hz), 7.75-7.73 (2H, m), 7.70-7.68 (1H, m), 7.64-7.61 (2H, m), 7.49 (1H, d, J = 1.2 Hz), 7.42 (1H, t, J = 54.3 Hz), 5.61 (1H, t, J = 5.8 Hz), 5.31 (2H, s), 4.75 (2H, d, J = 5.8 Hz).<br>LC-MS:<br>[M + H]⁺/Rt (min): 427.2/0.787 |
| 18 | | $^1$H-NMR (400 MHz, DMSO-d$_6$): 11.27 (1H, s), 9.17 (1H, s), 8.54 (1H, s), 7.71 (1H, s), 7.51 (1H, s), 7.42 (1H, t, J = 54.8 Hz), 7.37-7.33 (2H, m), 5.61 (1H, t, J = 5.8 Hz), 5.19 (2H, s), 4.75 (2H, d, J = 5.8 Hz).<br>LC-MS:<br>[M + H]⁺/Rt (min): 413.2/0.751 |
| 19 | | LC-MS:<br>[M + H]⁺/Rt (min): 445.2/0.852 |

| Examples | chemical structural formula | instrumental analysis data |
|---|---|---|
| 20 | | LC-MS:<br>[M + H]+/Rt (min): 378.2/0.713 |
| 21 | | 1H-NMR (400 MHz, DMSO-d6): 10.97 (1H, s), 7.73-7.68 (3H, m), 7.64-7.57 (2H, m), 7.45 (1H, s), 6.81 (1H, s), 5.73 (1H, t, J = 5.8 Hz), 5.30 (2H, s), 4.60 (2H, d, J = 5.8 Hz).<br>LC-MS:<br>[M + H]+/Rt (min): 367.2/0.735 |

Example 22

N-[6-(Hydroxymethyl)pyridin-3-yl]-1-(3,4,5-trifluorobenzyl)-1H-imidazole-4-carboxamide

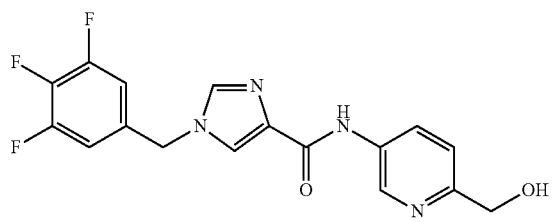 [SMILES: O=C(Nc1ccc(CO)nc1)c1cn(Cc2cc(F)c(F)c(F)c2)cn1]

To a solution of the compound of Reference Example 49-2 (138 mg) and the compound of Reference Example 50 (141 mg) in DMF (15 mL) were added EDCI.HCl (124 mg), HOBt (87 mg), and N,N-diisopropylethylamine (0.188 mL), and the mixture was stirred at 80° C. for 6 hours. To the reaction mixture were then added water and aqueous sodium, hydroxide solution, and the mixture was extracted with chloroform. The organic layer was washed with brine, dried over magnesium sulfate, filtered, and then concentrated in vacuo. The resulting residue was dissolved in methanol (5 mL), and 2 mol/L hydrochloric acid/methanol (0.81 mL) was added thereto, and then the mixture was stirred at 40° C. for 5 hours. To the reaction mixture was added water and then aqueous sodium hydroxide solution, and the mixture was extracted with chloroform. The organic layer was washed with brine, dried over magnesium sulfate, filtered, and then concentrated in vacuo. The residue was purified by silica gel column chromatography (chloroform/methanol) to give the title compound. (86.4 mg).
LC-MS ([M+H]+/Rt (min)): 363.2/0.640
1H-NMR (400 MHz, DMSO-d6): δ10.06 (1H, s), 8.84 (1H, s), 8.19-8.14 (1H, m), 7.97-7.95 (2H, m), 7.42-7.34 (3H, m), 5.31-5.26 (1H, m), 5.24 (2H, s), 4.48 (2H, d, J=4.8 Hz).

Example 23

N-[2-(hydroxymethyl)quinolin-6-yl]-1-(3,4,5-trifluorobenzyl)-1H-imidazole-4-carboxamide

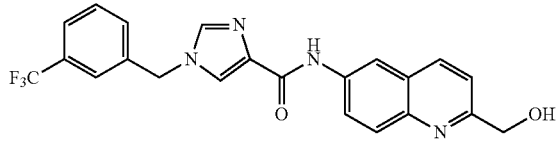 [SMILES: O=C(Nc1ccc2nc(CO)ccc2c1)c1cn(Cc2cccc(C(F)(F)F)c2)cn1]

According to the process of Example 22, the title compound was prepared from the compounds of Reference Examples 49-2 and 51.
LC-MS ([M+H]+/Rt (min)): 413.3/0.673
1H-NMR (400 MHz, DMSO-d6): δ10.13 (1H, s), 8.49 (1H, d, J=2.0 Hz), 8.24 (1H, d, J=9.2 Hz), 8.04 (1H, dd, J=9.2, 2.0 Hz), 8.00 (1H, s), 7.98 (1H, s), 7.85 (1H, d, J=8.8 Hz), 7.57 (1H, d, J=8.8 Hz), 7.44-7.38 (2H, m), 5.50-5.46 (1H, m), 5.25 (2H, s), 4.60 (2H, d, J=5.6 Hz).

Example 24

6-(Aminomethyl)-N-{1-[3-(trifluoromethyl)benzyl]-1H-imidazol-4-yl}nicotinamide ditrifluoroacetate

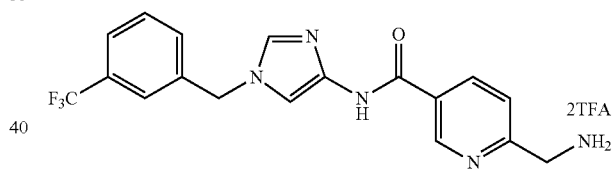

According to the process of Reference Example 45-2, the title compound was prepared from the compound of Reference Example 39-2.
LC-MS ([M+H]+/Rt (min)): 376.2/0.597

Example 25

6-[(Acetylamino)methyl]-N-{1-[3-(trifluoromethyl)benzyl]-1H-imidazol-4-yl}nicotinamide

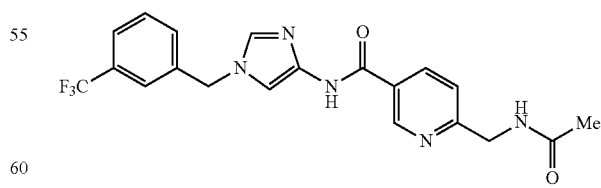

To a solution of the compound of Example 24 (30 mg) in THF (1 mL) were added triethylamine (0.111 mL) and anhydrous acetic acid. (0.038 mL), and the mixture was stirred at room temperature for 1.5 hours. To the reaction mixture was added water, and the mixture was extracted with ethyl acetate. The organic layer was washed with brine, dried over anhydrous sodium sulfate, filtered, and then concentrated in vacuo.

The residue was purified by silica gel column chromatography (chloroform/methanol) to give the title compound (28 mg).

LC-MS ([M+H]$^+$/Rt (min)): 418.3/0.669

$^1$H-NMR (400 MHz, DMSO-d$_6$): δ11.02 (1H, s), 9.01 (1H, d, J=1.8 Hz), 8.48 (1H, t, J=6.1 Hz), 8.26 (1H, dd, J=8.3, 1.8 Hz), 7.73-7.68 (3H, m), 7.64-7.59 (2H, m), 7.46 (1H, s), 7.35 (1H, d, J=8.3 Hz), 5.30 (2H, s), 4.37 (2H, d, J=6.1 Hz), 1.90 (3H, s).

Example 26

6-[(Methylamino)methyl]-N-{1-[3-(trifluoromethyl)benzyl]-1H-imidazol-4-yl}nicotinamide

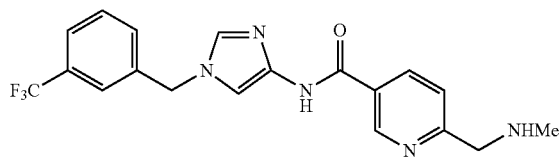 [SMILES: CNCc1ccc(C(=O)Nc2cn(Cc3cccc(C(F)(F)F)c3)cn2)cn1]

To a solution of the compound of Reference Example 58 (155 mg) in DMF (1 mL) were added potassium carbonate (59 mg) and thiophenol (30 μL), and the mixture was stirred at room temperature for 3 hours. To the reaction mixture was added diethyl ether, and the organic layer was extracted with 0.1 mol/L hydrochloric acid. To the resulting aqueous layer was added saturated aqueous sodium hydrogen carbonate solution to adjust pH to 9, and the mixture was extracted with chloroform. The organic layer was dried over anhydrous sodium sulfate, filtered, and concentrated in vacuo, and then the resulting residue was purified by silica gel column chromatography (chloroform/methanol) to give the title compound (93 mg).

LC-MS ([M+H]$^+$/Rt (min)): 195.7/0.628

Examples 27-29

According to the process of Reference Example 32, the compounds of Examples 27-29 were prepared from the corresponding compounds of each Reference Example.

| Examples | chemical structural formula | LC-MS: [M + H]$^+$/Rt (min) |
|---|---|---|
| 27 | | 425.3/0.697 |
| 28 | | 441.2/0.791 |
| 29 | | 485.2/0.742 |

Example 30

5-Fluoro-6-(hydroxymethyl)-N-{1-[3-(trifluoromethyl)benzyl]-1H-imidazol-4-yl}nicotinamide

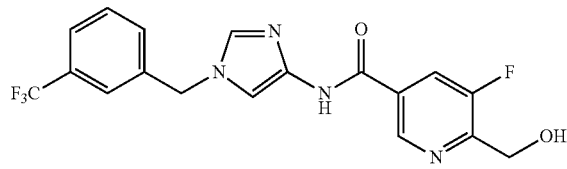 [SMILES: O=C(Nc1cn(Cc2cccc(C(F)(F)F)c2)cn1)c1cnc(CO)c(F)c1]

To a solution of the compound of Example 27 (51 mg) in THF (2 mL)/water (1 ml) was added sodium periodate (77 mg), and the mixture was stirred at room temperature for 1 hour. To the reaction mixture was added water, and the mixture was extracted with ethyl acetate. The organic layer was washed with brine, dried over anhydrous sodium sulfate, filtered, and then concentrated in vacuo. To a solution of the resulting residue in methanol (1 mL) was added sodium borohydride (4 mg), and the mixture was stirred at room temperature for 10 minutes. To the reaction mixture was added saturated aqueous ammonium chloride solution, and the mixture was stirred at room temperature for 5 minutes, and then concentrated in vacuo. To the residue was added water, and the mixture was placed in an ultrasound bath, and thea the precipitate was collected on a filter. The resulting filter cake was washed with water and methanol, and then dried at 50° C. in vacuo to give the title compound (37 mg).

LC-MS ([M+H]$^+$/Rt (min)): 395.3/0.739

Examples 31-39

According to the process of Example 30, the compounds of Examples 31-39 were prepared from the compounds of Examples 28-29 and the corresponding compounds of each Reference Example.

| Examples | chemical structural formula | instrumental analysis data |
|---|---|---|
| 31 | | $^1$H-NMR (400 MHz, DMSO-d$_6$): 11.17 (1H, s), 9.01 (1H, d, J = 1.8 Hz), 8.39 (1H, d, J = 1.8 Hz), 7.76-7.68 (3H, m), 7.64-7.59 (2H, m), 7.48 (1H, s), 5.34 (1H, t, J = 6.1 Hz), 5.31 (2H, s), 4.67 (2H, d, J = 6.1 Hz). LC-MS: [M + H]$^+$/Rt (min): 411.2/0.791 |
| 32 | | LC-MS: [M + H]$^+$/Rt (min): 455.2/0.806 |
| 33 | | LC-MS: [M + H]$^+$/Rt (min): 407.3/0.711 |
| 34 | | LC-MS: [M + H]$^+$/Rt (min): 391.2/0.646 |
| 35 | | LC-MS: [M + H]$^+$/Rt (min): 391.2/0.669 |
| 36 | | LC-MS: [M + H]$^+$/Rt (min): 411.2/0.743 |

| Examples | chemical structural formula | instrumental analysis data |
|---|---|---|
| 37 | | LC-MS: [M + H]⁺/Rt (min): 367.2/0.681 |
| 38 | | LC-MS: [M + H]⁺/Rt (min): 441.1/0.769 |
| 39 | | $^1$H-NMR (400 MHz, DMSO-$d_6$): 10.97 (1H, s), 8.87 (1H, d, J = 1.8 Hz), 8.10 (1H, d, J = 1.8 Hz), 7.69 (1H, d, J = 1.2 Hz), 7.48 (1H, d, J = 1.2 Hz), 7.38-7.31 (2H, m), 5.18 (2H, s), 5.11 (1H, t, J = 5.5 Hz), 4.60 (2H, d, J = 5.5 Hz), 2.35 (3H, s). LC-MS: [M + H]⁺/Rt (min): 377.2/0.631 |

Example 40

2-(Hydroxymethyl)-N-{1-[3-(trifluoromethyl)benzyl]-1H-imidazol-4-yl}-1,3-thiazole-5-carboxamide

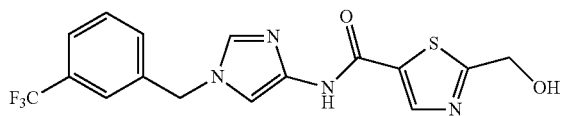 [SMILES: O=C(Nc1cn(Cc2cccc(C(F)(F)F)c2)cn1)c1cnc(CO)s1]

To a solution of the compound of Reference Example 27 (211 mg) in acetone (5 mL)/water (2.5 mL) were added osmium tetroxide (2.5 wt % in tert-butanol, 0.525 mL) and sodium periodate (358 mg), and the mixture was stirred at room temperature for 4 hours. To the reaction mixture were added saturated aqueous sodium thiosulfate solution and water, and the mixture was extracted with ethyl acetate. The organic layer was washed with brine, dried over sodium sulfate, filtered, and then concentrated in vacuo. The residue was roughly purified by silica gel column chromatography (chloroform/methanol). To the resulting compound were added methanol (2 mL) and sodium borohydride (3 mg), and then the mixture was stirred at room temperature for 18.5 hours. To the reaction mixture was added saturated aqueous ammonium chloride solution and water, and then the mixture was extracted with ethyl acetate. The organic was washed with brine, dried over sodium sulfate, filtered, and then concentrated in vacuo. The residue was purified by silica gel column chromatography (chloroform/methanol) to give the title compound (8 mg).
LC-MS ([M+H]⁺/Rt (min)): 383.2/0.705
$^1$H-NMR (400 MHz, DMSO-$d_6$): δ9.77 (1H, s), 8.31 (1H, s), 7.72-7.71 (2H, m), 7.70-7.67 (1H, m), 7.62-7.60 (2H, m), 7.40 (1H, d, J=1.8 Hz), 6.19 (1H, t, J=5.8 Hz), 5.30 (2H, s), 4.77 (2H, d, J=5.8 Hz).

Example 41

5-Chloro-6-(hydroxymethyl)-N-[1-(3,4,5-(trifluorobenzyl)-1H-imidazol-4-yl]-nicotinamide

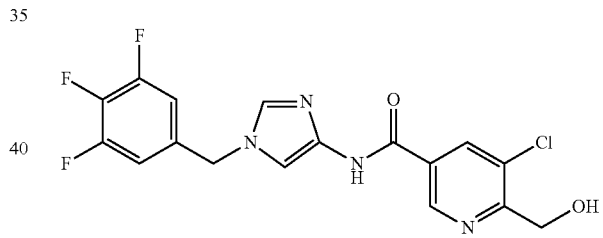

According to the process of Example 40, the title compound was prepared from the compound of Reference Example 30.
LC-MS ([M+H]⁺/Rt (min)): 397.2/0.750

Example 42

6-(Hydroxymethyl)-5-methyl-N-{1-[3-(trifluoromethyl)benzyl]-1H-imidazol-4-yl}-nicotinamide

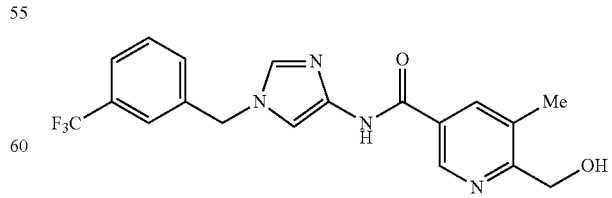

According to the process of Reference Example 31, the title compound was prepared from the compound of Example 32.
LC-MS ([M+H]⁺/Rt (min)): 391.3/0.671

¹H-NMR (400 MHz, DMSO-d₆): δ10.96 (1H, s), 8.86 (1H, d, J=1.8 Hz), 8.10 (1H, d, J=1.8 Hz), 7.73-7.68 (3H, m), 7.64-7.59 (2H, m), 7.46 (1H, d, J=1.8 Hz), 5.31 (2H, s), 5.12 (1H, t, J=5.8 Hz), 4.60 (2H, d, J=5.8 Hz), 2.35 (3H, s).

Example 43

5-Ethenyl-6-(hydroxymethyl)-N-{1-[3-(trifluoromethyl)benzyl]-1H-imidazol-4-yl}-nicotinamide

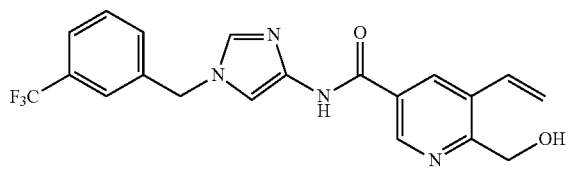 [SMILES: C=Cc1cc(C(=O)Nc2cn(Cc3cccc(C(F)(F)F)c3)cn2)cnc1CO]

According to the process of Reference Example 20, the title compound was prepared from the compound of Example 32.
LC-MS ([M+H]⁺/Rt (min)): 403.3/0.744

Example 44

5-Ethenyl-6-(hydroxymethyl)-N-{1-[3-(trifluoromethyl)benzyl]-1H-imidazol-4-yl}-nicotinamide

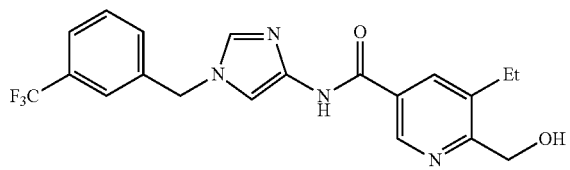 [SMILES: CCc1cc(C(=O)Nc2cn(Cc3cccc(C(F)(F)F)c3)cn2)cnc1CO]

To a suspension of platinum oxide (30 mg) in ethyl acetate (2 mL)/methanol (1 mL) was added the compound of Example 43 (27 mg), and the mixture was stirred under hydrogen atmosphere at room temperature for 4 hours. The reaction. mixture was filtered. through Celite® and washed with ethyl acetate. The filtrate was concentrated in vacuo, and the resulting residue was purified by silica gel column chromatography (hexane/ethyl acetate, ethyl acetate/methanol) to give the title compound (16 mg).
LC-MS ([M+H]⁺/Rt (min)): 405.3/0.708

Example 45

5-Amino-6-(hydroxymethyl)-N-{1-[3-(trifluoromethyl)benzyl]-1H-imidazol-4-yl}-nicotinamide

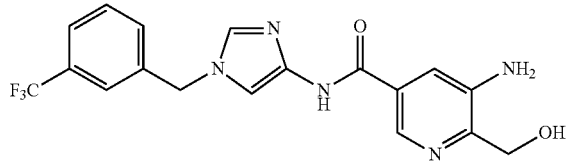

To a suspension of the compound of Reference Example 41-6 (13 mg) in THF (0.5 mL)/methanol (0.5 mL) was added 2 mol/L aqueous sodium hydroxide solution (0.031 mL), and the mixture was stirred at 60° C. for 3 hours and then at 90° C. for 6.5 hours. The reaction mixture was cooled to room temperature, and water was added thereto, and then the mixture was stirred at room temperature for 5 minutes. The resulting solid was collected on a filter, washed with water, and dried at 50° C. in vacuo to give the title compound (7 mg).
LC-MS ([M+H]⁺/Rt (min)): 392.2/0.647
¹H-NMR (400 MHz, DMSO-d₆): δ10.79 (1H, s), 8.29 (1H, d, J =1.8 Hz), 7.72-7.68 (3H, m), 7.64-7.581 (2H, m), 7.43 (1H, d, J=1.2 Hz), 7.42 (1H, d, J=1.8 Hz), 5.36 (2H, s), 5.30 (2H, s), 5.18 (1H, t, J=5.5 Hz), 4.52 (2H, d, J=5.5 Hz)

Example 46

5-Amino-6-(hydroxymethyl)-N-[1-(3,4,5-(trifluorobenzyl)-1H-imidazol-4-yl]-nicotinamide

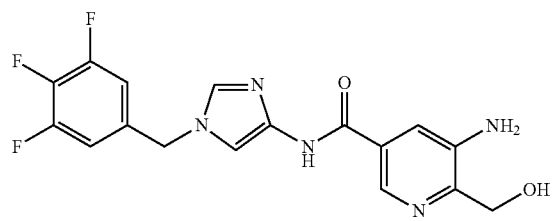

According to the process of Example 45, the title compound was prepared from the compound of Reference Example 42.
LC-MS ([M+H]⁺/Rt (min)): 378.2/0.603

Example 47

4-(Hydroxymethyl)-5-methyl-N-[1-(3,4,5-(trifluorobenzyl)-1H-imidazol-4-yl]-1,3-thiazole-2-carboxamide

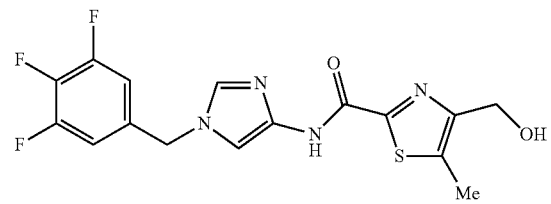 [SMILES: Cc1sc(C(=O)Nc2cn(Cc3cc(F)c(F)c(F)c3)cn2)nc1CO]

To the compound of Reference Example 46-2 (219 mg) was added hydrogen chloride (2 mol/L in methanol, 2 mL), and the mixture was added at room temperature for 1 hour. To the reaction mixture were added saturated aqueous sodium hydrogen carbonate solution, water, and ethyl acetate, and then the mixture was stirred at room temperature for 10 minutes. The resulting precipitate was collected on a filter, washed with water and hexane, and then dried at 50° C. in vacuo to give the title compound (84 mg).
LC-MS ([M+H]⁺/Rt (min)): 383.2/0.769

Example 48

5-(Hydroxymethyl)-4-methyl-N-[1-(3,4,5-trifluorobenzyl)-1H-imidazol-4-yl]-1,3-thiazole-2-carboxamide

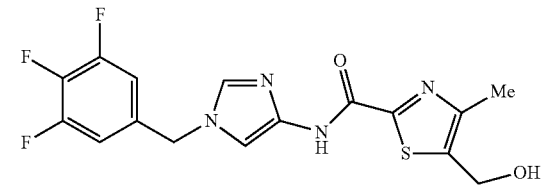 [SMILES: Cc1nc(C(=O)Nc2cn(Cc3cc(F)c(F)c(F)c3)cn2)sc1CO]

According to the process of Example 47, the title compound was prepared from the compound of Reference Example 47.
LC-MS ([M+H]+/Rt (min)): 383.2/0.743

Example 49

5-(Difluoromethyl)-6-{[(4-methoxybenzyl)oxy]methyl}-N-[1-(3,4,5-trifluorobenzyl)-1H-imidazol-4-yl]nicotinamide

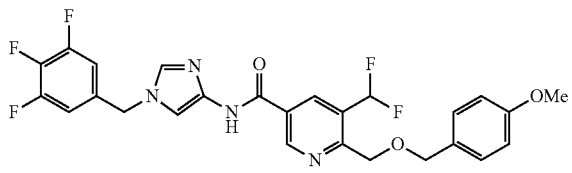 [SMILES: COc1ccc(COCc2ncc(C(=O)Nc3cn(Cc4cc(F)c(F)c(F)c4)cn3)cc2C(F)F)cc1]

To a solution of the compound of Reference Example 60-5 (2.49 g) in methanol (25 mL) was added 2 mol/L aqueous sodium. hydroxide solution (6.8 mL), and the mixture was stirred at room temperature for 1 hour. To the reaction solution was added 4 mol/L hydrochloric acid (2.1 mL) to adjust pH to 8. The reaction mixture was concentrated in vacuo, and to a suspension of the resulting residue in THF (30 mL) were added DIEA (1.43 mL) and diphenyl chlorophosphate (1.70 mL), and then the mixture was stirred for 2 hours. DIEA (1.43 mL) and diphenyl chlorophosphate (1.70 mL) were added thereto, and the mixture was additionally stirred for 1 hour. DIEA (2.86 mL) and the compound. of Reference Example 6 (1.97 g) were added thereto, and. the mixture was stirred at room. temperature for 20 hours. 2 mol/L aqueous sodium hydroxide solution (10 mL) was added thereto, and the mixture was stirred at room temperature for 2 hours. 2 mol/L aqueous sodium hydroxide solution (5 mL) was added thereto, and the mixture was additionally stirred for 1.5 hours. Methanol (15 mL) was added thereto, and the mixture was stirred. at room temperature for 1 hour. The reaction mixture was concentrated in vacuo, and the residue was diluted with water and then extracted with ethyl acetate. The organic layer was washed with saturated aqueous sodium carbonate solution and brine, dried over sodium sulfate, filtered, and then concentrated in vacuo. The residue was purified by silica gel column chromatography (hexane/ethyl acetate, ethyl acetate/methanol) to give the title compound (1.88 g).
LC-MS ([M+H]+/Rt (min)): 534.3/1.021

Example 50

5-(Difluoromethy)-6-(hydroxymethyl)-N-[1-(3,4,5-trifluorobenzyl)-1H-imidazol-4-yl]nicotinamide

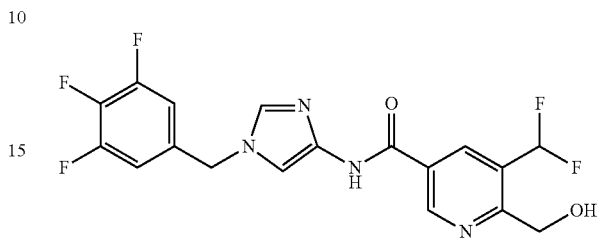

To a solution of the compound of Example 49 (1.88 g) in chloroform (10 mL) was added TFA (2 mL), and the mixture was stirred. at room temperature for 2 hours. To the reaction solution was added TFA (3 mL), and the mixture was additionally stirred for 3 hours. The reaction mixture was concentrated in vacuo, and to the residue were added water and saturated aqueous sodium carbonate solution, and thea the mixture was extracted with chloroform. The organic layer was washed with saturated. aqueous sodium carbonate solution. and brine, dried over sodium sulfate, filtered, and then concentrated in vacuo. The residue was purified by silica gel column chromatography (chloroform/methanol) to give the title compound (0.53 g).
$^1$H-NMR (400 MHz, DMSO-$d_6$): δ11.27 (1H, s), 9.17 (1H, s), 8.54 (1H, s), 7.71 (1H, s), 7.51 (1H, s), 7.42 (1H, t, J=54.8 Hz), 7.37-7.33 (2H, m), 5.61 (1H, t, J=5.8 Hz), 5.91 (2H, s), 4.75 (2H, d, J=5.8 Hz).
LC-MS ([M+H]+/Rt (min)): 413.2/0.751

Examples 51-52

According the process of Example 49, the compounds of Examples 51-52 were prepared from the compound of Reference Example 4 and each corresponding starting compound.

| Examples | chemical structural formula | LC-MS: [M + H]+/Rt (min) |
|---|---|---|
| 51 | | 403.3/0.678 |
| 52 | | 437.2/0.782 |

Example 53

(2E)-3-[6-(2-Hydroxypropan-2-yl)pyridin-3-yl]-N-{1-[3-(trifluoromethyl)benzyl]-1H-imidazol-4-yl}prop-2-enamide

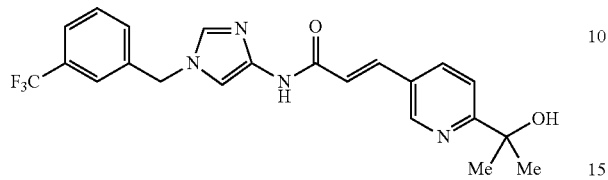

To a solution of the compound of Reference Example 65-2 (30 mg) in THF (2 mL) was added methylmagnesium bromide (0.97 mol/L in THF, 0.36 mL), and the mixture was stirred at room temperature for 1.5 hours. Methylmagnesium bromide (0.97 mol/L in THF, 0.36 mL) was added thereto, and the mixture was additionally stirred at room temperature for 16 hours. To the reaction mixture was added saturated aqueous ammonium chloride solution, and the mixture was extracted with ethyl acetate. The organic layer was washed with brine, dried over anhydrous sodium sulfate, filtered, and then concentrated in vacuo. The resulting residue was purified by silica gel column chromatography (chloroform/methanol) to give the title compound (13 mg).
LC-MS ([M+H]$^+$/Rt (min)): 431.3/0.722
$^1$H-NMR (400 MHz, DMSO-d$_6$): δ10.62 (1H, s), 8.64 (1H, s), 7.92 (1H, dd, J=8.2, 2.1 Hz), 7.70-7.57 (6H, m), 7.50 (1H, d, J=15.9 Hz), 7.38 (1H, s), 6.92 (1H, d, J=15.9 Hz), 5.29 (2H, s), 5.25 (1H, s), 1.43 (6H, s).

Examples 54-55

According to the process of Reference Example 1, the compounds of Examples 54-55 were prepared from the compound of Reference Example 64-4 and each corresponding starting compound.

| Examples | chemical structural formula | LC-MS: [M + H]$^+$/Rt (min) |
|---|---|---|
| 54 | ![structure] | 395.2/0.698 |
| 55 | ![structure] | 393.2/0.732 |

Examples 56-84

According to the process of Reference Example 1, the compounds of Examples 56-84 were prepared from the compound of Reference Example 64-4 and each corresponding starting compound.

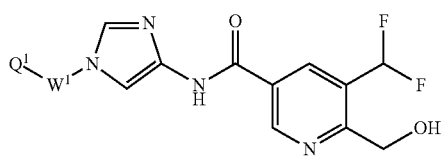

| Examples | Q$^1$—W$^1$— | LC-MS: [M + H]$^+$/ Rt (min) |
|---|---|---|
| 56 | ![benzyl] | 359.2/0.672 |
| 57 | ![4-F-3-CF3-benzyl] | 445.3/0.833 |
| 58 | ![3-Br-benzyl] | 437.2/0.785 |
| 59 | ![2-Me-benzyl] | 373.3/0.764 |

101
-continued
| Examples | Q¹—W¹— | LC-MS: [M + H]⁺/ Rt (min) |
|---|---|---|
| 60 | 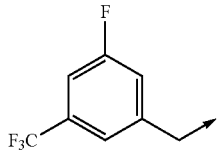 | 445.3/0.840 |
| 61 | 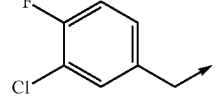 | 411.2/0.810 |
| 62 | 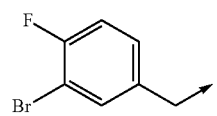 | 455.2/0.837 |
| 63 | 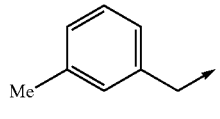 | 373.3/0.745 |
| 64 | 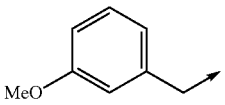 | 389.3/0.697 |
| 65 | 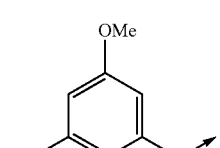 | 457.3/0.849 |
| 66 | 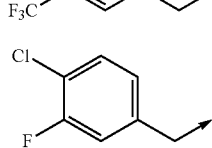 | 411.2/0.796 |
| 67 | 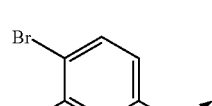 | 455.2/0.815 |
| 68 | 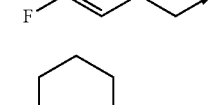 | 365.2/0.776 |
| 69 | 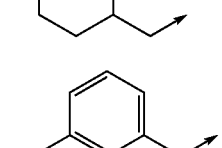 | 451.3/0.906 |
| 70 | 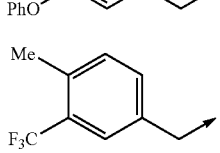 | 441.3/0.874 |
| 71 | 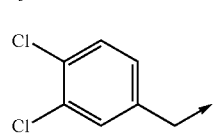 | 427.2/0.852 |
102
-continued
| Examples | Q¹—W¹— | LC-MS: [M + H]⁺/ Rt (min) |
|---|---|---|
| 72 | 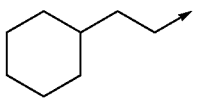 | 379.3/0.870 |
| 73 | 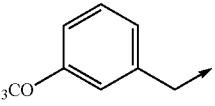 | 443.3/0.841 |
| 74 | 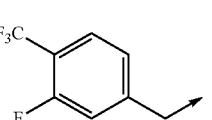 | 445.3/0.847 |
| 75 | 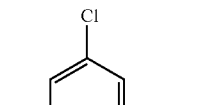 | 427.2/0.866 |
| 76 | 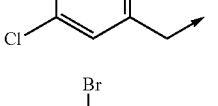 | 455.2/0.819 |
| 77 | 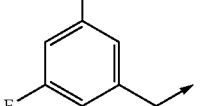 | 419.3/0.715 |
| 78 | 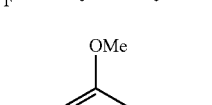 | 411.2/0.802 |
| 79 | 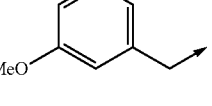 | 395.2/0.739 |
| 80 | 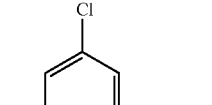 | 473.1/0.875 |
| 81 | 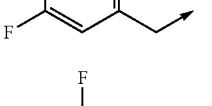 | 360.2/0.416 |
| 82 | 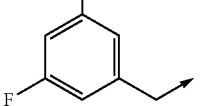 | 417.2/0.788 |

| Examples | Q¹—W¹— | LC-MS: [M + H]⁺/ Rt (min) |
|---|---|---|
| 83 | F₃C-phenyl-CH₂CH₂- | 441.3/0.828 |
| 84 | naphthalen-2-ylmethyl- | 409.3/0.817 |

Example 85

6-(Hydroxymethyl)-N-[1-(3,4,5-trifluorobenzyl)-1H-imidazol-4-yl]pyridazine-3-carboxamide

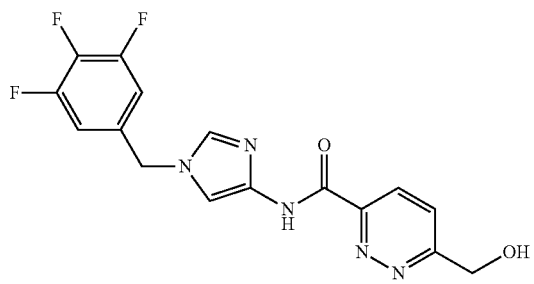 [SMILES: O=C(Nc1cn(Cc2cc(F)c(F)c(F)c2)cn1)c1ccc(CO)nn1]

According to the process of Example 40, the title compound was prepared from the compound of Reference Example 68-2.
LC-MS ([M+H]⁺/Rt (min)): 364.2/0.706

Test Example 1: Inhibition of Sphere-Forming Ability of Cancer Cells

The reliable methods established for measuring the self-renewal ability of cells which is one of the CSC's properties include a method for measuring the sphere-forming ability of cancer cells in non-adherent condition in the absence of serum (Cancer Res 65, 5506-5511 (2005)). HCT-116 cells were available from the American Type Culture Collection (ATCC). HCT-116 cells were cultured at 37° C. and 5% $CO_2$ using the McCoy's 5a medium containing 10% fetal bovine serum (FBS) and 1% penicillin/streptomycin. HCT-116 cells were seeded in a 384 Well Black Clear Bottom Ultra-Low Attachment Microplate (Corning Cat. No. 3827) in an amount of 350-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), and 1% penjcillin/streptomycin. The test compounds were added into each well to adjust the final concentration of DMSO to 0.1%, and the cells were cultured for 4 days. The number of viable cells in each well was then measured with CellTiter-Glo® Luminescent Cell Viability Assay (Promega) to calculate the concentration of each test compound for 50% inhibition of cell proliferation (Sphere IC₅₀ value; μmol/L).

The experiment of Test Example 1 was performed for the compounds of each Example. The concentrations of each test compound for 50% inhibition of cell profeliration (Sphere $IC_{50}$ value; μmol/L) are shown in the following Table.

| Examples | IC₅₀ (μmol/L) |
|---|---|
| 1 | 0.030 |
| 2 | 0.629 |
| 3 | <0.01 |
| 4 | <0.01 |
| 5 | 8.400 |
| 6 | 3.650 |
| 7 | 0.024 |
| 8 | 0.077 |
| 9 | 5.035 |
| 10 | 0.007 |
| 11 | 0.056 |
| 12 | <0.01 |
| 13 | 0.675 |
| 14 | 6.039 |
| 15 | 0.710 |
| 16 | 0.892 |
| 17 | <0.01 |
| 18 | <0.01 |
| 19 | 0.070 |
| 20 | 0.053 |
| 21 | 0.653 |
| 22 | <0.01 |
| 23 | 0.079 |
| 24 | 0.061 |
| 25 | 4.483 |
| 26 | 0.824 |
| 27 | 0.695 |
| 28 | 0.847 |
| 29 | 0.633 |
| 30 | 0.069 |
| 31 | <0.01 |
| 32 | <0.01 |
| 33 | 9.795 |
| 34 | 7.394 |
| 35 | 3.763 |
| 36 | 0.074 |
| 37 | 0.238 |
| 38 | 0.061 |
| 39 | <0.01 |
| 40 | 0.122 |
| 41 | 0.051 |
| 42 | <0.01 |
| 43 | 5.597 |
| 44 | 0.758 |
| 45 | 0.029 |
| 46 | 0.010 |
| 47 | 0.669 |
| 48 | 0.095 |
| 51 | 0.07 |
| 52 | 0.05 |
| 53 | 7.20 |
| 54 | 0.148 |
| 55 | 0.075 |
| 56 | 0.430 |
| 57 | <0.010 |
| 58 | 0.070 |
| 59 | 0.090 |
| 60 | 0.030 |
| 61 | <0.010 |
| 62 | <0.010 |
| 63 | 0.690 |
| 64 | 0.090 |
| 65 | 0.630 |
| 66 | 0.070 |
| 67 | 0.040 |
| 68 | 0.280 |
| 69 | 0.070 |
| 70 | <0.010 |
| 71 | <0.010 |
| 72 | 0.810 |
| 73 | 0.080 |
| 74 | 0.380 |
| 75 | <0.010 |
| 76 | 0.050 |

-continued

| Examples | IC$_{50}$ (μmol/L) |
|---|---|
| 78 | 0.050 |
| 79 | 0.080 |
| 82 | 0.720 |
| 83 | 0.700 |
| 85 | 0.020 |

Test Example 2: Test for Inhibiting Sphere-Forming Ability of Cancer Cells (in the Presence of BSA)

HCT-116 cells were available from the American Type Culture Collection (ATCC). HCT-116 cells were cultured at 37° C. and 5% CO$_2$ using the McCoy's 5a medium containing 10% fetal bovine serum (FBS) and 1% penicillin/streptomycin. HCT-116 cells were seeded in a 384 Well Black Clear Bottom Ultra-Low Attachment Microplate (Corning Cat. No. 3827) in an amount of 30-800 cells/well using the DMEM/F12 medium containing 2% B27 supplement (GIBCO), 20 ng/mL epidermal growth factor (EGF) (peprotech), 10 ng/mL basic fibroblast growth factor (bFGF) (peprotech), 5 μg/mL insulin (Sigma), 5% bovine serum albumin (BSA), and 1% penicillin/streptomycin. The test compounds were added into each well to adjust the final concentration of DMSO to 0.1%, and the cells were cultured for 4 days. The number of viable cells in each well was then measured with CellTiter-Glo® Luminescent Cell Viability Assay (Promega) to calculate the concentration of each test compound for 50% inhibition of cell proliferation (Sphere IC$_{50}$ value; μmol/L).

The experiment of Test Example 2 was performed for the compounds of each Example. The concentrations of each test compound for 50% inhibition of cell profeliration (Sphere IC$_{50}$ value; μmol/L) are shown in the following Table.

| Examples | IC$_{50}$ (μmol/L) |
|---|---|
| 1 | 0.350 |
| 2 | 0.605 |
| 3 | 0.051 |
| 4 | 0.061 |
| 6 | 6.970 |
| 7 | 0.520 |
| 8 | 0.578 |
| 10 | 0.007 |
| 12 | 0.060 |
| 13 | 0.735 |
| 15 | 5.766 |
| 16 | 1.446 |
| 17 | 0.057 |
| 18 | 0.053 |
| 19 | 0.403 |
| 20 | 0.313 |
| 21 | 0.767 |
| 22 | <0.01 |
| 23 | 0.084 |
| 24 | 0.696 |
| 25 | 4.968 |
| 27 | 6.230 |
| 28 | 4.585 |
| 29 | 3.501 |
| 30 | 0.563 |
| 31 | <0.01 |
| 32 | 0.068 |
| 35 | 6.106 |
| 36 | 0.481 |
| 37 | 0.451 |
| 38 | 0.081 |
| 39 | <0.01 |
| 40 | 0.629 |
| 41 | 0.059 |
| 42 | 0.060 |
| 43 | 6.511 |
| 44 | 5.112 |
| 45 | 0.059 |
| 46 | 0.057 |
| 47 | 5.455 |
| 48 | 0.571 |
| 51 | 0.63 |
| 52 | 0.41 |
| 53 | >10 |
| 54 | 0.603 |
| 55 | 0.619 |
| 56 | 0.540 |
| 57 | 0.050 |
| 58 | 0.080 |
| 59 | 0.100 |
| 60 | 0.060 |
| 61 | 0.030 |
| 62 | 0.050 |
| 63 | 0.600 |
| 64 | 0.290 |
| 65 | 0.660 |
| 66 | 0.060 |
| 67 | 0.070 |
| 68 | 0.540 |
| 69 | 0.330 |
| 70 | 0.060 |
| 71 | 0.060 |
| 72 | 0.670 |
| 73 | 0.080 |
| 74 | 0.670 |
| 75 | 0.050 |
| 76 | 0.060 |
| 78 | 0.060 |
| 79 | 0.060 |
| 82 | 0.470 |
| 83 | 0.580 |
| 85 | 0.030 |

Test Example 3. Pharmacokinetic Assay in Mouse

A 7-week-old mouse (BALB/cAnNCrlCrlj, female, CHARLES RIVER LABORATORIES JAPAN, INC.) receives single oral administration of each compound suspended in 0.5% methylcellulose solution in a dose of 10 mg/kg or 100 mg/kg. Blood is collected from the mouse 0.5, 1, 2, 4, 8 and 24 hours after the administration, and plasma from the blood is collected by centrifugation. The area under the plasma concentration-time curve (AUC) is calculated on the basis of the concentration changes to calculate the bioavailability of each compound according to the following formula: Bioavailabity (%)=AUC after oral administration/AUC after intravenous administration×100

Plasma is deproteinized by adding methanol at the final concentration of 80%, centrifuging the methanol solution, and filtrating the contrifuged solution, and then the present compound in the deproteinized plasma is detected and quantified with an LC-MS/MS (API4000, AB SCIEX). When the present compound is quantified, a calibration curve is prepared based on the mouse plasma added with a given amount of the compound. Bezafibrate is used as internal standard.

Test Example 4. Anti-Tumor Effect to HCT-116 Tumor-Hearing Mouse

The present compound can be used to evaluate the anti-tumor effect thereof. A 4 to 7-week-old nude mouse (BALB/ cAnNCrj-nu/nu, female, CHARLES RIVER LABORATORIES JAPAN, INC.) received intradermal transplantation of HCT-116 cells (ATCC) in an amount of 3×10$^6$ cells/mouse around the ventral portion. The engraftment of HCT-116 cells was observed 5 to 14 days after the transplantation, and then each compound suspended in a solvent such as 0.5% methylcellulose solution was orally administered to the mouse in a dose of 1 to 100 mg/kg one to twice daily. The tumor volume was measured over time after the administration. to evaluate the effect for reducing the tumor volume by the administration of each compound. The tumor volume can be calculated from the minor axis and the major axis of the tumor measured with a digital caliper (Mitutoyo) according to the following formula:

$$\text{Tumor volume [mm}^3\text{]} = 0.5 \times \text{minor axis [mm]} \times (\text{major axis [ram]})^2$$

The tumor volume is control administration group treated. with only a solvent such as 0.5% methylcellulose solution was compared with that of the present compound administration group, and T/C value was calculated according the following formula to evaluate the anti-tumor effect of the present compound.
T/C(%) (the tumor volume at the end of administration in the present compound administration group–the tumor volume at the start of administration in the present compound administration group)/(the tumor volume at the end of administration in the control administration group–the tumor volume at the start of administration in the present compound. administration group)×100

The T/C values (%) of the present compound on each dosage and administration period in the HCT-116 tumor-bearing mouse are shown below.

| Examples | dosage (mg/kg) | administration period (day) | T/C (%) |
|---|---|---|---|
| 12 | 100 | 16 | 49 |
| 17 | 30 | 17 | 74 |
| 17 | 100 | 17 | 75 |
| 18 | 30 | 17 | 63 |
| 18 | 100 | 17 | 54 |
| 39 | 30 | 17 | 79 |
| 39 | 100 | 17 | 65 |
| 45 | 30 | 17 | 90 |
| 45 | 100 | 17 | 81 |
| 46 | 30 | 17 | 91 |
| 46 | 100 | 17 | 91 |

INDUSTRIAL APPLICABILITY

The present compound has a potent inhibitory effect on sphere-forming ability of cancer cells, and is useful as an orally-available anti-tumor agent.

The invention claimed is:
1. A compound selected from the group consisting of:
   5-(difluoromethyl)-6-(hydroxymethyl)-N-{1-[3-(trifluoromethyl)benzyl]-1H-imidazol-4-yl}nicotinamide;
   5-(difluoromethyl)-6-(hydroxymethyl)-N-[1-(3,4,5-trifluorobenzyl)-1H-imidazol-4-yl]nicotinamide;
   6-(hydroxymethyl)-5-methyl-N-[1-(3,4,5-trifluorobenzyl)-1H-imidazol-4-yl]nicotinamide;
   5-amino-6-(hydroxymethyl)-N-{1-[3-(trifluoromethyl)benzyl]-1H-imidazol-4-yl}nicotinamide; and
   5-amino-6-(hydroxymethyl)-N-[1-(3,4,5-trifluorobenzyl)-1H-imidazo1-4-yl]nicotinamide,
or a pharmaceutically acceptable salt thereof.

2. The compound of claim 1 wherein the compound is 5-(difluoromethyl)-6-(hydroxymethyl)-N-{1-[3-(trifluoromethyl)benzyl]-1H-imidazol-4-yl}nicotinamide, or a pharmaceutically acceptable salt thereof.

3. The compound of claim 1 wherein the compound is 5-(difluoromethyl)-6-(hydroxymethyl)-N-[1-(3,4,5-trifluorobenzyl)-1H-imidazol-4-yl]nicotinamide, or a pharmaceutically acceptable salt thereof.

4. The compound of claim 1 wherein. the compound is 6-(hydroxymethyl)-5-methyl-N-[1-(3,4,5-trifluorobenzyl)-1H-imidazol-4-yl]nicotinamide, or a pharmaceutically acceptable salt thereof.

5. The compound of claim 1 wherein the compound is 5-amino-6-(hydroxymethyl)-N-{1-[3-(trifluoromethyl)benzyl]-1H-imidazol-4-yl}nicotinamide, or a pharmaceutically acceptable salt thereof.

6. The compound of claim 1 wherein the compound is 5-amino-6-(hydroxymethyl)-N-[1-(3,4,5-trifluorobenzyl)-1H-imidazol-4-yl]nicotinamide, or a pharmaceutically acceptable salt thereof.

7. A method treating cancer which comprises administering a therapeutically effective amount of compound selected from the group consisting of:
   5-(difluoromethyl)-6-(hydroxymethyl)-N-{1-[3-(trifluoromethyl)benzyl]-1H-imidazol-4-yl}nicotinamide;
   5-(difluoromethyl)-6-(hydroxymethyl)-N-[1-(3,4,5-trifluorobenzyl)-1H-imidazol-4-yl]nicotinamide;
   6-(hydroxymethyl)-5-methyl-N-[1-(3,4,5-trifluorobenzyl)-1H-imidazol-4-yl]nicotinamide;
   5-amino-6-(hydroxymethyl)-N-{1-[3-(trifluoromethyl)benzyl]-1H-imidazol-4-yl}nicotinamide; and
   5-amino-6-(hydroxymethyl)-N-[1-(3,4,5-trifluorobenzyl)-1H-imidazol-4-yl]nicotinamide,
or a pharmaceutically acceptable salt thereof to a patient in need thereof.

8. The method of claim 7 wherein the compound is 5-(difluoromethyl)-6-(hydroxymethyl)-N-{1-[3-(trifluoromethyl)benzyl]-1H-imidazol-4-yl}nicotinamide, or a pharmaceutically acceptable salt thereof.

9. The method of claim 7 wherein the compound is 5-(difluoromethyl)-6-(hydroxymethyl)-N-[1-(3,4,5-trifluorobenzyl)-1H-imidazol-4-yl]nicotinamide, or a pharmaceutically acceptable salt thereof.

10. The method of claim 7 wherein the compound is 6-(hydroxymethyl)-5-methyl-N-[1-(3,4,5-trifluorobenzyl)-1H-imidazol-4-yl]nicotinamide, or a pharmaceutically acceptable salt thereof.

11. The method of claim 7 wherein the compound is 5-amino -6-(hydroxymethyl)-N-{1-[3-(trifluoromethyl)benzyl]-1H-imidazol-4-yl}nicotinamide, or a pharmaceutically acceptable salt thereof.

12. The method of claim 7 wherein the compound is 5-amino-6-(hydroxymethyl)-N-[1-(3,4,5-trifluorobenzyl)-1H-imidazol-4-yl]nicotinamide, or a pharmaceutically acceptable salt thereof.

13. The method of claim 7 which comprises inhibiting the sphere-forming ability of cancer cells.

14. A method for inhibiting the sphere-forming ability of cancer cells, which comprises administering a therapeutically effective amount of a compound selected from the group consisting of:
   5-(difluoromethyl)-6-(hydroxymethyl)-N-{1-[3-(trifluoromethyl)benzyl]-1H-imidazol-4-yl}nicotinamide;
   5-(difluoromethyl)-6-(hydroxymethyl)-N-[1-(3,4,5-trifluorobenzyl)-1H-imidazol-4-yl]nicotinamide;
   6-(hydroxymethyl)-5-methyl-N-[1-(3,4,5-trifluorobenzyl)-1H-imidazol-4-yl]nicatinamide;

5-amino-6-(hydroxymethyl)-N-{1-[3-(trifluoromethyl)
benzyl]-1H-imidazol-4-yl}nicotinamide; and
5-amino-6-(hydroxymethyl)-N-[1-(3,4,5-trifluorobenzyl)-1H-imidazol-4-yl]nicotinamide,
or a pharmaceutically acceptable salt thereof to a patient in need thereof.

* * * * *

UNITED STATES PATENT AND TRADEMARK OFFICE
CERTIFICATE OF CORRECTION

PATENT NO. : 9,828,362 B2
APPLICATION NO. : 15/443892
DATED : November 28, 2017
INVENTOR(S) : Hitoshi Ban et al.

It is certified that error appears in the above-identified patent and that said Letters Patent is hereby corrected as shown below:

In the Specification

Column 107, Line 29-30; After "start of administration in the" remove "present compound." and insert -- control -- therefor.

Signed and Sealed this
Tenth Day of July, 2018

Andrei Iancu
*Director of the United States Patent and Trademark Office*